US012760091B2

(12) United States Patent
Posey, Jr. et al.

(10) Patent No.: US 12,760,091 B2
(45) Date of Patent: Oct. 13, 2026

(54) FIBRONECTIN TARGETING CHIMERIC ANTIGEN RECEPTORS (CARs)

(71) Applicant: THE TRUSTEES OF THE UNIVERSITY OF PENNSYLVANIA, Philadelphia, PA (US)

(72) Inventors: Avery D. Posey, Jr., Philadelphia, PA (US); Tiffany King, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1018 days.

(21) Appl. No.: 17/773,431

(22) PCT Filed: Oct. 30, 2020

(86) PCT No.: PCT/US2020/058352
§ 371 (c)(1),
(2) Date: Apr. 29, 2022

(87) PCT Pub. No.: WO2021/087356
PCT Pub. Date: May 6, 2021

(65) Prior Publication Data

US 2022/0380447 A1 Dec. 1, 2022

Related U.S. Application Data

(60) Provisional application No. 62/929,575, filed on Nov. 1, 2019.

(51) Int. Cl.

| | |
|---|---|
| ***A61K 40/31*** | (2025.01) |
| ***A61K 40/11*** | (2025.01) |
| ***A61K 40/42*** | (2025.01) |
| ***C07K 14/705*** | (2006.01) |
| ***C07K 16/18*** | (2006.01) |

(52) U.S. Cl.
CPC .............. *C07K 16/18* (2013.01); *A61K 40/11* (2025.01); *A61K 40/31* (2025.01); *A61K 40/4211* (2025.01); *A61K 40/4257* (2025.01); *A61K 40/4274* (2025.01); *C07K 14/7051* (2013.01); *C07K 14/70517* (2013.01); *C07K 14/70578* (2013.01); *A61K 2239/28* (2023.05); *A61K 2239/31* (2023.05); *A61K 2239/38* (2023.05); *A61K 2239/58* (2023.05)

(58) Field of Classification Search
None
See application file for complete search history.

(56) References Cited

U.S. PATENT DOCUMENTS

| | | | |
|---|---|---|---|
| 4,894,326 | A | 1/1990 | Matsuura |
| 10,308,717 | B2 | 6/2019 | Brogdon |
| 2010/0104577 | A1 | 4/2010 | Golde |

FOREIGN PATENT DOCUMENTS

| | | |
|---|---|---|
| WO | 2008045962 | 4/2008 |
| WO | 2019018402 | 1/2019 |

OTHER PUBLICATIONS

International Search Report and Written Opinion issued in App. No. PCT/US20/58352, mailing date Mar. 23, 2021, 19 pages.
Matsuura H, Hakomori S-I, "The Oncofetal Domain of Fibronectin Defined by Monoclonal Antibody FDC-6: Its Presence in Fibronectins From Fetal and Tumor Tissues and Its Absence in Those From Normal Adult Tissues and Plasma", Proceedings of the National Academy of Sciences, National Academy of Sciences, (Oct. 1, 1985), vol. 82, doi:10.1073/pnas.82.19.6517, ISSN 0027-8424, pp. 6517-6521, XP000984048.
Steentoft Catharina, Migliorini Denis, King Tiffany R, Mandel Ulla, June Carl H, Posey Avery D, "Glycan-directed CAR-T cells", Glycobiology, (Sep. 1, 2018), vol. 28, No. 9, doi:10.1093/glycob/cwy008, pp. 656-669, XP055932243.
Yushu Joy Xie et al., "Nanobody-based CAR T cells that target the tumor microenvironment inhibit the growth of solid tumors in immunocompetent mice", PNAS vol. 116, No. 16, 2019, 9 pages.

*Primary Examiner* — Michail A Belyavskyi
(74) *Attorney, Agent, or Firm* — Saul Ewing LLP; Kathryn Doyle; Alireza Behrooz

(57) ABSTRACT

The present disclosure provides compositions and methods comprising chimeric antigen receptors (CARs) capable of binding tumor-specific isoforms of fibronectin.

16 Claims, 21 Drawing Sheets

Specification includes a Sequence Listing.

Day 41 tumor excision – IHC anti-hCD3 staining

SEQUENCE LISTING

<160> NUMBER OF SEQ ID NOS: 85

<210> SEQ ID NO 1
<211> LENGTH: 11
<212> TYPE: PRT
<213> ORGANISM: Artificial Sequence
<220> FEATURE:
<223> OTHER INFORMATION: FDC-6 HCDR1

<400> SEQUENCE: 1

Phe Ser Leu Ser Thr Ser Gly Met Gly Val Gly
1 5 10

<210> SEQ ID NO 2
<211> LENGTH: 13
<212> TYPE: PRT
<213> ORGANISM: Artificial Sequence
<220> FEATURE:
<223> OTHER INFORMATION: FDC-6 HCDR2

<400> SEQUENCE: 2

Trp Leu Ala His Ile Trp Trp Asp Asp Thr Arg Arg Tyr
1 5 10

<210> SEQ ID NO 3
<211> LENGTH: 13
<212> TYPE: PRT
<213> ORGANISM: Artificial Sequence
<220> FEATURE:
<223> OTHER INFORMATION: FDC-6 HCDR3

<400> SEQUENCE: 3

Ala Arg Met Asn Gly Asn Tyr Pro Ala Trp Phe Ala Tyr
1 5 10

<210> SEQ ID NO 4
<211> LENGTH: 13
<212> TYPE: PRT
<213> ORGANISM: Artificial Sequence
<220> FEATURE:
<223> OTHER INFORMATION: FDC-6 LCDR1

<400> SEQUENCE: 4

Gln Asn Ile Val His Ser Asn Gly Asn Thr Tyr Leu Glu
1 5 10

<210> SEQ ID NO 5
<211> LENGTH: 11
<212> TYPE: PRT
<213> ORGANISM: Artificial Sequence
<220> FEATURE:
<223> OTHER INFORMATION: FDC-6 LCDR2

<400> SEQUENCE: 5

Leu Leu Ile Tyr Lys Val Ser Asn Arg Phe Ser
1 5 10

<210> SEQ ID NO 6
<211> LENGTH: 8
<212> TYPE: PRT
<213> ORGANISM: Artificial Sequence
<220> FEATURE:
<223> OTHER INFORMATION: FDC-6 LCDR3

<400> SEQUENCE: 6

Phe Gln Gly Ser His Ile Pro Pro
1 5

```
<210> SEQ ID NO 7
<211> LENGTH: 121
<212> TYPE: PRT
<213> ORGANISM: Artificial Sequence
<220> FEATURE:
<223> OTHER INFORMATION: FDC-6 VH

<400> SEQUENCE: 7

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Thr Arg Arg Tyr Asn Pro Ala
    50                  55                  60

Leu Lys Ser Arg Leu Thr Ile Ser Asn Asp Thr Ser Asn Asn Gln Val
65                  70                  75                  80

Phe Leu Lys Ile Ala Ser Val Asp Thr Ala Asp Thr Ala Thr Tyr Tyr
                85                  90                  95

Cys Ala Arg Met Asn Gly Asn Tyr Pro Ala Trp Phe Ala Tyr Trp Gly
            100                 105                 110

Gln Gly Thr Leu Val Thr Val Ser Ser
        115                 120


<210> SEQ ID NO 8
<211> LENGTH: 112
<212> TYPE: PRT
<213> ORGANISM: Artificial Sequence
<220> FEATURE:
<223> OTHER INFORMATION: FDC-6 VL

<400> SEQUENCE: 8

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Asn Thr Tyr Leu Glu Trp Tyr Leu Leu Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Tyr Cys Phe Gln Gly
                85                  90                  95

Ser His Ile Pro Pro Thr Phe Gly Gly Gly Thr Lys Leu Glu Ile Lys
            100                 105                 110


<210> SEQ ID NO 9
<211> LENGTH: 15
<212> TYPE: PRT
<213> ORGANISM: Artificial Sequence
<220> FEATURE:
<223> OTHER INFORMATION: linker

<400> SEQUENCE: 9

Gly Gly Gly Gly Ser Gly Gly Gly Gly Ser Gly Gly Gly Gly Ser
1               5                   10                  15
```

<210> SEQ ID NO 10
<211> LENGTH: 248
<212> TYPE: PRT
<213> ORGANISM: Artificial Sequence
<220> FEATURE:
<223> OTHER INFORMATION: FDC-6 scFv (HL)

<400> SEQUENCE: 10

Gln Val Thr Leu Lys Glu Ser Gly Pro Gly Ile Leu Gln Pro Ser Gln
1 5 10 15

Thr Leu Ser Leu Thr Cys Ser Phe Ser Gly Phe Ser Leu Ser Thr Ser
20 25 30

Gly Met Gly Val Gly Trp Ile Arg Gln Pro Ser Gly Lys Gly Leu Glu
35 40 45

Trp Leu Ala His Ile Trp Trp Asp Asp Thr Arg Arg Tyr Asn Pro Ala
50 55 60

Leu Lys Ser Arg Leu Thr Ile Ser Asn Asp Thr Ser Asn Asn Gln Val
65 70 75 80

Phe Leu Lys Ile Ala Ser Val Asp Thr Ala Asp Thr Ala Thr Tyr Tyr
85 90 95

Cys Ala Arg Met Asn Gly Asn Tyr Pro Ala Trp Phe Ala Tyr Trp Gly
100 105 110

Gln Gly Thr Leu Val Thr Val Ser Ser Gly Gly Gly Gly Ser Gly Gly
115 120 125

Gly Gly Ser Gly Gly Gly Gly Ser Asp Val Leu Met Thr Gln Thr Pro
130 135 140

Leu Ser Leu Pro Val Ser Leu Gly Asp Gln Ala Ser Ile Ser Cys Arg
145 150 155 160

Ser Ser Gln Asn Ile Val His Ser Asn Gly Asn Thr Tyr Leu Glu Trp
165 170 175

Tyr Leu Leu Lys Pro Gly Gln Ser Pro Lys Leu Leu Ile Tyr Lys Val
180 185 190

Ser Asn Arg Phe Ser Gly Val Pro Asp Arg Phe Ser Gly Ser Gly Ser
195 200 205

Gly Thr Asp Phe Thr Leu Lys Ile Ser Arg Val Glu Ala Glu Asp Leu
210 215 220

Gly Ile Tyr Tyr Cys Phe Gln Gly Ser His Ile Pro Pro Thr Phe Gly
225 230 235 240

Gly Gly Thr Lys Leu Glu Ile Lys
245

<210> SEQ ID NO 11
<211> LENGTH: 248
<212> TYPE: PRT
<213> ORGANISM: Artificial Sequence
<220> FEATURE:
<223> OTHER INFORMATION: FDC-6 scFv (LH)

<400> SEQUENCE: 11

Asp Val Leu Met Thr Gln Thr Pro Leu Ser Leu Pro Val Ser Leu Gly
1 5 10 15

Asp Gln Ala Ser Ile Ser Cys Arg Ser Ser Gln Asn Ile Val His Ser
20 25 30

Asn Gly Asn Thr Tyr Leu Glu Trp Tyr Leu Leu Lys Pro Gly Gln Ser
35 40 45

Pro Lys Leu Leu Ile Tyr Lys Val Ser Asn Arg Phe Ser Gly Val Pro
50 55 60

```
Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Tyr Cys Phe Gln Gly
                85                  90                  95

Ser His Ile Pro Pro Thr Phe Gly Gly Gly Thr Lys Leu Glu Ile Lys
            100                 105                 110

Gly Gly Gly Gly Ser Gly Gly Gly Gly Ser Gly Gly Gly Gly Ser Gln
        115                 120                 125

Val Thr Leu Lys Glu Ser Gly Pro Gly Ile Leu Gln Pro Ser Gln Thr
    130                 135                 140

Leu Ser Leu Thr Cys Ser Phe Ser Gly Phe Ser Leu Ser Thr Ser Gly
145                 150                 155                 160

Met Gly Val Gly Trp Ile Arg Gln Pro Ser Gly Lys Gly Leu Glu Trp
                165                 170                 175

Leu Ala His Ile Trp Trp Asp Asp Thr Arg Arg Tyr Asn Pro Ala Leu
            180                 185                 190

Lys Ser Arg Leu Thr Ile Ser Asn Asp Thr Ser Asn Asn Gln Val Phe
        195                 200                 205

Leu Lys Ile Ala Ser Val Asp Thr Ala Asp Thr Ala Thr Tyr Tyr Cys
    210                 215                 220

Ala Arg Met Asn Gly Asn Tyr Pro Ala Trp Phe Ala Tyr Trp Gly Gln
225                 230                 235                 240

Gly Thr Leu Val Thr Val Ser Ser
                245


<210> SEQ ID NO 12
<211> LENGTH: 9
<212> TYPE: PRT
<213> ORGANISM: Artificial Sequence
<220> FEATURE:
<223> OTHER INFORMATION: C6 HCDR1

<400> SEQUENCE: 12

Leu Thr Phe Asn Thr Tyr Ala Met Asn
1               5


<210> SEQ ID NO 13
<211> LENGTH: 16
<212> TYPE: PRT
<213> ORGANISM: Artificial Sequence
<220> FEATURE:
<223> OTHER INFORMATION: C6 HCDR2

<400> SEQUENCE: 13

Trp Val Ala Arg Ile Arg Ser Lys Ser Asn Asn Tyr Ala Thr Tyr Tyr
1               5                   10                  15


<210> SEQ ID NO 14
<211> LENGTH: 13
<212> TYPE: PRT
<213> ORGANISM: Artificial Sequence
<220> FEATURE:
<223> OTHER INFORMATION: C6 HCDR3

<400> SEQUENCE: 14

Lys Gln Gly Gly Asn Ser Leu Tyr Trp Tyr Phe Asp Val
1               5                   10


<210> SEQ ID NO 15
<211> LENGTH: 14
```

```
<212> TYPE: PRT
<213> ORGANISM: Artificial Sequence
<220> FEATURE:
<223> OTHER INFORMATION: C6 LCDR1

<400> SEQUENCE: 15

Gln Ser Leu Leu Tyr Ser Ser Asn Gln Lys Asn Tyr Leu Ala
1               5                   10


<210> SEQ ID NO 16
<211> LENGTH: 11
<212> TYPE: PRT
<213> ORGANISM: Artificial Sequence
<220> FEATURE:
<223> OTHER INFORMATION: C6 LCDR2

<400> SEQUENCE: 16

Leu Leu Ile Tyr Trp Ala Ser Thr Gly Glu Ser
1               5                   10


<210> SEQ ID NO 17
<211> LENGTH: 8
<212> TYPE: PRT
<213> ORGANISM: Artificial Sequence
<220> FEATURE:
<223> OTHER INFORMATION: C6 LCDR3

<400> SEQUENCE: 17

Gln Gln Tyr Tyr Ser Tyr Pro Leu
1               5


<210> SEQ ID NO 18
<211> LENGTH: 123
<212> TYPE: PRT
<213> ORGANISM: Artificial Sequence
<220> FEATURE:
<223> OTHER INFORMATION: C6 VH

<400> SEQUENCE: 18

Glu Val Gln Leu Val Glu Ser Gly Gly Gly Leu Val Gln Pro Lys Gly
1               5                   10                  15

Ser Leu Lys Ile Ser Cys Ala Ala Ser Gly Leu Thr Phe Asn Thr Tyr
            20                  25                  30

Ala Met Asn Trp Val Arg Gln Ala Pro Arg Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Lys Gln Gly Gly Asn Ser Leu Tyr Trp Tyr Phe Asp Val
            100                 105                 110

Trp Gly Ala Gly Thr Thr Val Thr Val Ser Ser
        115                 120


<210> SEQ ID NO 19
<211> LENGTH: 113
<212> TYPE: PRT
<213> ORGANISM: Artificial Sequence
<220> FEATURE:
<223> OTHER INFORMATION: C6 VL

<400> SEQUENCE: 19
```

Asp Ile Val Met Ser Gln Ser Pro Ser Ser Leu Ala Val Ser Val Gly
1 5 10 15

Glu Lys Val Thr Met Ser Cys Lys Ser Ser Gln Ser Leu Leu Tyr Ser
20 25 30

Ser Asn Gln Lys Asn Tyr Leu Ala Trp Tyr Gln Gln Arg Pro Gly Gln
35 40 45

Ser Pro Lys Leu Leu Ile Tyr Trp Ala Ser Thr Gly Glu Ser Gly Val
50 55 60

Pro Asp Arg Phe Thr Gly Ser Gly Ser Gly Thr Asp Phe Thr Leu Thr
65 70 75 80

Ile Ser Ser Val Lys Ala Glu Asp Leu Ala Val Tyr Tyr Cys Gln Gln
85 90 95

Tyr Tyr Ser Tyr Pro Leu Thr Phe Gly Ala Gly Thr Lys Leu Glu Leu
100 105 110

Lys

<210> SEQ ID NO 20
<211> LENGTH: 18
<212> TYPE: PRT
<213> ORGANISM: Artificial Sequence
<220> FEATURE:
<223> OTHER INFORMATION: linker

<400> SEQUENCE: 20

Gly Ser Thr Ser Gly Ser Gly Lys Pro Gly Ser Gly Glu Gly Ser Ser
1 5 10 15

Lys Gly

<210> SEQ ID NO 21
<211> LENGTH: 258
<212> TYPE: PRT
<213> ORGANISM: Artificial Sequence
<220> FEATURE:
<223> OTHER INFORMATION: C6 scFv (HL)

<400> SEQUENCE: 21

Glu Val Gln Leu Val Glu Ser Gly Gly Gly Leu Val Gln Pro Lys Gly
1 5 10 15

Ser Leu Lys Ile Ser Cys Ala Ala Ser Gly Leu Thr Phe Asn Thr Tyr
20 25 30

Ala Met Asn Trp Val Arg Gln Ala Pro Arg Lys Gly Leu Glu Trp Val
35 40 45

Ala Arg Ile Arg Ser Lys Ser Asn Asn Tyr Ala Thr Tyr Tyr Ala Asp
50 55 60

Ser Val Lys Asp Arg Phe Thr Ile Ser Arg Asp Asp Ser Gln Ser Met
65 70 75 80

Leu Tyr Leu Gln Met Asn Asn Leu Lys Thr Glu Asp Thr Ala Met Tyr
85 90 95

Tyr Cys Val Lys Gln Gly Gly Asn Ser Leu Tyr Trp Tyr Phe Asp Val
100 105 110

Trp Gly Ala Gly Thr Thr Val Thr Val Ser Ser Ser Gly Gly Ser Thr
115 120 125

Ser Gly Ser Gly Lys Pro Gly Ser Gly Glu Gly Ser Ser Lys Gly Gly
130 135 140

Ser Asp Ile Val Met Ser Gln Ser Pro Ser Ser Leu Ala Val Ser Val
145 150 155 160

Gly Glu Lys Val Thr Met Ser Cys Lys Ser Ser Gln Ser Leu Leu Tyr
165 170 175

Ser Ser Asn Gln Lys Asn Tyr Leu Ala Trp Tyr Gln Gln Arg Pro Gly
180 185 190

Gln Ser Pro Lys Leu Leu Ile Tyr Trp Ala Ser Thr Gly Glu Ser Gly
195 200 205

Val Pro Asp Arg Phe Thr Gly Ser Gly Ser Gly Thr Asp Phe Thr Leu
210 215 220

Thr Ile Ser Ser Val Lys Ala Glu Asp Leu Ala Val Tyr Tyr Cys Gln
225 230 235 240

Gln Tyr Tyr Ser Tyr Pro Leu Thr Phe Gly Ala Gly Thr Lys Leu Glu
245 250 255

Leu Lys

<210> SEQ ID NO 22
<211> LENGTH: 254
<212> TYPE: PRT
<213> ORGANISM: Artificial Sequence
<220> FEATURE:
<223> OTHER INFORMATION: C6 scFv (LH)

<400> SEQUENCE: 22

Asp Ile Val Met Ser Gln Ser Pro Ser Ser Leu Ala Val Ser Val Gly
1 5 10 15

Glu Lys Val Thr Met Ser Cys Lys Ser Ser Gln Ser Leu Leu Tyr Ser
20 25 30

Ser Asn Gln Lys Asn Tyr Leu Ala Trp Tyr Gln Gln Arg Pro Gly Gln
35 40 45

Ser Pro Lys Leu Leu Ile Tyr Trp Ala Ser Thr Gly Glu Ser Gly Val
50 55 60

Pro Asp Arg Phe Thr Gly Ser Gly Ser Gly Thr Asp Phe Thr Leu Thr
65 70 75 80

Ile Ser Ser Val Lys Ala Glu Asp Leu Ala Val Tyr Tyr Cys Gln Gln
85 90 95

Tyr Tyr Ser Tyr Pro Leu Thr Phe Gly Ala Gly Thr Lys Leu Glu Leu
100 105 110

Lys Gly Ser Thr Ser Gly Ser Gly Lys Pro Gly Ser Gly Glu Gly Ser
115 120 125

Ser Lys Gly Glu Val Gln Leu Val Glu Ser Gly Gly Gly Leu Val Gln
130 135 140

Pro Lys Gly Ser Leu Lys Ile Ser Cys Ala Ala Ser Gly Leu Thr Phe
145 150 155 160

Asn Thr Tyr Ala Met Asn Trp Val Arg Gln Ala Pro Arg Lys Gly Leu
165 170 175

Glu Trp Val Ala Arg Ile Arg Ser Lys Ser Asn Asn Tyr Ala Thr Tyr
180 185 190

Tyr Ala Asp Ser Val Lys Asp Arg Phe Thr Ile Ser Arg Asp Asp Ser
195 200 205

Gln Ser Met Leu Tyr Leu Gln Met Asn Asn Leu Lys Thr Glu Asp Thr
210 215 220

Ala Met Tyr Tyr Cys Val Lys Gln Gly Gly Asn Ser Leu Tyr Trp Tyr
225 230 235 240

Phe Asp Val Trp Gly Ala Gly Thr Thr Val Thr Val Ser Ser
245 250

<210> SEQ ID NO 23
<211> LENGTH: 9
<212> TYPE: PRT
<213> ORGANISM: Artificial Sequence
<220> FEATURE:
<223> OTHER INFORMATION: L19 HCDR1

<400> SEQUENCE: 23

Phe Thr Phe Ser Ser Phe Ser Met Ser
1               5

<210> SEQ ID NO 24
<211> LENGTH: 14
<212> TYPE: PRT
<213> ORGANISM: Artificial Sequence
<220> FEATURE:
<223> OTHER INFORMATION: L19 HCDR2

<400> SEQUENCE: 24

Trp Val Ser Ser Ile Ser Gly Ser Ser Gly Thr Thr Tyr Tyr
1               5                   10

<210> SEQ ID NO 25
<211> LENGTH: 8
<212> TYPE: PRT
<213> ORGANISM: Artificial Sequence
<220> FEATURE:
<223> OTHER INFORMATION: L19 HCDR3

<400> SEQUENCE: 25

Lys Pro Phe Pro Tyr Phe Asp Tyr
1               5

<210> SEQ ID NO 26
<211> LENGTH: 9
<212> TYPE: PRT
<213> ORGANISM: Artificial Sequence
<220> FEATURE:
<223> OTHER INFORMATION: L19 LCDR1

<400> SEQUENCE: 26

Gln Ser Val Ser Ser Ser Phe Leu Ala
1               5

<210> SEQ ID NO 27
<211> LENGTH: 11
<212> TYPE: PRT
<213> ORGANISM: Artificial Sequence
<220> FEATURE:
<223> OTHER INFORMATION: L19 LCDR2

<400> SEQUENCE: 27

Leu Leu Ile Tyr Tyr Ala Ser Ser Arg Ala Thr
1               5                   10

<210> SEQ ID NO 28
<211> LENGTH: 8
<212> TYPE: PRT
<213> ORGANISM: Artificial Sequence
<220> FEATURE:
<223> OTHER INFORMATION: L19 LCDR3

<400> SEQUENCE: 28

Gln Gln Thr Gly Arg Ile Pro Pro
1               5

<210> SEQ ID NO 29

<211> LENGTH: 116
<212> TYPE: PRT
<213> ORGANISM: Artificial Sequence
<220> FEATURE:
<223> OTHER INFORMATION: L19 VH

<400> SEQUENCE: 29

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser
        115

<210> SEQ ID NO 30
<211> LENGTH: 108
<212> TYPE: PRT
<213> ORGANISM: Artificial Sequence
<220> FEATURE:
<223> OTHER INFORMATION: L19 VL

<400> SEQUENCE: 30

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
        35                  40                  45

Ile Tyr Tyr Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Thr Gly Arg Ile Pro
                85                  90                  95

Pro Thr Phe Gly Gln Gly Thr Lys Val Glu Ile Lys
            100                 105

<210> SEQ ID NO 31
<211> LENGTH: 239
<212> TYPE: PRT
<213> ORGANISM: Artificial Sequence
<220> FEATURE:
<223> OTHER INFORMATION: L19 scFv (HL)

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

```
Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Glu Ile Val Leu Thr Gln Ser Pro Gly Thr Leu Ser Leu
    130                 135                 140

Ser Pro Gly Glu Arg Ala Thr Leu Ser Cys Arg Ala Ser Gln Ser Val
145                 150                 155                 160

Ser Ser Ser Phe Leu Ala Trp Tyr Gln Gln Lys Pro Gly Gln Ala Pro
                165                 170                 175

Arg Leu Leu Ile Tyr Tyr Ala Ser Ser Arg Ala Thr Gly Ile Pro Asp
            180                 185                 190

Arg Phe Ser Gly Ser Gly Ser Gly Thr Asp Phe Thr Leu Thr Ile Ser
        195                 200                 205

Arg Leu Glu Pro Glu Asp Phe Ala Val Tyr Tyr Cys Gln Gln Thr Gly
    210                 215                 220

Arg Ile Pro Pro Thr Phe Gly Gln Gly Thr Lys Val Glu Ile Lys
225                 230                 235


<210> SEQ ID NO 32
<211> LENGTH: 239
<212> TYPE: PRT
<213> ORGANISM: Artificial Sequence
<220> FEATURE:
<223> OTHER INFORMATION: L19 scFv (LH)

<400> SEQUENCE: 32

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
        35                  40                  45

Ile Tyr Tyr Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Thr Gly Arg Ile Pro
                85                  90                  95

Pro Thr Phe Gly Gln Gly Thr Lys Val Glu Ile Lys Gly Gly Gly Gly
            100                 105                 110

Ser Gly Gly Gly Gly Ser Gly Gly Gly Gly Ser Glu Val Gln Leu Leu
        115                 120                 125

Glu Ser Gly Gly Gly Leu Val Gln Pro Gly Gly Ser Leu Arg Leu Ser
    130                 135                 140

Cys Ala Ala Ser Gly Phe Thr Phe Ser Ser Phe Ser Met Ser Trp Val
145                 150                 155                 160
```

```
Arg Gln Ala Pro Gly Lys Gly Leu Glu Trp Val Ser Ser Ile Ser Gly
                165                 170                 175

Ser Ser Gly Thr Thr Tyr Tyr Ala Asp Ser Val Lys Gly Arg Phe Thr
            180                 185                 190

Ile Ser Arg Asp Asn Ser Lys Asn Thr Leu Tyr Leu Gln Met Asn Ser
        195                 200                 205

Leu Arg Ala Glu Asp Thr Ala Val Tyr Tyr Cys Ala Lys Pro Phe Pro
    210                 215                 220

Tyr Phe Asp Tyr Trp Gly Gln Gly Thr Leu Val Thr Val Ser Ser
225                 230                 235


<210> SEQ ID NO 33
<211> LENGTH: 21
<212> TYPE: PRT
<213> ORGANISM: Artificial Sequence
<220> FEATURE:
<223> OTHER INFORMATION: CD8? Leader

<400> SEQUENCE: 33

Met Ala Leu Pro Val Thr Ala Leu Leu Leu Pro Leu Ala Leu Leu Leu
1               5                   10                  15

His Ala Ala Arg Pro
            20


<210> SEQ ID NO 34
<211> LENGTH: 45
<212> TYPE: PRT
<213> ORGANISM: Artificial Sequence
<220> FEATURE:
<223> OTHER INFORMATION: CD8? Hinge

<400> SEQUENCE: 34

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45


<210> SEQ ID NO 35
<211> LENGTH: 24
<212> TYPE: PRT
<213> ORGANISM: Artificial Sequence
<220> FEATURE:
<223> OTHER INFORMATION: CD8? Transmembrane

<400> SEQUENCE: 35

Ile Tyr Ile Trp Ala Pro Leu Ala Gly Thr Cys Gly Val Leu Leu Leu
1               5                   10                  15

Ser Leu Val Ile Thr Leu Tyr Cys
            20


<210> SEQ ID NO 36
<211> LENGTH: 42
<212> TYPE: PRT
<213> ORGANISM: Artificial Sequence
<220> FEATURE:
<223> OTHER INFORMATION: 4-1BB ICD

<400> SEQUENCE: 36

Lys Arg Gly Arg Lys Lys Leu Leu Tyr Ile Phe Lys Gln Pro Phe Met
1               5                   10                  15
```

```
Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40


<210> SEQ ID NO 37
<211> LENGTH: 112
<212> TYPE: PRT
<213> ORGANISM: Artificial Sequence
<220> FEATURE:
<223> OTHER INFORMATION: CD3?

<400> SEQUENCE: 37

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 38
<211> LENGTH: 496
<212> TYPE: PRT
<213> ORGANISM: Artificial Sequence
<220> FEATURE:
<223> OTHER INFORMATION: FDC-6 CAR (HL)

<400> SEQUENCE: 38

Met Ala Leu Pro Val Thr Ala Leu Leu Leu Pro Leu Ala Leu Leu Leu
1               5                   10                  15

His Ala Ala Arg Pro Gly Ser Gln Val Thr Leu Lys Glu Ser Gly Pro
            20                  25                  30

Gly Ile Leu Gln Pro Ser Gln Thr Leu Ser Leu Thr Cys Ser Phe Ser
        35                  40                  45

Gly Phe Ser Leu Ser Thr Ser Gly Met Gly Val Gly Trp Ile Arg Gln
    50                  55                  60

Pro Ser Gly Lys Gly Leu Glu Trp Leu Ala His Ile Trp Trp Asp Asp
65                  70                  75                  80

Thr Arg Arg Tyr Asn Pro Ala Leu Lys Ser Arg Leu Thr Ile Ser Asn
                85                  90                  95

Asp Thr Ser Asn Asn Gln Val Phe Leu Lys Ile Ala Ser Val Asp Thr
            100                 105                 110

Ala Asp Thr Ala Thr Tyr Tyr Cys Ala Arg Met Asn Gly Asn Tyr Pro
        115                 120                 125

Ala Trp Phe Ala Tyr Trp Gly Gln Gly Thr Leu Val Thr Val Ser Ser
    130                 135                 140

Gly Gly Gly Gly Ser Gly Gly Gly Gly Ser Gly Gly Gly Gly Ser Asp
145                 150                 155                 160

Val Leu Met Thr Gln Thr Pro Leu Ser Leu Pro Val Ser Leu Gly Asp
                165                 170                 175
```

```
Gln Ala Ser Ile Ser Cys Arg Ser Ser Gln Asn Ile Val His Ser Asn
            180                 185                 190

Gly Asn Thr Tyr Leu Glu Trp Tyr Leu Leu Lys Pro Gly Gln Ser Pro
        195                 200                 205

Lys Leu Leu Ile Tyr Lys Val Ser Asn Arg Phe Ser Gly Val Pro Asp
    210                 215                 220

Arg Phe Ser Gly Ser Gly Ser Gly Thr Asp Phe Thr Leu Lys Ile Ser
225                 230                 235                 240

Arg Val Glu Ala Glu Asp Leu Gly Ile Tyr Tyr Cys Phe Gln Gly Ser
                245                 250                 255

His Ile Pro Pro Thr Phe Gly Gly Gly Thr Lys Leu Glu Ile Lys Ser
            260                 265                 270

Gly Thr Thr Thr Pro Ala Pro Arg Pro Pro Thr Pro Ala Pro Thr Ile
        275                 280                 285

Ala Ser Gln Pro Leu Ser Leu Arg Pro Glu Ala Cys Arg Pro Ala Ala
    290                 295                 300

Gly Gly Ala Val His Thr Arg Gly Leu Asp Phe Ala Cys Asp Ile Tyr
305                 310                 315                 320

Ile Trp Ala Pro Leu Ala Gly Thr Cys Gly Val Leu Leu Leu Ser Leu
                325                 330                 335

Val Ile Thr Leu Tyr Cys Lys Arg Gly Arg Lys Lys Leu Leu Tyr Ile
            340                 345                 350

Phe Lys Gln Pro Phe Met Arg Pro Val Gln Thr Thr Gln Glu Glu Asp
        355                 360                 365

Gly Cys Ser Cys Arg Phe Pro Glu Glu Glu Glu Gly Gly Cys Glu Leu
    370                 375                 380

Arg Val Lys Phe Ser Arg Ser Ala Asp Ala Pro Ala Tyr Lys Gln Gly
385                 390                 395                 400

Gln Asn Gln Leu Tyr Asn Glu Leu Asn Leu Gly Arg Arg Glu Glu Tyr
                405                 410                 415

Asp Val Leu Asp Lys Arg Arg Gly Arg Asp Pro Glu Met Gly Gly Lys
            420                 425                 430

Pro Arg Arg Lys Asn Pro Gln Glu Gly Leu Tyr Asn Glu Leu Gln Lys
        435                 440                 445

Asp Lys Met Ala Glu Ala Tyr Ser Glu Ile Gly Met Lys Gly Glu Arg
    450                 455                 460

Arg Arg Gly Lys Gly His Asp Gly Leu Tyr Gln Gly Leu Ser Thr Ala
465                 470                 475                 480

Thr Lys Asp Thr Tyr Asp Ala Leu His Met Gln Ala Leu Pro Pro Arg
                485                 490                 495
```

<210> SEQ ID NO 39
<211> LENGTH: 496
<212> TYPE: PRT
<213> ORGANISM: Artificial Sequence
<220> FEATURE:
<223> OTHER INFORMATION: FDC-6 CAR (LH)

<400> SEQUENCE: 39

```
Met Ala Leu Pro Val Thr Ala Leu Leu Leu Pro Leu Ala Leu Leu Leu
1               5                   10                  15

His Ala Ala Arg Pro Gly Ser Asp Val Leu Met Thr Gln Thr Pro Leu
            20                  25                  30

Ser Leu Pro Val Ser Leu Gly Asp Gln Ala Ser Ile Ser Cys Arg Ser
        35                  40                  45
```

-continued

```
Ser Gln Asn Ile Val His Ser Asn Gly Asn Thr Tyr Leu Glu Trp Tyr
    50                  55                  60

Leu Leu Lys Pro Gly Gln Ser Pro Lys Leu Leu Ile Tyr Lys Val Ser
65                  70                  75                  80

Asn Arg Phe Ser Gly Val Pro Asp Arg Phe Ser Gly Ser Gly Ser Gly
                85                  90                  95

Thr Asp Phe Thr Leu Lys Ile Ser Arg Val Glu Ala Glu Asp Leu Gly
            100                 105                 110

Ile Tyr Tyr Cys Phe Gln Gly Ser His Ile Pro Pro Thr Phe Gly Gly
        115                 120                 125

Gly Thr Lys Leu Glu Ile Lys Gly Gly Gly Gly Ser Gly Gly Gly Gly
    130                 135                 140

Ser Gly Gly Gly Gly Ser Gln Val Thr Leu Lys Glu Ser Gly Pro Gly
145                 150                 155                 160

Ile Leu Gln Pro Ser Gln Thr Leu Ser Leu Thr Cys Ser Phe Ser Gly
                165                 170                 175

Phe Ser Leu Ser Thr Ser Gly Met Gly Val Gly Trp Ile Arg Gln Pro
            180                 185                 190

Ser Gly Lys Gly Leu Glu Trp Leu Ala His Ile Trp Trp Asp Asp Thr
        195                 200                 205

Arg Arg Tyr Asn Pro Ala Leu Lys Ser Arg Leu Thr Ile Ser Asn Asp
    210                 215                 220

Thr Ser Asn Asn Gln Val Phe Leu Lys Ile Ala Ser Val Asp Thr Ala
225                 230                 235                 240

Asp Thr Ala Thr Tyr Tyr Cys Ala Arg Met Asn Gly Asn Tyr Pro Ala
                245                 250                 255

Trp Phe Ala Tyr Trp Gly Gln Gly Thr Leu Val Thr Val Ser Ser Ser
            260                 265                 270

Gly Thr Thr Thr Pro Ala Pro Arg Pro Pro Thr Pro Ala Pro Thr Ile
        275                 280                 285

Ala Ser Gln Pro Leu Ser Leu Arg Pro Glu Ala Cys Arg Pro Ala Ala
    290                 295                 300

Gly Gly Ala Val His Thr Arg Gly Leu Asp Phe Ala Cys Asp Ile Tyr
305                 310                 315                 320

Ile Trp Ala Pro Leu Ala Gly Thr Cys Gly Val Leu Leu Leu Ser Leu
                325                 330                 335

Val Ile Thr Leu Tyr Cys Lys Arg Gly Arg Lys Lys Leu Leu Tyr Ile
            340                 345                 350

Phe Lys Gln Pro Phe Met Arg Pro Val Gln Thr Thr Gln Glu Glu Asp
        355                 360                 365

Gly Cys Ser Cys Arg Phe Pro Glu Glu Glu Glu Gly Gly Cys Glu Leu
    370                 375                 380

Arg Val Lys Phe Ser Arg Ser Ala Asp Ala Pro Ala Tyr Lys Gln Gly
385                 390                 395                 400

Gln Asn Gln Leu Tyr Asn Glu Leu Asn Leu Gly Arg Arg Glu Glu Tyr
                405                 410                 415

Asp Val Leu Asp Lys Arg Arg Gly Arg Asp Pro Glu Met Gly Gly Lys
            420                 425                 430

Pro Arg Arg Lys Asn Pro Gln Glu Gly Leu Tyr Asn Glu Leu Gln Lys
        435                 440                 445

Asp Lys Met Ala Glu Ala Tyr Ser Glu Ile Gly Met Lys Gly Glu Arg
    450                 455                 460
```

```
Arg Arg Gly Lys Gly His Asp Gly Leu Tyr Gln Gly Leu Ser Thr Ala
465                 470                 475                 480

Thr Lys Asp Thr Tyr Asp Ala Leu His Met Gln Ala Leu Pro Pro Arg
                485                 490                 495


<210> SEQ ID NO 40
<211> LENGTH: 506
<212> TYPE: PRT
<213> ORGANISM: Artificial Sequence
<220> FEATURE:
<223> OTHER INFORMATION: C6 CAR (HL)

<400> SEQUENCE: 40

Met Ala Leu Pro Val Thr Ala Leu Leu Leu Pro Leu Ala Leu Leu Leu
1               5                   10                  15

His Ala Ala Arg Pro Gly Ser Glu Val Gln Leu Val Glu Ser Gly Gly
            20                  25                  30

Gly Leu Val Gln Pro Lys Gly Ser Leu Lys Ile Ser Cys Ala Ala Ser
        35                  40                  45

Gly Leu Thr Phe Asn Thr Tyr Ala Met Asn Trp Val Arg Gln Ala Pro
    50                  55                  60

Arg Lys Gly Leu Glu Trp Val Ala Arg Ile Arg Ser Lys Ser Asn Asn
65                  70                  75                  80

Tyr Ala Thr Tyr Tyr Ala Asp Ser Val Lys Asp Arg Phe Thr Ile Ser
                85                  90                  95

Arg Asp Asp Ser Gln Ser Met Leu Tyr Leu Gln Met Asn Asn Leu Lys
            100                 105                 110

Thr Glu Asp Thr Ala Met Tyr Tyr Cys Val Lys Gln Gly Gly Asn Ser
        115                 120                 125

Leu Tyr Trp Tyr Phe Asp Val Trp Gly Ala Gly Thr Thr Val Thr Val
    130                 135                 140

Ser Ser Ser Gly Gly Ser Thr Ser Gly Ser Gly Lys Pro Gly Ser Gly
145                 150                 155                 160

Glu Gly Ser Ser Lys Gly Gly Ser Asp Ile Val Met Ser Gln Ser Pro
                165                 170                 175

Ser Ser Leu Ala Val Ser Val Gly Glu Lys Val Thr Met Ser Cys Lys
            180                 185                 190

Ser Ser Gln Ser Leu Leu Tyr Ser Ser Asn Gln Lys Asn Tyr Leu Ala
        195                 200                 205

Trp Tyr Gln Gln Arg Pro Gly Gln Ser Pro Lys Leu Leu Ile Tyr Trp
    210                 215                 220

Ala Ser Thr Gly Glu Ser Gly Val Pro Asp Arg Phe Thr Gly Ser Gly
225                 230                 235                 240

Ser Gly Thr Asp Phe Thr Leu Thr Ile Ser Ser Val Lys Ala Glu Asp
                245                 250                 255

Leu Ala Val Tyr Tyr Cys Gln Gln Tyr Tyr Ser Tyr Pro Leu Thr Phe
            260                 265                 270

Gly Ala Gly Thr Lys Leu Glu Leu Lys Ser Gly Thr Thr Thr Pro Ala
        275                 280                 285

Pro Arg Pro Pro Thr Pro Ala Pro Thr Ile Ala Ser Gln Pro Leu Ser
    290                 295                 300

Leu Arg Pro Glu Ala Cys Arg Pro Ala Ala Gly Gly Ala Val His Thr
305                 310                 315                 320

Arg Gly Leu Asp Phe Ala Cys Asp Ile Tyr Ile Trp Ala Pro Leu Ala
                325                 330                 335
```

```
Gly Thr Cys Gly Val Leu Leu Leu Ser Leu Val Ile Thr Leu Tyr Cys
            340                 345                 350

Lys Arg Gly Arg Lys Lys Leu Leu Tyr Ile Phe Lys Gln Pro Phe Met
        355                 360                 365

Arg Pro Val Gln Thr Thr Gln Glu Glu Asp Gly Cys Ser Cys Arg Phe
    370                 375                 380

Pro Glu Glu Glu Glu Gly Gly Cys Glu Leu Arg Val Lys Phe Ser Arg
385                 390                 395                 400

Ser Ala Asp Ala Pro Ala Tyr Lys Gln Gly Gln Asn Gln Leu Tyr Asn
                405                 410                 415

Glu Leu Asn Leu Gly Arg Arg Glu Glu Tyr Asp Val Leu Asp Lys Arg
            420                 425                 430

Arg Gly Arg Asp Pro Glu Met Gly Gly Lys Pro Arg Arg Lys Asn Pro
        435                 440                 445

Gln Glu Gly Leu Tyr Asn Glu Leu Gln Lys Asp Lys Met Ala Glu Ala
    450                 455                 460

Tyr Ser Glu Ile Gly Met Lys Gly Glu Arg Arg Arg Gly Lys Gly His
465                 470                 475                 480

Asp Gly Leu Tyr Gln Gly Leu Ser Thr Ala Thr Lys Asp Thr Tyr Asp
                485                 490                 495

Ala Leu His Met Gln Ala Leu Pro Pro Arg
            500                 505


<210> SEQ ID NO 41
<211> LENGTH: 502
<212> TYPE: PRT
<213> ORGANISM: Artificial Sequence
<220> FEATURE:
<223> OTHER INFORMATION: C6 CAR (LH)

<400> SEQUENCE: 41

Met Ala Leu Pro Val Thr Ala Leu Leu Leu Pro Leu Ala Leu Leu Leu
1               5                   10                  15

His Ala Ala Arg Pro Gly Ser Asp Ile Val Met Ser Gln Ser Pro Ser
            20                  25                  30

Ser Leu Ala Val Ser Val Gly Glu Lys Val Thr Met Ser Cys Lys Ser
        35                  40                  45

Ser Gln Ser Leu Leu Tyr Ser Ser Asn Gln Lys Asn Tyr Leu Ala Trp
    50                  55                  60

Tyr Gln Gln Arg Pro Gly Gln Ser Pro Lys Leu Leu Ile Tyr Trp Ala
65                  70                  75                  80

Ser Thr Gly Glu Ser Gly Val Pro Asp Arg Phe Thr Gly Ser Gly Ser
                85                  90                  95

Gly Thr Asp Phe Thr Leu Thr Ile Ser Ser Val Lys Ala Glu Asp Leu
            100                 105                 110

Ala Val Tyr Tyr Cys Gln Gln Tyr Tyr Ser Tyr Pro Leu Thr Phe Gly
        115                 120                 125

Ala Gly Thr Lys Leu Glu Leu Lys Gly Ser Thr Ser Gly Ser Gly Lys
    130                 135                 140

Pro Gly Ser Gly Glu Gly Ser Ser Lys Gly Glu Val Gln Leu Val Glu
145                 150                 155                 160

Ser Gly Gly Gly Leu Val Gln Pro Lys Gly Ser Leu Lys Ile Ser Cys
                165                 170                 175

Ala Ala Ser Gly Leu Thr Phe Asn Thr Tyr Ala Met Asn Trp Val Arg
            180                 185                 190
```

```
Gln Ala Pro Arg Lys Gly Leu Glu Trp Val Ala Arg Ile Arg Ser Lys
        195                 200                 205

Ser Asn Asn Tyr Ala Thr Tyr Tyr Ala Asp Ser Val Lys Asp Arg Phe
    210                 215                 220

Thr Ile Ser Arg Asp Asp Ser Gln Ser Met Leu Tyr Leu Gln Met Asn
225                 230                 235                 240

Asn Leu Lys Thr Glu Asp Thr Ala Met Tyr Tyr Cys Val Lys Gln Gly
                245                 250                 255

Gly Asn Ser Leu Tyr Trp Tyr Phe Asp Val Trp Gly Ala Gly Thr Thr
            260                 265                 270

Val Thr Val Ser Ser Ser Gly Thr Thr Thr Pro Ala Pro Arg Pro Pro
        275                 280                 285

Thr Pro Ala Pro Thr Ile Ala Ser Gln Pro Leu Ser Leu Arg Pro Glu
    290                 295                 300

Ala Cys Arg Pro Ala Ala Gly Gly Ala Val His Thr Arg Gly Leu Asp
305                 310                 315                 320

Phe Ala Cys Asp Ile Tyr Ile Trp Ala Pro Leu Ala Gly Thr Cys Gly
                325                 330                 335

Val Leu Leu Leu Ser Leu Val Ile Thr Leu Tyr Cys Lys Arg Gly Arg
            340                 345                 350

Lys Lys Leu Leu Tyr Ile Phe Lys Gln Pro Phe Met Arg Pro Val Gln
        355                 360                 365

Thr Thr Gln Glu Glu Asp Gly Cys Ser Cys Arg Phe Pro Glu Glu Glu
    370                 375                 380

Glu Gly Gly Cys Glu Leu Arg Val Lys Phe Ser Arg Ser Ala Asp Ala
385                 390                 395                 400

Pro Ala Tyr Lys Gln Gly Gln Asn Gln Leu Tyr Asn Glu Leu Asn Leu
                405                 410                 415

Gly Arg Arg Glu Glu Tyr Asp Val Leu Asp Lys Arg Arg Gly Arg Asp
            420                 425                 430

Pro Glu Met Gly Gly Lys Pro Arg Arg Lys Asn Pro Gln Glu Gly Leu
        435                 440                 445

Tyr Asn Glu Leu Gln Lys Asp Lys Met Ala Glu Ala Tyr Ser Glu Ile
    450                 455                 460

Gly Met Lys Gly Glu Arg Arg Arg Gly Lys Gly His Asp Gly Leu Tyr
465                 470                 475                 480

Gln Gly Leu Ser Thr Ala Thr Lys Asp Thr Tyr Asp Ala Leu His Met
                485                 490                 495

Gln Ala Leu Pro Pro Arg
            500
```

<210> SEQ ID NO 42
<211> LENGTH: 487
<212> TYPE: PRT
<213> ORGANISM: Artificial Sequence
<220> FEATURE:
<223> OTHER INFORMATION: L19 CAR (HL)

<400> SEQUENCE: 42

```
Met Ala Leu Pro Val Thr Ala Leu Leu Leu Pro Leu Ala Leu Leu Leu
1               5                   10                  15

His Ala Ala Arg Pro Gly Ser Glu Val Gln Leu Leu Glu Ser Gly Gly
            20                  25                  30

Gly Leu Val Gln Pro Gly Gly Ser Leu Arg Leu Ser Cys Ala Ala Ser
        35                  40                  45
```

```
Gly Phe Thr Phe Ser Ser Phe Ser Met Ser Trp Val Arg Gln Ala Pro
    50                  55                  60

Gly Lys Gly Leu Glu Trp Val Ser Ser Ile Ser Gly Ser Ser Gly Thr
65                  70                  75                  80

Thr Tyr Tyr Ala Asp Ser Val Lys Gly Arg Phe Thr Ile Ser Arg Asp
                85                  90                  95

Asn Ser Lys Asn Thr Leu Tyr Leu Gln Met Asn Ser Leu Arg Ala Glu
            100                 105                 110

Asp Thr Ala Val Tyr Tyr Cys Ala Lys Pro Phe Pro Tyr Phe Asp Tyr
        115                 120                 125

Trp Gly Gln Gly Thr Leu Val Thr Val Ser Ser Gly Gly Gly Gly Ser
    130                 135                 140

Gly Gly Gly Gly Ser Gly Gly Gly Gly Ser Glu Ile Val Leu Thr Gln
145                 150                 155                 160

Ser Pro Gly Thr Leu Ser Leu Ser Pro Gly Glu Arg Ala Thr Leu Ser
                165                 170                 175

Cys Arg Ala Ser Gln Ser Val Ser Ser Ser Phe Leu Ala Trp Tyr Gln
            180                 185                 190

Gln Lys Pro Gly Gln Ala Pro Arg Leu Leu Ile Tyr Tyr Ala Ser Ser
        195                 200                 205

Arg Ala Thr Gly Ile Pro Asp Arg Phe Ser Gly Ser Gly Ser Gly Thr
    210                 215                 220

Asp Phe Thr Leu Thr Ile Ser Arg Leu Glu Pro Glu Asp Phe Ala Val
225                 230                 235                 240

Tyr Tyr Cys Gln Gln Thr Gly Arg Ile Pro Pro Thr Phe Gly Gln Gly
                245                 250                 255

Thr Lys Val Glu Ile Lys Ser Gly Thr Thr Thr Pro Ala Pro Arg Pro
            260                 265                 270

Pro Thr Pro Ala Pro Thr Ile Ala Ser Gln Pro Leu Ser Leu Arg Pro
        275                 280                 285

Glu Ala Cys Arg Pro Ala Ala Gly Gly Ala Val His Thr Arg Gly Leu
    290                 295                 300

Asp Phe Ala Cys Asp Ile Tyr Ile Trp Ala Pro Leu Ala Gly Thr Cys
305                 310                 315                 320

Gly Val Leu Leu Leu Ser Leu Val Ile Thr Leu Tyr Cys Lys Arg Gly
                325                 330                 335

Arg Lys Lys Leu Leu Tyr Ile Phe Lys Gln Pro Phe Met Arg Pro Val
            340                 345                 350

Gln Thr Thr Gln Glu Glu Asp Gly Cys Ser Cys Arg Phe Pro Glu Glu
        355                 360                 365

Glu Glu Gly Gly Cys Glu Leu Arg Val Lys Phe Ser Arg Ser Ala Asp
    370                 375                 380

Ala Pro Ala Tyr Lys Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
            420                 425                 430

Leu Tyr Asn Glu Leu Gln Lys Asp Lys Met Ala Glu Ala Tyr Ser Glu
        435                 440                 445

Ile Gly Met Lys Gly Glu Arg Arg Arg Gly Lys Gly His Asp Gly Leu
    450                 455                 460

Tyr Gln Gly Leu Ser Thr Ala Thr Lys Asp Thr Tyr Asp Ala Leu His
```

465 470 475 480

Met Gln Ala Leu Pro Pro Arg
485

<210> SEQ ID NO 43
<211> LENGTH: 487
<212> TYPE: PRT
<213> ORGANISM: Artificial Sequence
<220> FEATURE:
<223> OTHER INFORMATION: L19 CAR (LH)

<400> SEQUENCE: 43

Met Ala Leu Pro Val Thr Ala Leu Leu Leu Pro Leu Ala Leu Leu Leu
1 5 10 15

His Ala Ala Arg Pro Gly Ser Glu Ile Val Leu Thr Gln Ser Pro Gly
20 25 30

Thr Leu Ser Leu Ser Pro Gly Glu Arg Ala Thr Leu Ser Cys Arg Ala
35 40 45

Ser Gln Ser Val Ser Ser Ser Phe Leu Ala Trp Tyr Gln Gln Lys Pro
50 55 60

Gly Gln Ala Pro Arg Leu Leu Ile Tyr Tyr Ala Ser Ser Arg Ala Thr
65 70 75 80

Gly Ile Pro Asp Arg Phe Ser Gly Ser Gly Ser Gly Thr Asp Phe Thr
85 90 95

Leu Thr Ile Ser Arg Leu Glu Pro Glu Asp Phe Ala Val Tyr Tyr Cys
100 105 110

Gln Gln Thr Gly Arg Ile Pro Pro Thr Phe Gly Gln Gly Thr Lys Val
115 120 125

Glu Ile Lys Gly Gly Gly Gly Ser Gly Gly Gly Gly Ser Gly Gly Gly
130 135 140

Gly Ser Glu Val Gln Leu Leu Glu Ser Gly Gly Gly Leu Val Gln Pro
145 150 155 160

Gly Gly Ser Leu Arg Leu Ser Cys Ala Ala Ser Gly Phe Thr Phe Ser
165 170 175

Ser Phe Ser Met Ser Trp Val Arg Gln Ala Pro Gly Lys Gly Leu Glu
180 185 190

Trp Val Ser Ser Ile Ser Gly Ser Ser Gly Thr Thr Tyr Tyr Ala Asp
195 200 205

Ser Val Lys Gly Arg Phe Thr Ile Ser Arg Asp Asn Ser Lys Asn Thr
210 215 220

Leu Tyr Leu Gln Met Asn Ser Leu Arg Ala Glu Asp Thr Ala Val Tyr
225 230 235 240

Tyr Cys Ala Lys Pro Phe Pro Tyr Phe Asp Tyr Trp Gly Gln Gly Thr
245 250 255

Leu Val Thr Val Ser Ser Ser Gly Thr Thr Thr Pro Ala Pro Arg Pro
260 265 270

Pro Thr Pro Ala Pro Thr Ile Ala Ser Gln Pro Leu Ser Leu Arg Pro
275 280 285

Glu Ala Cys Arg Pro Ala Ala Gly Gly Ala Val His Thr Arg Gly Leu
290 295 300

Asp Phe Ala Cys Asp Ile Tyr Ile Trp Ala Pro Leu Ala Gly Thr Cys
305 310 315 320

Gly Val Leu Leu Leu Ser Leu Val Ile Thr Leu Tyr Cys Lys Arg Gly
325 330 335

Arg Lys Lys Leu Leu Tyr Ile Phe Lys Gln Pro Phe Met Arg Pro Val

```
            340                 345                 350

Gln Thr Thr Gln Glu Glu Asp Gly Cys Ser Cys Arg Phe Pro Glu Glu
        355                 360                 365

Glu Glu Gly Gly Cys Glu Leu Arg Val Lys Phe Ser Arg Ser Ala Asp
    370                 375                 380

Ala Pro Ala Tyr Lys Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
            420                 425                 430

Leu Tyr Asn Glu Leu Gln Lys Asp Lys Met Ala Glu Ala Tyr Ser Glu
        435                 440                 445

Ile Gly Met Lys Gly Glu Arg Arg Arg Gly Lys Gly His Asp Gly Leu
    450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485


<210> SEQ ID NO 44
<211> LENGTH: 363
<212> TYPE: DNA
<213> ORGANISM: Artificial Sequence
<220> FEATURE:
<223> OTHER INFORMATION: FDC-6 VH nucleotide sequence

<400> SEQUENCE: 44

caggttactc tgaaagagtc tggccctggg atattgcagc cctcccagac cctcagtctg     60

acttgttctt tctctgggtt ttcactgagc acttctggta tgggtgtagg ctggattcgt    120

cagccttcag ggaagggtct ggagtggctg gcacacattt ggtgggatga taccaggcgc    180

tataacccag ccctgaagag ccgactgaca atctccaatg atacctccaa caaccaggta    240

tttctcaaga tcgccagtgt ggacactgca gatactgcca catactattg tgctcgaatg    300

aacggtaact accctgcctg gtttgcttac tggggccaag ggactctggt cactgtctct    360

tca                                                                   363


<210> SEQ ID NO 45
<211> LENGTH: 336
<212> TYPE: DNA
<213> ORGANISM: Artificial Sequence
<220> FEATURE:
<223> OTHER INFORMATION: FDC-6 VL nucleotide sequence

<400> SEQUENCE: 45

gatgttttga tgacccaaac tccactctcc ctgcctgtca gtcttggaga tcaagcctcc     60

atctcttgca gatctagtca gaacattgta catagtaatg gaaacaccta tttagaatgg    120

tacctgctga aaccaggcca gtctccaaag ctcctgatct acaaagtttc caaccgattt    180

tctggagtcc cagacaggtt cagtggcagt ggatcaggga cagatttcac actcaagatc    240

agcagagtgg aggctgagga tctgggaatt tattactgct ttcaaggttc acatattcct    300

ccgacgttcg gtggaggcac caagctggaa atcaaa                               336


<210> SEQ ID NO 46
<211> LENGTH: 744
<212> TYPE: DNA
```

<213> ORGANISM: Artificial Sequence
<220> FEATURE:
<223> OTHER INFORMATION: FDC-6 scFv (HL) nucleotide sequence

<400> SEQUENCE: 46
caggttactc tgaaagagtc tggccctggg atattgcagc cctcccagac cctcagtctg 60
acttgttctt tctctgggtt ttcactgagc acttctggta tgggtgtagg ctggattcgt 120
cagccttcag ggaagggtct ggagtggctg gcacacattt ggtgggatga taccaggcgc 180
tataacccag ccctgaagag ccgactgaca atctccaatg atacctccaa caaccaggta 240
tttctcaaga tcgccagtgt ggacactgca gatactgcca catactattg tgctcgaatg 300
aacggtaact accctgcctg gtttgcttac tggggccaag ggactctggt cactgtctct 360
tcaggtggcg gagggagcgg cggtggagga agcggaggcg gaggttccga tgttttgatg 420
acccaaactc cactctccct gcctgtcagt cttggagatc aagcctccat ctcttgcaga 480
tctagtcaga acattgtaca tagtaatgga aacacctatt tagaatggta cctgctgaaa 540
ccaggccagt ctccaaagct cctgatctac aaagtttcca accgattttc tggagtccca 600
gacaggttca gtggcagtgg atcagggaca gatttcacac tcaagatcag cagagtggag 660
gctgaggatc tgggaattta ttactgcttt caaggttcac atattcctcc gacgttcggt 720
ggaggcacca agctggaaat caaa 744

<210> SEQ ID NO 47
<211> LENGTH: 744
<212> TYPE: DNA
<213> ORGANISM: Artificial Sequence
<220> FEATURE:
<223> OTHER INFORMATION: FDC-6 scFv (LH) nucleotide sequence

<400> SEQUENCE: 47
gatgttttga tgacccaaac tccactctcc ctgcctgtca gtcttggaga tcaagcctcc 60
atctcttgca gatctagtca gaacattgta catagtaatg gaaacaccta tttagaatgg 120
tacctgctga aaccaggcca gtctccaaag ctcctgatct acaaagtttc caaccgattt 180
tctggagtcc cagacaggtt cagtggcagt ggatcaggga cagatttcac actcaagatc 240
agcagagtgg aggctgagga tctgggaatt tattactgct ttcaaggttc acatattcct 300
ccgacgttcg gtggaggcac caagctggaa atcaaaggtg gcggagggag cggcggtgga 360
ggaagcggag gcggaggttc ccaggttact ctgaaagagt ctggccctgg gatattgcag 420
ccctcccaga ccctcagtct gacttgttct ttctctgggt tttcactgag cacttctggt 480
atgggtgtag gctggattcg tcagccttca gggaagggtc tggagtggct ggcacacatt 540
tggtgggatg ataccaggcg ctataaccca gccctgaaga gccgactgac aatctccaat 600
gatacctcca acaaccaggt atttctcaag atcgccagtg tggacactgc agatactgcc 660
acatactatt gtgctcgaat gaacggtaac taccctgcct ggtttgctta ctggggccaa 720
gggactctgg tcactgtctc ttca 744

<210> SEQ ID NO 48
<211> LENGTH: 1488
<212> TYPE: DNA
<213> ORGANISM: Artificial Sequence
<220> FEATURE:
<223> OTHER INFORMATION: FDC-6 CAR (HL) nucleotide sequence

<400> SEQUENCE: 48
atggccttac cagtgaccgc cttgctcctg ccgctggcct tgctgctcca cgccgccagg 60

```
ccgggatccc aggttactct gaaagagtct ggccctggga tattgcagcc ctcccagacc    120
ctcagtctga cttgttcttt ctctgggttt tcactgagca cttctggtat gggtgtaggc    180
tggattcgtc agccttcagg gaagggtctg gagtggctgg cacacatttg gtgggatgat    240
accaggcgct ataacccagc cctgaagagc cgactgacaa tctccaatga tacctccaac    300
aaccaggtat ttctcaagat cgccagtgtg gacactgcag atactgccac atactattgt    360
gctcgaatga acggtaacta ccctgcctgg tttgcttact ggggccaagg gactctggtc    420
actgtctctt caggtggcgg agggagcggc ggtggaggaa gcggaggcgg aggttccgat    480
gttttgatga cccaaactcc actctccctg cctgtcagtc ttggagatca agcctccatc    540
tcttgcagat ctagtcagaa cattgtacat agtaatggaa acacctattt agaatggtac    600
ctgctgaaac caggccagtc tccaaagctc ctgatctaca aagtttccaa ccgattttct    660
ggagtcccag acaggttcag tggcagtgga tcagggacag atttcacact caagatcagc    720
agagtggagg ctgaggatct gggaatttat tactgctttc aaggttcaca tattcctccg    780
acgttcggtg gaggcaccaa gctggaaatc aaatccggaa ccacgacgcc agcgccgcga    840
ccaccaacac cggcgcccac catcgcgtcg cagcccctgt ccctgcgccc agaggcgtgc    900
cggccagcgg cggggggcgc agtgcacacg agggggctgg acttcgcctg tgatatctac    960
atctgggcgc ccttggccgg gacttgtggg gtccttctcc tgtcactggt tatcaccctt   1020
tactgcaaac ggggcagaaa gaaactcctg tatatattca aacaaccatt tatgagacca   1080
gtacaaacta ctcaagagga agatggctgt agctgccgat ttccagaaga agaagaagga   1140
ggatgtgaac tgagagtgaa gttcagcagg agcgcagacg cccccgcgta caagcagggc   1200
cagaaccagc tctataacga gctcaatcta ggacgaagag aggagtacga tgttttggac   1260
aagagacgtg gccgggaccc tgagatgggg ggaaagccga gaaggaagaa ccctcaggaa   1320
ggcctgtaca atgaactgca gaaagataag atggcggagg cctacagtga gattgggatg   1380
aaaggcgagc gccggagggg caaggggcac gatggccttt accagggtct cagtacagcc   1440
accaaggaca cctacgacgc ccttcacatg caggccctgc cccctcgc                1488
```

```
<210> SEQ ID NO 49
<211> LENGTH: 1488
<212> TYPE: DNA
<213> ORGANISM: Artificial Sequence
<220> FEATURE:
<223> OTHER INFORMATION: FDC-6 CAR (LH) nucleotide sequence

<400> SEQUENCE: 49
```

```
atggccttac cagtgaccgc cttgctcctg ccgctggcct tgctgctcca cgccgccagg     60
ccgggatccg atgttttgat gacccaaact ccactctccc tgcctgtcag tcttggagat    120
caagcctcca tctcttgcag atctagtcag aacattgtac atagtaatgg aaacacctat    180
ttagaatggt acctgctgaa accaggccag tctccaaagc tcctgatcta caaagtttcc    240
aaccgatttt ctggagtccc agacaggttc agtggcagtg gatcagggac agatttcaca    300
ctcaagatca gcagagtgga ggctgaggat ctgggaattt attactgctt tcaaggttca    360
catattcctc cgacgttcgg tggaggcacc aagctggaaa tcaaaggtgg cggagggagc    420
ggcggtggag gaagcggagg cggaggttcc caggttactc tgaaagagtc tggccctggg    480
atattgcagc cctcccagac cctcagtctg acttgttctt tctctgggtt ttcactgagc    540
acttctggta tgggtgtagg ctggattcgt cagccttcag ggaagggtct ggagtggctg    600
```

gcacacattt ggtgggatga taccaggcgc tataacccag ccctgaagag ccgactgaca 660
atctccaatg atacctccaa caaccaggta tttctcaaga tcgccagtgt ggacactgca 720
gatactgcca catactattg tgctcgaatg aacggtaact accctgcctg gtttgcttac 780
tggggccaag ggactctggt cactgtctct tcatccggaa ccacgacgcc agcgccgcga 840
ccaccaacac cggcgcccac catcgcgtcg cagcccctgt ccctgcgccc agaggcgtgc 900
cggccagcgg cggggggcgc agtgcacacg agggggctgg acttcgcctg tgatatctac 960
atctgggcgc ccttggccgg gacttgtggg gtccttctcc tgtcactggt tatcaccctt 1020
tactgcaaac ggggcagaaa gaaactcctg tatatattca aacaaccatt tatgagacca 1080
gtacaaacta ctcaagagga agatggctgt agctgccgat ttccagaaga agaagaagga 1140
ggatgtgaac tgagagtgaa gttcagcagg agcgcagacg cccccgcgta caagcagggc 1200
cagaaccagc tctataacga gctcaatcta ggacgaagag aggagtacga tgttttggac 1260
aagagacgtg gccgggaccc tgagatgggg ggaaagccga gaaggaagaa ccctcaggaa 1320
ggcctgtaca atgaactgca gaaagataag atggcggagg cctacagtga gattgggatg 1380
aaaggcgagc gccggagggg caaggggcac gatggccttt accagggtct cagtacagcc 1440
accaaggaca cctacgacgc ccttcacatg caggccctgc cccctcgc 1488

<210> SEQ ID NO 50
<211> LENGTH: 369
<212> TYPE: DNA
<213> ORGANISM: Artificial Sequence
<220> FEATURE:
<223> OTHER INFORMATION: C6 VH nucleotide sequence

<400> SEQUENCE: 50
gaggtccaat tggtagagag tggcggcggc ctcgtccagc caaaaggttc cttgaagata 60
agctgtgccg catcaggact gacgttcaac acctatgcca tgaactgggt ccggcaggca 120
ccacgcaagg gccttgagtg ggtcgcaaga ataaggtcta agtccaataa ctacgcgact 180
tactacgcgg atagtgtaaa ggatcgcttc acaatatcac gcgacgactc acaatcaatg 240
ttgtatctcc agatgaataa ccttaagaca gaggacactg ctatgtatta ttgcgtgaag 300
caaggcggga actcacttta ttggtacttt gatgtctggg gcgcgggcac gacggtcacc 360
gtttcttcc 369

<210> SEQ ID NO 51
<211> LENGTH: 339
<212> TYPE: DNA
<213> ORGANISM: Artificial Sequence
<220> FEATURE:
<223> OTHER INFORMATION: C6 VL nucleotide sequence

<400> SEQUENCE: 51
gatatagtga tgagtcagag tccaagctcc ttggcggtga gtgtcgggga gaaggtcact 60
atgagctgca agtccagtca atccttgctc tattcttcta accaaaaaaa ttatttggcc 120
tggtatcaac aaagacctgg tcagtctccc aaacttttga tatattgggc atctaccggc 180
gaatctggcg ttcctgacag gtttaccggg agtgggtcag gaactgactt cactctcacg 240
atctctagtg tcaaagccga agatttggcc gtctattact gtcagcaata ttactcctat 300
cctctgacct ttggcgctgg cacaaagttg gagcttaag 339

<210> SEQ ID NO 52
<211> LENGTH: 762

<212> TYPE: DNA
<213> ORGANISM: Artificial Sequence
<220> FEATURE:
<223> OTHER INFORMATION: C6 scFv (HL) nucleotide sequence

<400> SEQUENCE: 52
gaggtccaat tggtagagag tggcggcggc ctcgtccagc caaaaggttc cttgaagata 60
agctgtgccg catcaggact gacgttcaac acctatgcca tgaactgggt ccggcaggca 120
ccacgcaagg gccttgagtg ggtcgcaaga ataaggtcta agtccaataa ctacgcgact 180
tactacgcgg atagtgtaaa ggatcgcttc acaatatcac gcgacgactc acaatcaatg 240
ttgtatctcc agatgaataa ccttaagaca gaggacactg ctatgtatta ttgcgtgaag 300
caaggcggga actcacttta ttggtacttt gatgtctggg gcgcgggcac gacggtcacc 360
gtttcttccg gcagtacctc agggtccggc aagccaggta gtggcgaggg cagcagtaag 420
ggagatatag tgatgagtca gagtccaagc tccttggcgg tgagtgtcgg ggagaaggtc 480
actatgagct gcaagtccag tcaatccttg ctctattctt ctaaccaaaa aaattatttg 540
gcctggtatc aacaaagacc tggtcagtct cccaaacttt tgatatattg ggcatctacc 600
ggcgaatctg gcgttcctga caggtttacc gggagtgggt caggaactga cttcactctc 660
acgatctcta gtgtcaaagc cgaagatttg gccgtctatt actgtcagca atattactcc 720
tatcctctga cctttggcgc tggcacaaag ttggagctta ag 762

<210> SEQ ID NO 53
<211> LENGTH: 762
<212> TYPE: DNA
<213> ORGANISM: Artificial Sequence
<220> FEATURE:
<223> OTHER INFORMATION: C6 scFv (LH) nucleotide sequence

<400> SEQUENCE: 53
gatatagtga tgagtcagag tccaagctcc ttggcggtga gtgtcgggga gaaggtcact 60
atgagctgca agtccagtca atccttgctc tattcttcta accaaaaaaa ttatttggcc 120
tggtatcaac aaagacctgg tcagtctccc aaacttttga tatattgggc atctaccggc 180
gaatctggcg ttcctgacag gtttaccggg agtgggtcag gaactgactt cactctcacg 240
atctctagtg tcaaagccga agatttggcc gtctattact gtcagcaata ttactcctat 300
cctctgacct ttggcgctgg cacaaagttg gagcttaagg gcagtacctc agggtccggc 360
aagccaggta gtggcgaggg cagcagtaag ggagaggtcc aattggtaga gagtggcggc 420
ggcctcgtcc agccaaaagg ttccttgaag ataagctgtg ccgcatcagg actgacgttc 480
aacacctatg ccatgaactg ggtccggcag gcaccacgca agggccttga gtgggtcgca 540
agaataaggt ctaagtccaa taactacgcg acttactacg cggatagtgt aaaggatcgc 600
ttcacaatat cacgcgacga ctcacaatca atgttgtatc tccagatgaa taaccttaag 660
acagaggaca ctgctatgta ttattgcgtg aagcaaggcg ggaactcact ttattggtac 720
tttgatgtct ggggcgcggg cacgacggtc accgtttctt cc 762

<210> SEQ ID NO 54
<211> LENGTH: 1506
<212> TYPE: DNA
<213> ORGANISM: Artificial Sequence
<220> FEATURE:
<223> OTHER INFORMATION: C6 CAR (HL) nucleotide sequence

<400> SEQUENCE: 54

```
atggccttac cagtgaccgc cttgctcctg ccgctggcct tgctgctcca cgccgccagg     60

ccgggatccg aggtccaatt ggtagagagt ggcggcggcc tcgtccagcc aaaaggttcc    120

ttgaagataa gctgtgccgc atcaggactg acgttcaaca cctatgccat gaactgggtc    180

cggcaggcac cacgcaaggg ccttgagtgg gtcgcaagaa taaggtctaa gtccaataac    240

tacgcgactt actacgcgga tagtgtaaag gatcgcttca caatatcacg cgacgactca    300

caatcaatgt tgtatctcca gatgaataac cttaagacag aggacactgc tatgtattat    360

tgcgtgaagc aaggcgggaa ctcactttat tggtactttg atgtctgggg cgcgggcacg    420

acggtcaccg tttcttccgg cagtacctca gggtccggca agccaggtag tggcgagggc    480

agcagtaagg gagatatagt gatgagtcag agtccaagct ccttggcggt gagtgtcggg    540

gagaaggtca ctatgagctg caagtccagt caatccttgc tctattcttc taaccaaaaa    600

aattatttgg cctggtatca acaaagacct ggtcagtctc ccaaactttt gatatattgg    660

gcatctaccg gcgaatctgg cgttcctgac aggtttaccg ggagtgggtc aggaactgac    720

ttcactctca cgatctctag tgtcaaagcc gaagatttgg ccgtctatta ctgtcagcaa    780

tattactcct atcctctgac ctttggcgct ggcacaaagt tggagcttaa gtccggaacc    840

acgacgccag cgccgcgacc accaacaccg gcgcccacca tcgcgtcgca gcccctgtcc    900

ctgcgcccag aggcgtgccg gccagcggcg gggggcgcag tgcacacgag ggggctggac    960

ttcgcctgtg atatctacat ctgggcgccc ttggccggga cttgtggggt ccttctcctg   1020

tcactggtta tcacccttta ctgcaaacgg ggcagaaaga aactcctgta tatattcaaa   1080

caaccattta tgagaccagt acaaactact caagaggaag atggctgtag ctgccgattt   1140

ccagaagaag aagaaggagg atgtgaactg agagtgaagt tcagcaggag cgcagacgcc   1200

cccgcgtaca agcagggcca gaaccagctc tataacgagc tcaatctagg acgaagagag   1260

gagtacgatg ttttggacaa gagacgtggc cgggaccctg agatgggggg aaagccgaga   1320

aggaagaacc ctcaggaagg cctgtacaat gaactgcaga aagataagat ggcggaggcc   1380

tacagtgaga ttgggatgaa aggcgagcgc cggaggggca aggggcacga tggcctttac   1440

cagggtctca gtacagccac caaggacacc tacgacgccc ttcacatgca ggccctgccc   1500

cctcgc                                                              1506
```

<210> SEQ ID NO 55
<211> LENGTH: 1506
<212> TYPE: DNA
<213> ORGANISM: Artificial Sequence
<220> FEATURE:
<223> OTHER INFORMATION: C6 CAR (LH) nucleotide sequence

<400> SEQUENCE: 55

```
atggccttac cagtgaccgc cttgctcctg ccgctggcct tgctgctcca cgccgccagg     60

ccgggatccg atatagtgat gagtcagagt ccaagctcct tggcggtgag tgtcggggag    120

aaggtcacta tgagctgcaa gtccagtcaa tccttgctct attcttctaa ccaaaaaaat    180

tatttggcct ggtatcaaca aagacctggt cagtctccca aacttttgat atattgggca    240

tctaccggcg aatctggcgt tcctgacagg tttaccggga gtgggtcagg aactgacttc    300

actctcacga tctctagtgt caaagccgaa gatttggccg tctattactg tcagcaatat    360

tactcctatc ctctgacctt tggcgctggc acaaagttgg agcttaaggg cagtacctca    420

gggtccggca agccaggtag tggcgagggc agcagtaagg gagaggtcca attggtagag    480

agtggcggcg gcctcgtcca gccaaaaggt tccttgaaga taagctgtgc cgcatcagga    540
```

ctgacgttca acacctatgc catgaactgg gtccggcagg caccacgcaa gggccttgag 600
tgggtcgcaa gaataaggtc taagtccaat aactacgcga cttactacgc ggatagtgta 660
aaggatcgct tcacaatatc acgcgacgac tcacaatcaa tgttgtatct ccagatgaat 720
aaccttaaga cagaggacac tgctatgtat tattgcgtga agcaaggcgg gaactcactt 780
tattggtact ttgatgtctg gggcgcgggc acgacggtca ccgtttcttc ctccggaacc 840
acgacgccag cgccgcgacc accaacaccg gcgcccacca tcgcgtcgca gcccctgtcc 900
ctgcgcccag aggcgtgccg gccagcggcg gggggcgcag tgcacacgag ggggctggac 960
ttcgcctgtg atatctacat ctgggcgccc ttggccggga cttgtggggt ccttctcctg 1020
tcactggtta tcacccttta ctgcaaacgg ggcagaaaga aactcctgta tatattcaaa 1080
caaccattta tgagaccagt acaaactact caagaggaag atggctgtag ctgccgattt 1140
ccagaagaag aagaaggagg atgtgaactg agagtgaagt tcagcaggag cgcagacgcc 1200
cccgcgtaca agcagggcca gaaccagctc tataacgagc tcaatctagg acgaagagag 1260
gagtacgatg ttttggacaa gagacgtggc cgggaccctg agatgggggg aaagccgaga 1320
aggaagaacc ctcaggaagg cctgtacaat gaactgcaga aagataagat ggcggaggcc 1380
tacagtgaga ttgggatgaa aggcgagcgc cggaggggca aggggcacga tggcctttac 1440
cagggtctca gtacagccac caaggacacc tacgacgccc ttcacatgca ggccctgccc 1500
cctcgc 1506

<210> SEQ ID NO 56
<211> LENGTH: 348
<212> TYPE: DNA
<213> ORGANISM: Artificial Sequence
<220> FEATURE:
<223> OTHER INFORMATION: L19 VH nucleotide sequence

<400> SEQUENCE: 56
gaggtacagc tcttggagtc tgggggtggt ttggttcaac caggtggctc tctgcgcctg 60
tcctgtgcgg cttctggttt taccttctct tcattctcta tgtcctgggt tcgacaggca 120
cctggaaagg gactggagtg ggtttcctct ataagcggca gttctggcac gacgtattat 180
gccgactccg tcaagggaag gttcaccatt tctcgggata attcaaagaa cacactctac 240
ttgcagatga actcattgag agcagaagac acagcagtgt actattgtgc gaagcccttt 300
ccgtatttcg attactgggg ccagggcaca ttggttactg ttagcagt 348

<210> SEQ ID NO 57
<211> LENGTH: 324
<212> TYPE: DNA
<213> ORGANISM: Artificial Sequence
<220> FEATURE:
<223> OTHER INFORMATION: L19 VL nucleotide sequence

<400> SEQUENCE: 57
gagatcgttt tgacacaatc tccgggcaca ctctctctca gtccaggcga acgcgcaact 60
ttgtcttgtc gagccagcca gagcgtttcc tcctcattcc ttgcgtggta tcagcagaag 120
ccgggccagg caccccgcct cctgatttac tacgcatcat ctagggcaac aggtattcct 180
gacaggttca gtggctcagg ctctggcaca gattttacac tcactatttc cagattggag 240
ccagaggatt ttgcggttta ctattgccag caaactgggc gaatcccacc gacattcgga 300
caaggtacga aggtcgaaat caag 324

<210> SEQ ID NO 58
<211> LENGTH: 717
<212> TYPE: DNA
<213> ORGANISM: Artificial Sequence
<220> FEATURE:
<223> OTHER INFORMATION: L19 scFv (HL) nucleotide sequence

<400> SEQUENCE: 58
gaggtacagc tcttggagtc tgggggtggt ttggttcaac caggtggctc tctgcgcctg 60
tcctgtgcgg cttctggttt taccttctct tcattctcta tgtcctgggt tcgacaggca 120
cctggaaagg gactggagtg ggtttcctct ataagcggca gttctggcac gacgtattat 180
gccgactccg tcaagggaag gttcaccatt tctcgggata attcaaagaa cacactctac 240
ttgcagatga actcattgag agcagaagac acagcagtgt actattgtgc gaagcccttt 300
ccgtatttcg attactgggg ccagggcaca ttggttactg ttagcagtgg tggcggaggg 360
agcggcggtg gaggaagcgg aggcggaggt tccgagatcg ttttgacaca atctccgggc 420
acactctctc tcagtccagg cgaacgcgca actttgtctt gtcgagccag ccagagcgtt 480
tcctcctcat tccttgcgtg gtatcagcag aagccgggcc aggcaccccg cctcctgatt 540
tactacgcat catctagggc aacaggtatt cctgacaggt tcagtggctc aggctctggc 600
acagatttta cactcactat ttccagattg gagccagagg attttgcggt ttactattgc 660
cagcaaactg ggcgaatccc accgacattc ggacaaggta cgaaggtcga aatcaag 717

<210> SEQ ID NO 59
<211> LENGTH: 717
<212> TYPE: DNA
<213> ORGANISM: Artificial Sequence
<220> FEATURE:
<223> OTHER INFORMATION: L19 scFv (LH) nucleotide sequence

<400> SEQUENCE: 59
gagatcgttt tgacacaatc tccgggcaca ctctctctca gtccaggcga acgcgcaact 60
ttgtcttgtc gagccagcca gagcgtttcc tcctcattcc ttgcgtggta tcagcagaag 120
ccgggccagg caccccgcct cctgatttac tacgcatcat ctagggcaac aggtattcct 180
gacaggttca gtggctcagg ctctggcaca gattttacac tcactatttc cagattggag 240
ccagaggatt ttgcggttta ctattgccag caaactgggc gaatcccacc gacattcgga 300
caaggtacga aggtcgaaat caagggtggc ggagggagcg gcggtggagg aagcggaggc 360
ggaggttccg aggtacagct cttggagtct gggggtggtt tggttcaacc aggtggctct 420
ctgcgcctgt cctgtgcggc ttctggtttt accttctctt cattctctat gtcctgggtt 480
cgacaggcac ctggaaaggg actggagtgg gtttcctcta taagcggcag ttctggcacg 540
acgtattatg ccgactccgt caagggaagg ttcaccattt ctcgggataa ttcaaagaac 600
acactctact tgcagatgaa ctcattgaga gcagaagaca cagcagtgta ctattgtgcg 660
aagccctttc cgtatttcga ttactggggc cagggcacat tggttactgt tagcagt 717

<210> SEQ ID NO 60
<211> LENGTH: 1461
<212> TYPE: DNA
<213> ORGANISM: Artificial Sequence
<220> FEATURE:
<223> OTHER INFORMATION: L19 CAR (HL) nucleotide sequence

<400> SEQUENCE: 60
atggccttac cagtgaccgc cttgctcctg ccgctggcct tgctgctcca cgccgccagg 60

```
ccgggatccg aggtacagct cttggagtct gggggtggtt tggttcaacc aggtggctct    120
ctgcgcctgt cctgtgcggc ttctggtttt accttctctt cattctctat gtcctgggtt    180
cgacaggcac ctggaaaggg actggagtgg gtttcctcta taagcggcag ttctggcacg    240
acgtattatg ccgactccgt caagggaagg ttcaccattt ctcgggataa ttcaaagaac    300
acactctact tgcagatgaa ctcattgaga gcagaagaca cagcagtgta ctattgtgcg    360
aagccctttc cgtatttcga ttactggggc cagggcacat tggttactgt tagcagtggt    420
ggcggaggga gcggcggtgg aggaagcgga ggcggaggtt ccgagatcgt tttgacacaa    480
tctccgggca cactctctct cagtccaggc gaacgcgcaa ctttgtcttg tcgagccagc    540
cagagcgttt cctcctcatt ccttgcgtgg tatcagcaga agccgggcca ggcaccccgc    600
ctcctgattt actacgcatc atctagggca acaggtattc ctgacaggtt cagtggctca    660
ggctctggca cagattttac actcactatt tccagattgg agccagagga ttttgcggtt    720
tactattgcc agcaaactgg gcgaatccca ccgacattcg gacaaggtac gaaggtcgaa    780
atcaagtccg gaaccacgac gccagcgccg cgaccaccaa caccggcgcc caccatcgcg    840
tcgcagcccc tgtccctgcg cccagaggcg tgccggccag cggcgggggg cgcagtgcac    900
acgagggggc tggacttcgc ctgtgatatc tacatctggg cgcccttggc cgggacttgt    960
ggggtccttc tcctgtcact ggttatcacc ctttactgca aacggggcag aaagaaactc   1020
ctgtatatat tcaaacaacc atttatgaga ccagtacaaa ctactcaaga ggaagatggc   1080
tgtagctgcc gatttccaga agaagaagaa ggaggatgtg aactgagagt gaagttcagc   1140
aggagcgcag acgcccccgc gtacaagcag ggccagaacc agctctataa cgagctcaat   1200
ctaggacgaa gagaggagta cgatgttttg gacaagagac gtggccggga ccctgagatg   1260
gggggaaagc cgagaaggaa gaaccctcag gaaggcctgt acaatgaact gcagaaagat   1320
aagatggcgg aggcctacag tgagattggg atgaaaggcg agcgccggag gggcaagggg   1380
cacgatggcc tttaccaggg tctcagtaca gccaccaagg acacctacga cgcccttcac   1440
atgcaggccc tgccccctcg c                                             1461
```

<210> SEQ ID NO 61
<211> LENGTH: 1461
<212> TYPE: DNA
<213> ORGANISM: Artificial Sequence
<220> FEATURE:
<223> OTHER INFORMATION: L19 CAR (LH) nucleotide sequence

<400> SEQUENCE: 61

```
atggccttac cagtgaccgc cttgctcctg ccgctggcct tgctgctcca cgccgccagg     60
ccgggatccg agatcgtttt gacacaatct ccgggcacac tctctctcag tccaggcgaa    120
cgcgcaactt tgtcttgtcg agccagccag agcgtttcct cctcattcct tgcgtggtat    180
cagcagaagc cgggccaggc accccgcctc ctgatttact acgcatcatc tagggcaaca    240
ggtattcctg acaggttcag tggctcaggc tctggcacag attttacact cactatttcc    300
agattggagc cagaggattt tgcggtttac tattgccagc aaactgggcg aatcccaccg    360
acattcggac aaggtacgaa ggtcgaaatc aagggtggcg gagggagcgg cggtggagga    420
agcggaggcg gaggttccga ggtacagctc ttggagtctg gggggtggttt ggttcaacca    480
ggtggctctc tgcgcctgtc ctgtgcggct tctggtttta ccttctcttc attctctatg    540
tcctgggttc gacaggcacc tggaaaggga ctggagtggg tttcctctat aagcggcagt    600
```

```
tctggcacga cgtattatgc cgactccgtc aagggaaggt tcaccatttc tcgggataat    660

tcaaagaaca cactctactt gcagatgaac tcattgagag cagaagacac agcagtgtac    720

tattgtgcga agccctttcc gtatttcgat tactggggcc agggcacatt ggttactgtt    780

agcagttccg gaaccacgac gccagcgccg cgaccaccaa caccggcgcc caccatcgcg    840

tcgcagcccc tgtccctgcg cccagaggcg tgccggccag cggcgggggg cgcagtgcac    900

acgagggggc tggacttcgc ctgtgatatc tacatctggg cgcccttggc cgggacttgt    960

ggggtccttc tcctgtcact ggttatcacc ctttactgca aacggggcag aaagaaactc   1020

ctgtatatat tcaaacaacc atttatgaga ccagtacaaa ctactcaaga ggaagatggc   1080

tgtagctgcc gatttccaga agaagaagaa ggaggatgtg aactgagagt gaagttcagc   1140

aggagcgcag acgcccccgc gtacaagcag ggccagaacc agctctataa cgagctcaat   1200

ctaggacgaa gagaggagta cgatgttttg gacaagagac gtggccggga ccctgagatg   1260

gggggaaagc cgagaaggaa gaaccctcag gaaggcctgt acaatgaact gcagaaagat   1320

aagatggcgg aggcctacag tgagattggg atgaaaggcg agcgccggag gggcaagggg   1380

cacgatggcc tttaccaggg tctcagtaca gccaccaagg acacctacga cgcccttcac   1440

atgcaggccc tgccccctcg c                                             1461


<210> SEQ ID NO 62
<211> LENGTH: 5
<212> TYPE: PRT
<213> ORGANISM: Artificial Sequence
<220> FEATURE:
<223> OTHER INFORMATION: GS Linker
<220> FEATURE:
<221> NAME/KEY: REPEAT
<222> LOCATION: (1)..(5)
<223> OTHER INFORMATION: Sequence repeats N times, where N = an integer
      of at least 1.

<400> SEQUENCE: 62

Gly Ser Gly Gly Ser
1               5


<210> SEQ ID NO 63
<211> LENGTH: 4
<212> TYPE: PRT
<213> ORGANISM: Artificial Sequence
<220> FEATURE:
<223> OTHER INFORMATION: GS Linker
<220> FEATURE:
<221> NAME/KEY: REPEAT
<222> LOCATION: (1)..(4)
<223> OTHER INFORMATION: Sequence repeats N times, where N = an integer
      of at least 1.

<400> SEQUENCE: 63

Gly Gly Gly Ser
1


<210> SEQ ID NO 64
<211> LENGTH: 5
<212> TYPE: PRT
<213> ORGANISM: Artificial Sequence
<220> FEATURE:
<223> OTHER INFORMATION: GS Linker
<220> FEATURE:
<221> NAME/KEY: REPEAT
<222> LOCATION: (1)..(5)
<223> OTHER INFORMATION: Sequence repeats N times, where N = an integer
      of at least 1.
```

<400> SEQUENCE: 64

Gly Gly Gly Gly Ser
1               5

<210> SEQ ID NO 65
<211> LENGTH: 4
<212> TYPE: PRT
<213> ORGANISM: Artificial Sequence
<220> FEATURE:
<223> OTHER INFORMATION: GS Linker

<400> SEQUENCE: 65

Gly Gly Ser Gly
1

<210> SEQ ID NO 66
<211> LENGTH: 5
<212> TYPE: PRT
<213> ORGANISM: Artificial Sequence
<220> FEATURE:
<223> OTHER INFORMATION: GS Linker

<400> SEQUENCE: 66

Gly Gly Ser Gly Gly
1               5

<210> SEQ ID NO 67
<211> LENGTH: 5
<212> TYPE: PRT
<213> ORGANISM: Artificial Sequence
<220> FEATURE:
<223> OTHER INFORMATION: GS Linker

<400> SEQUENCE: 67

Gly Ser Gly Ser Gly
1               5

<210> SEQ ID NO 68
<211> LENGTH: 5
<212> TYPE: PRT
<213> ORGANISM: Artificial Sequence
<220> FEATURE:
<223> OTHER INFORMATION: GS Linker

<400> SEQUENCE: 68

Gly Ser Gly Gly Gly
1               5

<210> SEQ ID NO 69
<211> LENGTH: 5
<212> TYPE: PRT
<213> ORGANISM: Artificial Sequence
<220> FEATURE:
<223> OTHER INFORMATION: GS Linker

<400> SEQUENCE: 69

Gly Gly Gly Ser Gly
1               5

<210> SEQ ID NO 70
<211> LENGTH: 5
<212> TYPE: PRT
<213> ORGANISM: Artificial Sequence
<220> FEATURE:
<223> OTHER INFORMATION: GS Linker

<400> SEQUENCE: 70

Gly Ser Ser Ser Gly
1 5

<210> SEQ ID NO 71
<211> LENGTH: 5
<212> TYPE: PRT
<213> ORGANISM: Artificial Sequence
<220> FEATURE:
<223> OTHER INFORMATION: GS Linker

<400> SEQUENCE: 71

Gly Gly Gly Gly Ser
1 5

<210> SEQ ID NO 72
<211> LENGTH: 15
<212> TYPE: PRT
<213> ORGANISM: Artificial Sequence
<220> FEATURE:
<223> OTHER INFORMATION: GS Linker

<400> SEQUENCE: 72

Gly Gly Gly Gly Ser Gly Gly Gly Gly Ser Gly Gly Gly Gly Ser
1 5 10 15

<210> SEQ ID NO 73
<211> LENGTH: 45
<212> TYPE: DNA
<213> ORGANISM: Artificial Sequence
<220> FEATURE:
<223> OTHER INFORMATION: GS Linker Nuceotide

<400> SEQUENCE: 73
ggtggcggtg gctcgggcgg tggtgggtcg ggtggcggcg gatct 45

<210> SEQ ID NO 74
<211> LENGTH: 5
<212> TYPE: PRT
<213> ORGANISM: Artificial Sequence
<220> FEATURE:
<223> OTHER INFORMATION: Hinge

<400> SEQUENCE: 74

Asp Lys Thr His Thr
1 5

<210> SEQ ID NO 75
<211> LENGTH: 4
<212> TYPE: PRT
<213> ORGANISM: Artificial Sequence
<220> FEATURE:
<223> OTHER INFORMATION: Hinge

<400> SEQUENCE: 75

Cys Pro Pro Cys
1

<210> SEQ ID NO 76
<211> LENGTH: 15
<212> TYPE: PRT
<213> ORGANISM: Artificial Sequence
<220> FEATURE:
<223> OTHER INFORMATION: Hinge

<400> SEQUENCE: 76

Cys Pro Glu Pro Lys Ser Cys Asp Thr Pro Pro Pro Cys Pro Arg 1 5 10 15

<210> SEQ ID NO 77
<211> LENGTH: 12
<212> TYPE: PRT
<213> ORGANISM: Artificial Sequence
<220> FEATURE:
<223> OTHER INFORMATION: Hinge

<400> SEQUENCE: 77

Glu Leu Lys Thr Pro Leu Gly Asp Thr Thr His Thr
1 5 10

<210> SEQ ID NO 78
<211> LENGTH: 10
<212> TYPE: PRT
<213> ORGANISM: Artificial Sequence
<220> FEATURE:
<223> OTHER INFORMATION: Hinge

<400> SEQUENCE: 78

Lys Ser Cys Asp Lys Thr His Thr Cys Pro
1 5 10

<210> SEQ ID NO 79
<211> LENGTH: 7
<212> TYPE: PRT
<213> ORGANISM: Artificial Sequence
<220> FEATURE:
<223> OTHER INFORMATION: Hinge

<400> SEQUENCE: 79

Lys Cys Cys Val Asp Cys Pro
1 5

<210> SEQ ID NO 80
<211> LENGTH: 7
<212> TYPE: PRT
<213> ORGANISM: Artificial Sequence
<220> FEATURE:
<223> OTHER INFORMATION: Hinge

<400> SEQUENCE: 80

Lys Tyr Gly Pro Pro Cys Pro
1 5

<210> SEQ ID NO 81
<211> LENGTH: 15
<212> TYPE: PRT
<213> ORGANISM: Artificial Sequence
<220> FEATURE:
<223> OTHER INFORMATION: Hinge

<400> SEQUENCE: 81

Glu Pro Lys Ser Cys Asp Lys Thr His Thr Cys Pro Pro Cys Pro
1 5 10 15

<210> SEQ ID NO 82
<211> LENGTH: 12
<212> TYPE: PRT
<213> ORGANISM: Artificial Sequence
<220> FEATURE:
<223> OTHER INFORMATION: Hinge

<400> SEQUENCE: 82

Glu Arg Lys Cys Cys Val Glu Cys Pro Pro Cys Pro
1 5 10

```
<210> SEQ ID NO 83
<211> LENGTH: 17
<212> TYPE: PRT
<213> ORGANISM: Artificial Sequence
<220> FEATURE:
<223> OTHER INFORMATION: Hinge

<400> SEQUENCE: 83

Glu Leu Lys Thr Pro Leu Gly Asp Thr Thr His Thr Cys Pro Arg Cys
1               5                   10                  15

Pro


<210> SEQ ID NO 84
<211> LENGTH: 12
<212> TYPE: PRT
<213> ORGANISM: Artificial Sequence
<220> FEATURE:
<223> OTHER INFORMATION: Hinge

<400> SEQUENCE: 84

Ser Pro Asn Met Val Pro His Ala His His Ala Gln
1               5                   10


<210> SEQ ID NO 85
<211> LENGTH: 15
<212> TYPE: PRT
<213> ORGANISM: Artificial Sequence
<220> FEATURE:
<223> OTHER INFORMATION: Hinge

<400> SEQUENCE: 85

Glu Pro Lys Ser Cys Asp Lys Thr Tyr Thr Cys Pro Pro Cys Pro
1               5                   10                  15
```

FIBRONECTIN TARGETING CHIMERIC ANTIGEN RECEPTORS (CARs)

CROSS-REFERENCE TO RELATED APPLICATION

The present application is a 35 U.S.C. § 371 national phase application of, and claims priority to, International Application No. PCT/US2020/058352, filed Oct. 30, 2020, which is entitled to priority under 35 U.S.C. § 119 (e) to U.S. Provisional Patent Application No. 62/929,575 filed Nov. 1, 2019, all of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Apr. 27, 2022, is named 046483-7284US1_SequenceListing_ST25.txt and is 79 kilobytes in size.

BACKGROUND OF THE INVENTION

Current immunotherapy advances have been revolutionary for the treatment of hematologic malignancies as evident by the FDA approvals of CD19-targeting CAR-T cells for the treatment of acute lymphoblastic leukemia and diffuse-large B-cell lymphoma. However, the greatest unmet burden for cancer treatment is solid tumors, particularly prostate, breast, colorectal, and lung cancers, which account for approximately 45% of all cancer related deaths in the United States. CAR-T cells have lacked efficacy in the fight against solid tumors due to a number of challenges, including the lack of tumor-specific antigens, overcoming obstacles of therapeutic resistance, tumor heterogeneity, poor expansion and persistence, and extrinsic dysfunction and physical barriers to T cell infiltration caused by the dense, immunosuppressive tumor microenvironment (TME). There is a need in the art for novel CAR-T cell therapies that overcome these obstacles and challenges. The present invention addresses this need.

SUMMARY OF THE INVENTION

As described herein, the present invention relates to chimeric antigen receptors (CARs) targeting onco-fetal variants of fibronectin expressed in the extracellular matrix of solid tumors. Also included are nucleic acids and vectors comprising the CAR and methods of using the same.

In one aspect, the invention includes a chimeric antigen receptor (CAR) comprising an antigen binding domain capable of binding the IIICS domain of fibronectin, a transmembrane domain, and an intracellular domain.

In certain embodiments, the antigen binding domain comprises at least one heavy chain variable region (HCDR) comprising the nucleotide sequence selected from the group consisting of SEQ ID NO: 1, SEQ ID NO: 2, and SEQ ID NO: 3.

In certain embodiments, the antigen binding domain comprises at least one light chain variable region (LCDR) comprising the nucleotide sequence selected from the group consisting of SEQ ID NO: 4, SEQ ID NO: 5, and SEQ ID NO: 6.

In certain embodiments, the antigen binding domain comprises a heavy chain variable region comprising an amino acid sequence at least 80%, 85%, 90%, 95%, 96%, 97%, 98%, 99%, or 100% identical to SEQ ID NO: 7.

In certain embodiments, the antigen binding domain comprises a light chain variable region comprising an amino acid sequence at least 80%, 85%, 90%, 95%, 96%, 97%, 98%, 99%, or 100% identical to SEQ ID NO: 8.

In certain embodiments, the antigen binding domain is a single-chain variable fragment (scFv) comprising an amino acid sequence at least 80%, 85%, 90%, 95%, 96%, 97%, 98%, 99%, or 100% identical to SEQ ID NO: 10 or SEQ ID NO: 11.

In another aspect, the invention includes a chimeric antigen receptor (CAR) comprising an antigen binding domain capable of binding the EDB domain of fibronectin, a transmembrane domain, and an intracellular domain.

In certain embodiments, the antigen binding domain comprises at least one heavy chain variable region (HCDR) comprising the nucleotide sequence selected from the group consisting of SEQ ID NO: 12, SEQ ID NO: 13, and SEQ ID NO: 14.

In certain embodiments, the antigen binding domain comprises at least one light chain variable region (LCDR) comprising the nucleotide sequence selected from the group consisting of SEQ ID NO: 15, SEQ ID NO: 16, and SEQ ID NO: 17.

In certain embodiments, the antigen binding domain comprises a heavy chain variable region comprising an amino acid sequence at least 80%, 85%, 90%, 95%, 96%, 97%, 98%, 99%, or 100% identical to SEQ ID NO: 18.

In certain embodiments, the antigen binding domain comprises a light chain variable region comprising an amino acid sequence at least 80%, 85%, 90%, 95%, 96%, 97%, 98%, 99%, or 100% identical to SEQ ID NO: 19.

In certain embodiments, the antigen binding domain comprises at least one heavy chain variable region (HCDR) comprising the nucleotide sequence selected from the group consisting of SEQ ID NO: 23, SEQ ID NO: 24, and SEQ ID NO: 25.

In certain embodiments, the antigen binding domain comprises at least one light chain variable region (LCDR) comprising the nucleotide sequence selected from the group consisting of SEQ ID NO: 26, SEQ ID NO: 27, and SEQ ID NO: 28.

In certain embodiments, the antigen binding domain comprises a heavy chain variable region comprising an amino acid sequence at least 80%, 85%, 90%, 95%, 96%, 97%, 98%, 99%, or 100% identical to SEQ ID NO: 29.

In certain embodiments, the antigen binding domain comprises a light chain variable region comprising an amino acid sequence at least 80%, 85%, 90%, 95%, 96%, 97%, 98%, 99%, or 100% identical to SEQ ID NO: 30.

In certain embodiments, the antigen binding domain is a single-chain variable fragment (scFv) comprising an amino acid sequence at least 80%, 85%, 90%, 95%, 96%, 97%, 98%, 99%, or 100% identical to SEQ ID NO: 31 or SEQ ID NO: 32.

In certain embodiments, the antigen binding domain is selected from the group consisting of a full length antibody or antigen-binding fragment thereof, a Fab, a single-chain variable fragment (scFv), or a single-domain antibody.

In certain embodiments, the CAR further comprises a CD8 alpha hinge sequence comprising the amino acid sequence set forth in SEQ ID NO: 34.

In certain embodiments, the transmembrane domain comprises a transmembrane domain selected from the group consisting of an artificial hydrophobic sequence, and a transmembrane domain of a type I transmembrane protein, an alpha, beta, or zeta chain of a T cell receptor, CD28, CD3 epsilon, CD45, CD4, CD5, CD8, CD9, CD16, CD22, CD33, CD37, CD64, CD80, CD86, OX40 (CD134), 4-1BB (CD137), ICOS, and CD154, or a transmembrane domain derived from a killer immunoglobulin-like receptor (KIR).

In certain embodiments, the transmembrane domain comprises a transmembrane domain of CD8 alpha comprising the amino acid sequence set forth in SEQ ID NO: 35.

In certain embodiments, the intracellular domain comprises a costimulatory signaling domain and an intracellular signaling domain.

In certain embodiments, the intracellular domain comprises a costimulatory domain of a protein selected from the group consisting of proteins in the TNFR superfamily, CD28, 4-1BB (CD137), OX40 (CD134), PD-1, CD7, LIGHT, CD83L, DAP10, DAP12, CD27, CD2, CDS, ICAM-1, LFA-1, Lck, TNFR-I, TNFR-II, Fas, CD30, CD40, ICOS, NKG2C, and B7-H3 (CD276), or a variant thereof, or an intracellular domain derived from a killer immunoglobulin-like receptor (KIR).

In certain embodiments, the intracellular domain comprises a costimulatory domain of 4-1BB.

In certain embodiments, the costimulatory domain of 4-1BB comprises the amino acid sequence set forth in SEQ ID NO: 36.

In certain embodiments, intracellular signaling domain comprises an intracellular domain selected from the group consisting of cytoplasmic signaling domains of a human CD3 zeta chain (CD3), FcγRIII, FcsRI, a cytoplasmic tail of an Fc receptor, an immunoreceptor tyrosine-based activation motif (ITAM) bearing cytoplasmic receptor, TCR zeta, FcR gamma, CD3 gamma, CD3 delta, CD3 epsilon, CD5, CD22, CD79a, CD79b, and CD66d, or a variant thereof.

In certain embodiments, the intracellular signaling domain comprises an intracellular domain of CD3ζ or a variant thereof.

In certain embodiments, the intracellular domain of CD3 comprises the amino acid sequence set forth in SEQ ID NO: 37.

In certain embodiments, the CAR comprises an amino acid sequence at least 80%, 85%, 90%, 95%, 96%, 97%, 98%, 99%, or 100% identical to SEQ ID NO: 38, 39, 40, 41, 42, or 43.

In certain embodiments, the CAR is encoded by a nucleotide sequence at least 80%, 85%, 90%, 95%, 96%, 97%, 98%, 99%, or 100% identical to SEQ ID NO: 48, 49, 54, 55, 60, or 61.

In another aspect, the invention includes a nucleic acid comprising a polynucleotide sequence encoding a chimeric antigen receptor (CAR), wherein the CAR comprises an antigen binding domain capable of binding the IIICS domain of fibronectin, a transmembrane domain, and an intracellular domain.

In certain embodiments, the antigen binding domain comprises a heavy chain variable region encoded by a nucleotide sequence at least 80%, 85%, 90%, 95%, 96%, 97%, 98%, 99%, or 100% identical to SEQ ID NO: 44 and/or a light chain variable region encoded by a nucleotide sequence at least 80%, 85%, 90%, 95%, 96%, 97%, 98%, 99%, or 100% identical to SEQ ID NO: 45.

In certain embodiments, the antigen binding domain is a single-chain variable fragment (scFv) encoded by a nucleotide sequence at least 80%, 85%, 90%, 95%, 96%, 97%, 98%, 99%, or 100% identical to SEQ ID NO: 46 or SEQ ID NO: 47.

In certain embodiments, the CAR is encoded by a nucleotide sequence at least 80%, 85%, 90%, 95%, 96%, 97%, 98%, 99%, or 100% identical to SEQ ID NO: 48 or 49.

In another aspect, the invention includes a nucleic acid comprising a polynucleotide sequence encoding a CAR, wherein the CAR comprises an antigen binding domain capable of binding the EDB domain of fibronectin, a transmembrane domain, and an intracellular domain.

In certain embodiments, the antigen binding domain comprises a heavy chain variable region encoded by a nucleotide sequence at least 80%, 85%, 90%, 95%, 96%, 97%, 98%, 99%, or 100% identical to SEQ ID NO: 50 and/or a light chain variable region encoded by a nucleotide sequence at least 80%, 85%, 90%, 95%, 96%, 97%, 98%, 99%, or 100% identical to SEQ ID NO: 51.

In certain embodiments, the antigen binding domain is a single-chain variable fragment (scFv) encoded by a nucleotide sequence at least 80%, 85%, 90%, 95%, 96%, 97%, 98%, 99%, or 100% identical to SEQ ID NO: 52 or SEQ ID NO: 53.

In certain embodiments, the CAR is encoded by a nucleotide sequence at least 80%, 85%, 90%, 95%, 96%, 97%, 98%, 99%, or 100% identical to SEQ ID NO: 54 or 55.

In certain embodiments, the antigen binding domain comprises a heavy chain variable region encoded by a nucleotide sequence at least 80%, 85%, 90%, 95%, 96%, 97%, 98%, 99%, or 100% identical to SEQ ID NO: 56 and/or a light chain variable region encoded by a nucleotide sequence at least 80%, 85%, 90%, 95%, 96%, 97%, 98%, 99%, or 100% identical to SEQ ID NO: 57.

In certain embodiments, the antigen binding domain is a single-chain variable fragment (scFv) encoded by a nucleotide sequence at least 80%, 85%, 90%, 95%, 96%, 97%, 98%, 99%, or 100% identical to SEQ ID NO: 58 or SEQ ID NO: 59.

In certain embodiments, the CAR is encoded by a nucleotide sequence at least 80%, 85%, 90%, 95%, 96%, 97%, 98%, 99%, or 100% identical to SEQ ID NO: 60 or 61.

In another aspect, the invention includes a vector comprising the nucleic acid of any one of claims 30-40.

In another aspect, the invention includes a modified immune cell or precursor cell thereof, comprising the CAR of any one of claims 1-29, or the nucleic acid of any one of claims 30-40.

In certain embodiments, the modified cell is an autologous cell.

In certain embodiments, the modified cell is a cell isolated from a human subject.

In certain embodiments, the modified cell is a modified T cell.

In another aspect, the invention includes a method for generating a modified immune cell or precursor cell thereof, comprising introducing into an immune or precursor cell any of the nucleic acids contemplated herein or any of the vectors contemplated herein.

In certain embodiments, the nucleic acid is introduced via viral transduction.

In certain embodiments, the viral transduction comprises contacting the immune or precursor cell with a viral vector comprising the nucleic acid encoding a CAR.

In certain embodiments, the viral vector is selected from the group consisting of a retroviral vector, a lentiviral vector, an adenoviral vector, and an adeno-associated viral vector.

In certain embodiments, the viral vector is a lentiviral vector.

In another aspect, the invention includes a method of treating cancer in a subject in need thereof, comprising administering to the subject the any of the modified immune or precursor cells contemplated herein or any modified immune or precursor cell generated by the methods contemplated herein.

In another aspect, the invention includes a method of treating cancer in a subject in need thereof, comprising administering to the subject a modified T cell comprising a chimeric antigen receptor (CAR), wherein the CAR comprises an antigen binding domain capable of binding the IIICS domain of fibronectin, a transmembrane domain, and an intracellular domain.

In certain embodiments, the antigen binding domain comprises at least one heavy chain variable region (HCDR) comprising the nucleotide sequence selected from the group consisting of SEQ ID NO: 1, SEQ ID NO: 2, and SEQ ID NO: 3.

In certain embodiments, the antigen binding domain comprises at least one light chain variable region (LCDR) comprising the nucleotide sequence selected from the group consisting of SEQ ID NO: 4, SEQ ID NO: 5, and SEQ ID NO: 6.

In certain embodiments, the antigen binding domain comprises a heavy chain variable region comprising an amino acid sequence at least 80%, 85%, 90%, 95%, 96%, 97%, 98%, 99%, or 100% identical to SEQ ID NO: 7 and/or a light chain variable region comprising an amino acid sequence at least 80%, 85%, 90%, 95%, 96%, 97%, 98%, 99%, or 100% identical to SEQ ID NO: 8.

In certain embodiments, the antigen binding domain is a single-chain variable fragment (scFv) comprising an amino acid sequence at least 80%, 85%, 90%, 95%, 96%, 97%, 98%, 99%, or 100% identical to SEQ ID NO: 10 or SEQ ID NO: 11.

In another aspect, the invention includes a method of treating cancer in a subject in need thereof, comprising administering to the subject a modified T cell comprising a chimeric antigen receptor (CAR), wherein the CAR comprises an antigen binding domain capable of binding the EDB domain of fibronectin, a transmembrane domain, and an intracellular domain.

In certain embodiments, the antigen binding domain comprises at least one heavy chain variable region (HCDR) comprising the nucleotide sequence selected from the group consisting of SEQ ID NO: 12, SEQ ID NO: 13, and SEQ ID NO: 14.

In certain embodiments, the antigen binding domain comprises at least one light chain variable region (LCDR) comprising the nucleotide sequence selected from the group consisting of SEQ ID NO: 15, SEQ ID NO: 16, and SEQ ID NO: 17.

In certain embodiments, the antigen binding domain comprises a heavy chain variable region comprising an amino acid sequence at least 80%, 85%, 90%, 95%, 96%, 97%, 98%, 99%, or 100% identical to SEQ ID NO: 18 and/or a light chain variable region comprising an amino acid sequence at least 80%, 85%, 90%, 95%, 96%, 97%, 98%, 99%, or 100% identical to SEQ ID NO: 19.

In certain embodiments, the antigen binding domain comprises at least one heavy chain variable region (HCDR) comprising the nucleotide sequence selected from the group consisting of SEQ ID NO: 23, SEQ ID NO: 24, and SEQ ID NO: 25.

In certain embodiments, the antigen binding domain comprises at least one light chain variable region (LCDR) comprising the nucleotide sequence selected from the group consisting of SEQ ID NO: 26, SEQ ID NO: 27, and SEQ ID NO: 28.

In certain embodiments, the antigen binding domain comprises a heavy chain variable region comprising an amino acid sequence at least 80%, 85%, 90%, 95%, 96%, 97%, 98%, 99%, or 100% identical to SEQ ID NO: 29 and/or a light chain variable region comprising an amino acid sequence at least 80%, 85%, 90%, 95%, 96%, 97%, 98%, 99%, or 100% identical to SEQ ID NO: 30.

In certain embodiments, the antigen binding domain is a single-chain variable fragment (scFv) comprising an amino acid sequence at least 80%, 85%, 90%, 95%, 96%, 97%, 98%, 99%, or 100% identical to SEQ ID NO: 31 or SEQ ID NO: 32.

In certain embodiments, the antigen binding domain is selected from the group consisting of a full length antibody or antigen-binding fragment thereof, a Fab, a single-chain variable fragment (scFv), or a single-domain antibody.

In certain embodiments, the CAR further comprises a CD8 alpha hinge sequence comprising the amino acid sequence set forth in SEQ ID NO: 34.

In certain embodiments, the transmembrane domain comprises a transmembrane domain selected from the group consisting of an artificial hydrophobic sequence, and a transmembrane domain of a type I transmembrane protein, an alpha, beta, or zeta chain of a T cell receptor, CD28, CD3 epsilon, CD45, CD4, CD5, CD8, CD9, CD16, CD22, CD33, CD37, CD64, CD80, CD86, OX40 (CD134), 4-1BB (CD137), ICOS, and CD154, or a transmembrane domain derived from a killer immunoglobulin-like receptor (KIR).

In certain embodiments, the transmembrane domain comprises a transmembrane domain of CD8 alpha comprising the amino acid sequence set forth in SEQ ID NO: 35.

In certain embodiments, the intracellular domain comprises a costimulatory signaling domain and an intracellular signaling domain.

In certain embodiments, the intracellular domain comprises a costimulatory domain of a protein selected from the group consisting of proteins in the TNFR superfamily, CD28, 4-1BB (CD137), OX40 (CD134), PD-1, CD7, LIGHT, CD83L, DAP10, DAP12, CD27, CD2, CDS, ICAM-1, LFA-1, Lck, TNFR-I, TNFR-II, Fas, CD30, CD40, ICOS, NKG2C, and B7-H3 (CD276), or a variant thereof, or an intracellular domain derived from a killer immunoglobulin-like receptor (KIR).

In certain embodiments, the intracellular domain comprises a costimulatory domain of 4-1BB.

In certain embodiments, the costimulatory domain of 4-1BB comprises the amino acid sequence set forth in SEQ ID NO: 36.

In certain embodiments, the intracellular signaling domain comprises an intracellular domain selected from the group consisting of cytoplasmic signaling domains of a human CD3 zeta chain (CD3), FcγRIII, FcsRI, a cytoplasmic tail of an Fc receptor, an immunoreceptor tyrosine-based activation motif (ITAM) bearing cytoplasmic receptor, TCR zeta, FcR gamma, CD3 gamma, CD3 delta, CD3 epsilon, CD5, CD22, CD79a, CD79b, and CD66d, or a variant thereof.

In certain embodiments, the intracellular signaling domain comprises an intracellular domain of CD3ζ or a variant thereof.

In certain embodiments, the intracellular domain of CD3 comprises the amino acid sequence set forth in SEQ ID NO: 37.

In certain embodiments, the CAR comprises an amino acid sequence at least 80%, 85%, 90%, 95%, 96%, 97%, 98%, 99%, or 100% identical to SEQ ID NO: 38, 39, 40, 41, 42, or 43.

In certain embodiments, the CAR is encoded by a nucleotide sequence at least 80%, 85%, 90%, 95%, 96%, 97%, 98%, 99%, or 100% identical to SEQ ID NO: 48, 49, 54, 55, 60, or 61.

In certain embodiments, the modified T cell is human.

In certain embodiments, the modified T cell is autologous.

In certain embodiments, the subject is human.

BRIEF DESCRIPTION OF THE DRAWINGS

The foregoing and other features and advantages of the present invention will be more fully understood from the following detailed description of illustrative embodiments taken in conjunction with the accompanying drawings.

FIG. 6A shows results from a human IFN-γ ELISA illustrating CAR specific reactivity. FIG. 6B shows results from an xCELLigence assay for cytotoxicity.

FIG. 14A shows weekly body weight (grams) and tumor volume (derived by caliper measurement) of each group. FIG. 14B shows weekly tumor volume of each mouse in the NTD group compared to the IIICS-FN CAR T cell group. FIG. 14C shows Log-fold change in tumor BLI overtime.

FIG. 17 illustrates results of a more statistically robust NSG model, which further support the findings presented in FIGS. 13-14. FIG. 17A shows weekly tumor volume (measured by caliper) of each group. FIG. 17B depicts the average serial BLI total flux plotted for each treatment group over time. Significance is determined by comparison of treatment groups to the NTD group of each given week. For FIG. 17A, the significance designation applies to all three treatment groups from Days 21-49, however only the TnMUC1 CAR T cell treated group is significantly different at day 56. (n=8-10 animals per group).

DETAILED DESCRIPTION

Figure 1:
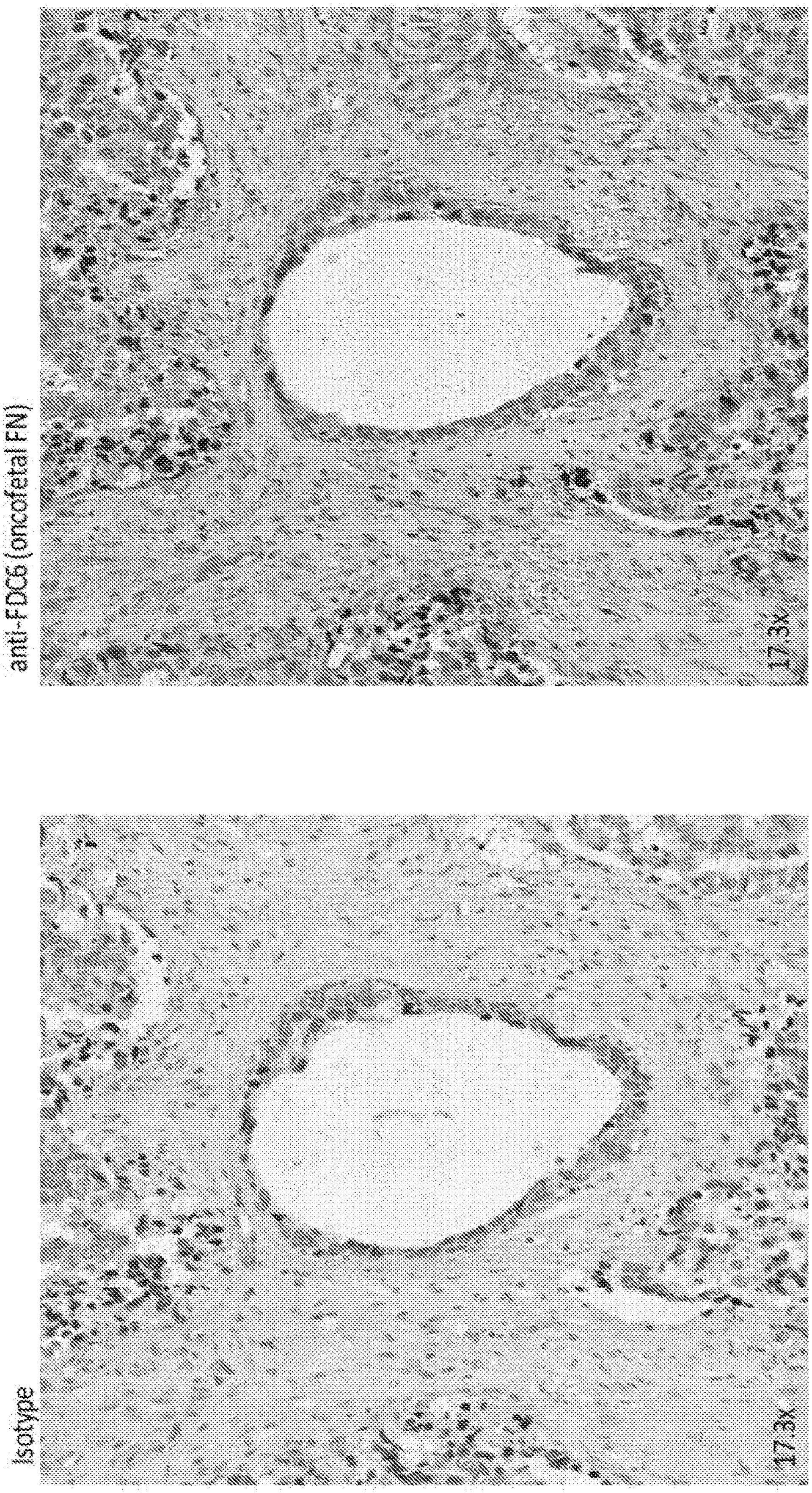
FIG. 1 illustrates the finding that FDC-6 antibody reacts highly to oncofetal FN, which is highly present in the stroma of human breast cancer tissue. Human breast cancer tissue sections stained positively for anti-FDC-6 monoclonal antibody (right panel) and negatively for an isotype control (left panel).

The present invention provides compositions and methods for modified immune cells or precursors thereof (e.g., modified T cells) comprising chimeric antigen receptors (CARs) capable of binding tumor-specific isoforms/epitopes of fibronectin. In certain embodiments, the CAR is specific for the EDB domain of fibronectin. In certain embodiments, the CAR is specific for the IIICS domain of fibronectin. Also provided are methods of using the CARs to treat cancer.

In order to enhance the efficacy of CAR-T cells against solid tumors, post-translational modifications that occur exclusively in transformed cells can be targeted. Aberrant glycosylation is considered a new hallmark of cancer development as glycans play a key role in tumor initiation, progression, and metastasis. Alterations in glycosyl-transferases and chaperone proteins lead to the development of various tumor-associated antigens. For example, defects in mucin-type O-glycosylation leads to cell surface expression of terminal GalNAc, or Tn-antigen, on many tumors. Previous pre-clinical studies that target TnMUC1 with 5E5-CART cells demonstrated efficacy against multiple tumor histotypes, and these studies have recently translated into a phase I clinical trial (NCT04025216) for the treatment of NSCLC, ovarian cancer, triple-negative breast cancer, pancreatic adenocarcinoma, and multiple myeloma.

In one embodiment, the present work targets Tn-antigen present on the IIICS domain of oncofetal fibronectin (onfFN), a cancer-specific splice isoform of the extracellular matrix protein (ECM) fibronectin (FN). Current data shows that onfFN-targeting CAR-T cells secrete high concentrations of IFN-γ in response to co-culture with metastatic prostate cancer cells. In vitro studies reveal onfFN-targeting CAR-T cells as a potent cytotoxic agent against the androgen-insensitive PC3 and DU145 prostate cancer cell lines at multiple effector-to-target ratios. Additionally, IIICS-FN targeting CAR-T cells promote rapid anti-tumor rejection in a subcutaneous PC3 xenograft model of prostate cancer. Herein, a strategy was developed to target a cancer-specific glycosylated epitope on an ECM protein found within the TME with CAR-T cells, which demonstrated in vitro and in vivo efficacy against metastatic prostate tumors. This data provides a novel cancer immunotherapy approach for the treatment of prostate tumors and other cancer histotypes.

It is to be understood that the methods described in this disclosure are not limited to particular methods and experimental conditions disclosed herein as such methods and conditions may vary. It is also to be understood that the terminology used herein is for the purpose of describing particular embodiments only, and is not intended to be limiting.

Furthermore, the experiments described herein, unless otherwise indicated, use conventional molecular and cellular biological and immunological techniques within the skill of the art. Such techniques are well known to the skilled worker, and are explained fully in the literature. See, e.g., Ausubel, et al., ed., Current Protocols in Molecular Biology, John Wiley & Sons, Inc., NY, N.Y. (1987-2008), including all supplements, Molecular Cloning: A Laboratory Manual (Fourth Edition) by M R Green and J. Sambrook and Harlow et al., Antibodies: A Laboratory Manual, Chapter 14, Cold Spring Harbor Laboratory, Cold Spring Harbor (2013, 2nd edition).

A. Definitions

Unless otherwise defined, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

Generally, nomenclature used in connection with cell and tissue culture, molecular biology, immunology, microbiology, genetics and protein and nucleic acid chemistry and hybridization described herein is well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

That the disclosure may be more readily understood, select terms are defined below.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

As used herein, to "alleviate" a disease means reducing the severity of one or more symptoms of the disease.

The term "antigen" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen.

Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

As used herein, the term "autologous" is meant to refer to any material derived from the same individual to which it is later to be re-introduced into the individual.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MEW class I molecule, BTLA and a Toll ligand receptor.

A "co-stimulatory signal", as used herein, refers to a signal, which in combination with a primary signal, such as TCR/CD3 ligation, leads to T cell proliferation and/or upregulation or downregulation of key molecules.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "downregulation" as used herein refers to the decrease or elimination of gene expression of one or more genes.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to an amount that when administered to a mammal, causes a detectable level of immune suppression or tolerance compared to the immune response detected in the absence of the composition of the invention. The immune response can be readily assessed by a plethora of art-recognized methods. The skilled artisan would understand that the amount of the composition administered herein varies and can be readily determined based on a number of factors such as the disease or condition being treated, the age and health and physical condition of the mammal being treated, the severity of the disease, the particular compound being administered, and the like.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

The term "epitope" as used herein is defined as a small chemical molecule on an antigen that can elicit an immune response, inducing B and/or T cell responses. An antigen can have one or more epitopes. Most antigens have many epitopes; i.e., they are multivalent. In general, an epitope is roughly about 10 amino acids and/or sugars in size. Preferably, the epitope is about 4-18 amino acids, more preferably about 5-16 amino acids, and even more most preferably 6-14 amino acids, more preferably about 7-12, and most preferably about 8-10 amino acids. One skilled in the art understands that generally the overall three-dimensional structure, rather than the specific linear sequence of the molecule, is the main criterion of antigenic specificity and therefore distinguishes one epitope from another. Based on the present disclosure, a peptide used in the present invention can be an epitope.

As used herein, the term "exogenous" refers to any material introduced from or produced outside an organism, cell, tissue or system.

The term "expand" as used herein refers to increasing in number, as in an increase in the number of T cells. In one embodiment, the T cells that are expanded ex vivo increase in number relative to the number originally present in the culture. In another embodiment, the T cells that are expanded ex vivo increase in number relative to other cell types in the culture. The term "ex vivo," as used herein, refers to cells that have been removed from a living organism, (e.g., a human) and propagated outside the organism (e.g., in a culture dish, test tube, or bioreactor).

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

The term "immune response" as used herein is defined as a cellular response to an antigen that occurs when lymphocytes identify antigenic molecules as foreign and induce the formation of antibodies and/or activate lymphocytes to remove the antigen.

The term "immunosuppressive" is used herein to refer to reducing overall immune response.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "oligonucleotide" typically refers to short polynucleotides. It will be understood that when a nucleotide sequence is represented by a DNA sequence (i.e., A, T, C, G), this also includes an RNA sequence (i.e., A, U, C, G) in which "U" replaces "T."

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/

CD3 complex) with its cognate ligand thereby mediating a signal transduction event, such as, but not limited to, signal transduction via the TCR/CD3 complex. Stimulation can mediate altered expression of certain molecules, such as downregulation of TGF-beta, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

A "target site" or "target sequence" refers to a nucleic acid sequence that defines a portion of a nucleic acid to which a binding molecule may specifically bind under conditions sufficient for binding to occur. In some embodiments, a target sequence refers to a genomic nucleic acid sequence that defines a portion of a nucleic acid to which a binding molecule may specifically bind under conditions sufficient for binding to occur.

As used herein, the term "T cell receptor" or "TCR" refers to a complex of membrane proteins that participate in the activation of T cells in response to the presentation of antigen. The TCR is responsible for recognizing antigens bound to major histocompatibility complex molecules. TCR is composed of a heterodimer of an alpha ($\alpha$) and beta ($\beta$) chain, although in some cells the TCR consists of gamma and delta ($\gamma/\delta$) chains. TCRs may exist in alpha/beta and gamma/delta forms, which are structurally similar but have distinct anatomical locations and functions. Each chain is composed of two extracellular domains, a variable and constant domain. In some embodiments, the TCR may be modified on any cell comprising a TCR, including, for example, a helper T cell, a cytotoxic T cell, a memory T cell, regulatory T cell, natural killer T cell, and gamma delta T cell.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

B. Chimeric Antigen Receptors

The present invention provides compositions and methods comprising chimeric antigen receptors (CARs) capable of binding tumor-specific epitopes/isoforms of fibronectin. CARs of the present invention comprise an antigen binding domain, a transmembrane domain, and an intracellular domain. In certain embodiments, the CAR is capable of binding the IIICS domain of fibronectin. In certain embodiments, the CAR is capable of binding the EDA domain of fibronectin. In certain embodiments, the CAR is capable of binding the EDB domain of fibronectin.

Also provided are compositions and methods for modified immune cells or precursors thereof, e.g., modified T cells, comprising the CAR. Thus, in some embodiments, the immune cell has been genetically modified to express the CAR. Nucleic acids encoding said CARs, vectors encoding said nucleic acids, and modified cells (e.g. modified T cells) comprising said CARs, vectors, or nucleic acids, are also provided.

The antigen binding domain may be operably linked to another domain of the CAR, such as the transmembrane domain or the intracellular domain, both described elsewhere herein, for expression in the cell. In one embodiment, a first nucleic acid sequence encoding the antigen binding domain is operably linked to a second nucleic acid encoding a transmembrane domain, and further operably linked to a third a nucleic acid sequence encoding an intracellular domain.

The antigen binding domains described herein can be combined with any of the transmembrane domains described herein, any of the intracellular domains or cytoplasmic domains described herein, or any of the other domains described herein that may be included in a CAR of the present invention. A subject CAR of the present invention may also include a hinge domain as described herein. A subject CAR of the present invention may also include a spacer domain as described herein. In some embodiments, each of the antigen binding domain, transmembrane domain, and intracellular domain is separated by a linker.

Antigen Binding Domain

The antigen binding domain of a CAR is an extracellular region of the CAR for binding to a specific target antigen including proteins, carbohydrates, and glycolipids. A subject CAR of the invention comprises an antigen binding domain that is capable of binding a cancer-specific isoform/epitope/domain of fibronectin. In certain embodiments, the antigen binding domain is capable of binding the IIICS domain of fibronectin. In certain embodiments, the antigen binding domain is capable of binding the EDA domain of fibronectin. In certain embodiments, the antigen binding domain is capable of binding the EDB domain of fibronectin.

The antigen binding domain can include any domain that binds to the antigen and may include, but is not limited to, a monoclonal antibody, a polyclonal antibody, a synthetic antibody, a human antibody, a humanized antibody, a non-human antibody, a single-domain antibody, a full length antibody or any antigen-binding fragment thereof, a Fab, and a single-chain variable fragment (scFv). In some embodiments, the antigen binding domain portion comprises a mammalian antibody or a fragment thereof. The choice of antigen binding domain may depend upon the type and number of antigens that are present on the surface of a target cell.

In certain embodiments, the antigen binding domain is selected from the group consisting of an antibody, an antigen binding fragment (Fab), and a single-chain variable fragment (scFv). In one embodiment, the antigen binding domain is an antibody specific for the IIICS domain of fibronectin. In one embodiment, the antigen binding domain is a Fab specific for the IIICS domain of fibronectin. In one embodiment, the antigen binding domain is an scFv specific for the IIICS domain of fibronectin. In one embodiment, the antigen binding domain is an antibody specific for the EDA domain of fibronectin. In one embodiment, the antigen binding domain is a Fab specific for the EDA domain of fibronectin. In one embodiment, the antigen binding domain is an scFv specific for the EDA domain of fibronectin. In one embodiment, the antigen binding domain is an antibody specific for the EDB domain of fibronectin. In one embodiment, the antigen binding domain is a Fab specific for the EDB domain of fibronectin. In one embodiment, the antigen binding domain is an scFv specific for the EDB domain of fibronectin.

As used herein, the term "single-chain variable fragment" or "scFv" is a fusion protein of the variable regions of the heavy (VH) and light chains (VL) of an immunoglobulin (e.g., mouse or human) covalently linked to form a VH::VL heterodimer. The heavy (VH) and light chains (VL) are either joined directly or joined by a peptide-encoding linker, which connects the N-terminus of the VH with the C-terminus of the VL, or the C-terminus of the VH with the N-terminus of the VL. In some embodiments, the antigen binding domain (e.g., fibronectin binding domain) comprises an scFv having the configuration from N-terminus to C-terminus, VH—linker—VL. In some embodiments, the antigen binding domain comprises an scFv having the configuration from N-terminus to C-terminus, VL—linker—VH. Those of skill in the art would be able to select the appropriate configuration for use in the present invention.

The linker is usually rich in glycine for flexibility, as well as serine or threonine for solubility. The linker can link the heavy chain variable region and the light chain variable region of the extracellular antigen-binding domain. Non-limiting examples of linkers are disclosed in Shen et al., Anal. Chem. 80(6):1910-1917 (2008) and WO 2014/087010, the contents of which are hereby incorporated by reference in their entireties. Various linker sequences are known in the art, including, without limitation, glycine serine (GS) linkers such as $(GS)_n$, $(GSGGS)_n$ (SEQ ID NO:62), $(GGGS)_n$ (SEQ ID NO:63), and $(GGGGS)_n$ (SEQ ID NO:64), where n represents an integer of at least 1. Exemplary linker sequences can comprise amino acid sequences including, without limitation, GGSG (SEQ ID NO:65), GGSGG (SEQ ID NO:66), GSGSG (SEQ ID NO:67), GSGGG (SEQ ID NO:68), GGGSG (SEQ ID NO:69), GSSSG (SEQ ID NO:70), GGGGS (SEQ ID NO:71), GGGGSGGGGSGGGGS (SEQ ID NO:72) and the like. Those of skill in the art would be able to select the appropriate linker sequence for use in the present invention. In one embodiment, an antigen binding domain of the present invention comprises a heavy chain variable region (VH) and a light chain variable region (VL), wherein the VH and VL is separated by the linker sequence having the amino acid sequence GGGGSGGGGSGGGGS (SEQ ID NO:72), which may be encoded by the nucleic acid sequence GGTGGCGGTGGCTCGGGCGGTGGTGGGTCGGGTG-GCGGCGGATCT (SEQ ID NO:73).

Despite removal of the constant regions and the introduction of a linker, scFv proteins retain the specificity of the original immunoglobulin. Single chain Fv polypeptide antibodies can be expressed from a nucleic acid comprising VH- and VL-encoding sequences as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., Hyrbidoma (Larchmt) 2008 27(6):455-51; Peter et al., J Cachexia Sarcopenia Muscle 2012 Aug. 12; Shieh et al., J Imunol 2009 183(4):2277-85; Giomarelli et al., Thromb Haemost 2007 97(6):955-63; Fife eta., J Clin Invst 2006 116(8):2252-61; Brocks et al., Immunotechnology 1997 3(3):173-84; Moosmayer et al., Ther Immunol 1995 2 (10:31-40). Agonistic scFvs having stimulatory activity have been described (see, e.g., Peter et al., J Bioi Chem 2003 25278(38):36740-7; Xie et al., Nat Biotech 1997 15(8):768-71; Ledbetter et al., Crit Rev Immunol 1997 17 (5-6):427-55; Ho et al., BioChim Biophys Acta 2003 1638(3):257-66).

As used herein, "Fab" refers to a fragment of an antibody structure that binds to an antigen but is monovalent and does not have a Fc portion, for example, an antibody digested by the enzyme papain yields two Fab fragments and an Fc fragment (e.g., a heavy (H) chain constant region; Fc region that does not bind to an antigen).

As used herein, "F(ab')2" refers to an antibody fragment generated by pepsin digestion of whole IgG antibodies, wherein this fragment has two antigen binding (ab') (bivalent) regions, wherein each (ab') region comprises two separate amino acid chains, a part of a H chain and a light (L) chain linked by an S—S bond for binding an antigen and where the remaining H chain portions are linked together. A "F(ab')2" fragment can be split into two individual Fab' fragments.

In some embodiments, the antigen binding domain may be derived from the same species in which the CAR will ultimately be used. For example, for use in humans, the antigen binding domain of the CAR may comprise a human antibody or a fragment thereof. In some embodiments, the antigen binding domain may be derived from a different species in which the CAR will ultimately be used. For example, for use in humans, the antigen binding domain of the CAR may comprise a murine antibody or a fragment thereof.

In certain embodiments, the antigen binding domain comprises a heavy chain variable region that comprises three heavy chain complementarity determining regions (HCDRs) and a light chain variable region that comprises three light chain complementarity determining regions (LCDRs). In certain embodiments, HCDR1 comprises the amino acid sequence of SEQ ID NO: 1, and/or HCDR2 comprises the amino acid sequence of SEQ ID NO: 2, and/or HCDR3 comprises the amino acid sequence of SEQ ID NO: 3, and/or LCDR1 comprises the amino acid sequence of SEQ ID NO: 4, and/or LCDR2 comprises the amino acid sequence of SEQ ID NO: 5, and/or LCDR3 comprises the amino acid sequence of SEQ ID NO: 6.

In certain embodiments, HCDR1 comprises the amino acid sequence of SEQ ID NO: 12, and/or HCDR2 comprises the amino acid sequence of SEQ ID NO: 13, and/or HCDR3 comprises the amino acid sequence of SEQ ID NO: 14, and/or LCDR1 comprises the amino acid sequence of SEQ ID NO: 15, and/or LCDR2 comprises the amino acid sequence of SEQ ID NO: 16, and/or LCDR3 comprises the amino acid sequence of SEQ ID NO: 17.

In certain embodiments, HCDR1 comprises the amino acid sequence of SEQ ID NO: 23, and/or HCDR2 comprises the amino acid sequence of SEQ ID NO: 24, and/or HCDR3 comprises the amino acid sequence of SEQ ID NO: 25, and/or LCDR1 comprises the amino acid sequence of SEQ ID NO: 26, and/or LCDR2 comprises the amino acid sequence of SEQ ID NO: 27, and/or LCDR3 comprises the amino acid sequence of SEQ ID NO: 28.

In certain embodiments, the heavy chain variable region (VH) of the antigen binding domain comprises an amino acid sequence at least 80%, 85%, 90%, 95%, 96%, 97%, 98%, 99%, or 100% identical to SEQ ID NO: 7, and/or the light chain variable region (VL) comprises an amino acid sequence at least 80%, 85%, 90%, 95%, 96%, 97%, 98%, 99%, or 100% identical to SEQ ID NO: 8.

In certain embodiments, the heavy chain variable region (VH) of the antigen binding domain comprises an amino acid sequence at least 80%, 85%, 90%, 95%, 96%, 97%, 98%, 99%, or 100% identical to SEQ ID NO: 18, and/or the light chain variable region (VL) comprises an amino acid sequence at least 80%, 85%, 90%, 95%, 96%, 97%, 98%, 99%, or 100% identical to SEQ ID NO: 19.

In certain embodiments, the heavy chain variable region (VH) of the antigen binding domain comprises an amino acid sequence at least 80%, 85%, 90%, 95%, 96%, 97%, 98%, 99%, or 100% identical to SEQ ID NO: 29, and/or the light chain variable region (VL) comprises an amino acid sequence at least 80%, 85%, 90%, 95%, 96%, 97%, 98%, 99%, or 100% identical to SEQ ID NO: 30.

In certain embodiments, the antigen binding domain is a single-chain variable fragment (scFv) comprising an amino acid sequence at least 80%, 85%, 90%, 95%, 96%, 97%, 98%, 99%, or 100% identical to SEQ ID NO: 10 or SEQ ID NO: 11. In certain embodiments, the antigen binding domain is a single-chain variable fragment (scFv) comprising an amino acid sequence at least 80%, 85%, 90%, 95%, 96%, 97%, 98%, 99%, or 100% identical to SEQ ID NO: 21 or SEQ ID NO: 22. In certain embodiments, the antigen binding domain is a single-chain variable fragment (scFv) comprising an amino acid sequence at least 80%, 85%, 90%, 95%, 96%, 97%, 98%, 99%, or 100% identical to SEQ ID NO: 31 or SEQ ID NO: 32.

In certain embodiments, the antigen binding domain comprises a linker. In certain embodiments, the linker comprises SEQ ID NO: 9 or SEQ ID NO: 20.

Tolerable variations of the antigen binding domain sequences will be known to those of skill in the art. For example, in some embodiments the antigen binding domain comprises an amino acid sequence that has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any of the amino acid sequences set forth in any one of SEQ ID NOs: 1-32.

Transmembrane Domain

CARs of the present invention may comprise a transmembrane domain that connects the antigen binding domain of the CAR to the intracellular domain of the CAR. The transmembrane domain of a subject CAR is a region that is capable of spanning the plasma membrane of a cell (e.g., an immune cell or precursor thereof). The transmembrane domain is for insertion into a cell membrane, e.g., a eukaryotic cell membrane. In some embodiments, the transmembrane domain is interposed between the antigen binding domain and the intracellular domain of a CAR.

In some embodiments, the transmembrane domain is naturally associated with one or more of the domains in the CAR. In some embodiments, the transmembrane domain can be selected or modified by one or more amino acid substitutions to avoid binding of such domains to the transmembrane domains of the same or different surface membrane proteins, to minimize interactions with other members of the receptor complex.

The transmembrane domain may be derived either from a natural or a synthetic source. Where the source is natural, the domain may be derived from any membrane-bound or transmembrane protein, e.g., a Type I transmembrane protein. Where the source is synthetic, the transmembrane domain may be any artificial sequence that facilitates insertion of the CAR into a cell membrane, e.g., an artificial hydrophobic sequence. Examples of the transmembrane domain of particular use in this invention include, without limitation, transmembrane domains derived from (i.e. comprise at least the transmembrane region(s) of) the alpha, beta or zeta chain of the T cell receptor, CD28, CD3 epsilon, CD45, CD4, CD5, CD7, CD8, CD9, CD16, CD22, CD33, CD37, CD64, CD80, CD86, CD134 (OX-40), CD137 (4-1BB), CD154 (CD40L), ICOS, CD278, Toll-like receptor 1 (TLR1), TLR2, TLR3, TLR4, TLR5, TLR6, TLR7, TLR8, TLR9 or a transmembrane domain derived from a killer immunoglobulin-like receptor (KIR).

In certain embodiments, the transmembrane domain comprises a transmembrane domain of CD8. In certain embodiments, the transmembrane domain of CD8 is a transmembrane domain of CD8a. In certain embodiments, the transmembrane domain comprises the amino acid sequence set forth in SEQ ID NO: 35.

In some embodiments, the transmembrane domain may be synthetic, in which case it will comprise predominantly hydrophobic residues such as leucine and valine. Preferably a triplet of phenylalanine, tryptophan and valine will be found at each end of a synthetic transmembrane domain.

The transmembrane domains described herein can be combined with any of the antigen binding domains described herein, any of the intracellular domains described herein, or any of the other domains described herein that may be included in a subject CAR.

In some embodiments, the transmembrane domain further comprises a hinge region. A subject CAR of the present invention may also include a hinge region. The hinge region of the CAR is a hydrophilic region which is located between the antigen binding domain and the transmembrane domain. In some embodiments, this domain facilitates proper protein folding for the CAR. The hinge region is an optional component for the CAR. The hinge region may include a domain selected from Fc fragments of antibodies, hinge regions of antibodies, CH2 regions of antibodies, CH3 regions of antibodies, artificial hinge sequences or combinations thereof. Examples of hinge regions include, without limitation, a CD8a hinge, artificial hinges made of polypeptides which may be as small as, three glycines (Gly), as well as CH1 and CH3 domains of IgGs (such as human IgG4).

In some embodiments, a subject CAR of the present disclosure includes a hinge region that connects the antigen binding domain with the transmembrane domain, which, in turn, connects to the intracellular domain. The hinge region is preferably capable of supporting the antigen binding domain to recognize and bind to the target antigen on the target cells (see, e.g., Hudecek et al., *Cancer Immunol. Res.* (2015) 3(2): 125-135). In some embodiments, the hinge region is a flexible domain, thus allowing the antigen binding domain to have a structure to optimally recognize the specific structure and density of the target antigens on a cell such as tumor cell (Hudecek et al., supra). The flexibility of the hinge region permits the hinge region to adopt many different conformations.

In some embodiments, the hinge region is an immunoglobulin heavy chain hinge region. In some embodiments, the hinge region is a hinge region polypeptide derived from a receptor (e.g., a CD8-derived hinge region). In certain embodiments, the hinge region is a CD8a hinge. In certain embodiments, the hinge region comprises the amino acid sequence set forth in SEQ ID NO: 34.

The hinge region can have a length of from about 4 amino acids to about 50 amino acids, e.g., from about 4 aa to about 10 aa, from about 10 aa to about 15 aa, from about 15 aa to about 20 aa, from about 20 aa to about 25 aa, from about 25 aa to about 30 aa, from about 30 aa to about 40 aa, or from about 40 aa to about 50 aa. In some embodiments, the hinge region can have a length of greater than 5 aa, greater than 10 aa, greater than 15 aa, greater than 20 aa, greater than 25 aa, greater than 30 aa, greater than 35 aa, greater than 40 aa, greater than 45 aa, greater than 50 aa, greater than 55 aa, or more.

Suitable hinge regions can be readily selected and can be of any of a number of suitable lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and can be 1, 2, 3, 4, 5, 6, or 7 amino acids. Suitable hinge regions can have a length of greater than 20 amino acids (e.g., 30, 40, 50, 60 or more amino acids).

For example, hinge regions include glycine polymers $(G)_n$, glycine-serine polymers (including, for example, $(GS)_n$, $(GSGGS)_n$ (SEQ ID NO:62) and $(GGGS)_n$ (SEQ ID NO:63), where n is an integer of at least one), glycine-alanine polymers, alanine-serine polymers, and other flexible linkers known in the art. Glycine and glycine-serine polymers can be used; both Gly and Ser are relatively unstructured, and therefore can serve as a neutral tether between components. Glycine polymers can be used; glycine accesses significantly more phi-psi space than even alanine, and is much less restricted than residues with longer side chains (see, e.g., Scheraga, *Rev. Computational. Chem.* (1992) 2: 73-142). Exemplary hinge regions can comprise amino acid sequences including, but not limited to, GGSG (SEQ ID NO:65), GGSGG (SEQ ID NO:66), GSGSG (SEQ ID NO:67), GSGGG (SEQ ID NO:68), GGGSG (SEQ ID NO:69), GSSSG (SEQ ID NO:70), and the like.

In some embodiments, the hinge region is an immunoglobulin heavy chain hinge region. Immunoglobulin hinge region amino acid sequences are known in the art; see, e.g., Tan et al., *Proc. Natl. Acad. Sci. USA* (1990) 87(1):162-166; and Huck et al., *Nucleic Acids Res.* (1986) 14(4): 1779-1789. As non-limiting examples, an immunoglobulin hinge region can include one of the following amino acid sequences: DKTHT (SEQ ID NO:74); CPPC (SEQ ID NO:75); CPEPKSCDTPPPCPR (SEQ ID NO:76) (see, e.g., Glaser et al., *J. Biol. Chem.* (2005) 280:41494-41503); ELKTPLGDTTHT (SEQ ID NO:77); KSCDKTHTCP (SEQ ID NO:78); KCCVDCP (SEQ ID NO:79); KYGPPCP (SEQ ID NO:80); EPKSCDKTHTCPPCP (SEQ ID NO:81) (human IgG1 hinge); ERKCCVECPPCP (SEQ ID NO:82) (human IgG2 hinge); ELKTPLGDTTHTCPRCP (SEQ ID NO:83) (human IgG3 hinge); SPNMVPHAHHAQ (SEQ ID NO:84) (human IgG4 hinge); and the like.

The hinge region can comprise an amino acid sequence of a human IgG1, IgG2, IgG3, or IgG4, hinge region. In one embodiment, the hinge region can include one or more amino acid substitutions and/or insertions and/or deletions compared to a wild-type (naturally-occurring) hinge region. For example, His229 of human IgG1 hinge can be substituted with Tyr, so that the hinge region comprises the sequence EPKSCDKTYTCPPCP (SEQ ID NO:85); see, e.g., Yan et al., *J. Biol. Chem.* (2012) 287: 5891-5897. In one embodiment, the hinge region can comprise an amino acid sequence derived from human CD8, or a variant thereof Intracellular Signaling Domain A subject CAR of the present invention also includes an intracellular signaling domain. The terms "intracellular signaling domain" and "intracellular domain" are used interchangeably herein. The intracellular signaling domain of the CAR is responsible for activation of at least one of the effector functions of the cell in which the CAR is expressed (e.g., immune cell). The intracellular signaling domain transduces the effector function signal and directs the cell (e.g., immune cell) to perform its specialized function, e.g., harming and/or destroying a target cell.

Examples of an intracellular domain for use in the invention include, but are not limited to, the cytoplasmic portion of a surface receptor, co-stimulatory molecule, and any molecule that acts in concert to initiate signal transduction in the T cell, as well as any derivative or variant of these elements and any synthetic sequence that has the same functional capability.

Examples of the intracellular signaling domain include, without limitation, the ζ chain of the T cell receptor complex or any of its homologs, e.g., η chain, FcsRIγ and β chains, MB 1 (Iga) chain, B29 (Ig) chain, etc., human CD3 zeta chain, CD3 polypeptides (Δ, δ and ε), syk family tyrosine kinases (Syk, ZAP 70, etc.), src family tyrosine kinases (Lck, Fyn, Lyn, etc.), and other molecules involved in T cell transduction, such as CD2, CD5 and CD28. In one embodiment, the intracellular signaling domain may be human CD3 zeta chain, FcγRIII, FcsRI, cytoplasmic tails of Fc receptors, an immunoreceptor tyrosine-based activation motif (ITAM) bearing cytoplasmic receptors, and combinations thereof.

In one embodiment, the intracellular signaling domain of the CAR includes any portion of one or more co-stimulatory molecules, such as at least one signaling domain from CD2, CD3, CD8, CD27, CD28, ICOS, 4-1BB, PD-1, any derivative or variant thereof, any synthetic sequence thereof that has the same functional capability, and any combination thereof.

Other examples of the intracellular domain include a fragment or domain from one or more molecules or receptors including, but not limited to, TCR, CD3 zeta, CD3 gamma, CD3 delta, CD3 epsilon, CD86, common FcR gamma, FcR beta (Fc Epsilon RIb), CD79a, CD79b, Fcgamma RIIa, DAP10, DAP12, T cell receptor (TCR), CD8, CD27, CD28, 4-1BB (CD137), OX9, OX40, CD30, CD40, PD-1, ICOS, a KIR family protein, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD127, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CDlib, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, NKG2D, Toll-like receptor 1 (TLR1), TLR2, TLR3, TLR4, TLR5, TLR6, TLR7, TLR8, TLR9, other co-stimulatory molecules described herein, any derivative, variant, or fragment thereof, any synthetic sequence of a co-stimulatory molecule that has the same functional capability, and any combination thereof.

Additional examples of intracellular domains include, without limitation, intracellular signaling domains of several types of various other immune signaling receptors, including, but not limited to, first, second, and third generation T cell signaling proteins including CD3, B7 family costimulatory, and Tumor Necrosis Factor Receptor (TNFR) superfamily receptors (see, e.g., Park and Brentjens, J. Clin. Oncol. (2015) 33(6): 651-653). Additionally, intracellular signaling domains may include signaling domains used by NK and NKT cells (see, e.g., Hermanson and Kaufman, Front. Immunol. (2015) 6: 195) such as signaling domains of NKp30 (B7-H6) (see, e.g., Zhang et al., J. Immunol. (2012) 189(5): 2290-2299), and DAP 12 (see, e.g., Topfer et al., J. Immunol. (2015) 194(7): 3201-3212), NKG2D, NKp44, NKp46, DAP10, and CD3z.

Intracellular signaling domains suitable for use in a subject CAR of the present invention include any desired signaling domain that provides a distinct and detectable signal (e.g., increased production of one or more cytokines by the cell; change in transcription of a target gene; change in activity of a protein; change in cell behavior, e.g., cell death; cellular proliferation; cellular differentiation; cell survival; modulation of cellular signaling responses; etc.) in response to activation of the CAR (i.e., activated by antigen and dimerizing agent). In some embodiments, the intracellular signaling domain includes at least one (e.g., one, two, three, four, five, six, etc.) ITAM motifs as described below. In some embodiments, the intracellular signaling domain includes DAP10/CD28 type signaling chains. In some embodiments, the intracellular signaling domain is not covalently attached to the membrane bound CAR, but is instead diffused in the cytoplasm.

Intracellular signaling domains suitable for use in a subject CAR of the present invention include immunoreceptor tyrosine-based activation motif (ITAM)-containing intracellular signaling polypeptides. In some embodiments, an ITAM motif is repeated twice in an intracellular signaling domain, where the first and second instances of the ITAM motif are separated from one another by 6 to 8 amino acids. In one embodiment, the intracellular signaling domain of a subject CAR comprises 3 ITAM motifs.

In some embodiments, intracellular signaling domains includes the signaling domains of human immunoglobulin receptors that contain immunoreceptor tyrosine based activation motifs (ITAMs) such as, but not limited to, FcgammaRI, FcgammaRIIA, FcgammaRIIC, FcgammaRIIIA, FcRL5 (see, e.g., Gillis et al., Front. Immunol. (2014) 5:254).

A suitable intracellular signaling domain can be an ITAM motif-containing portion that is derived from a polypeptide that contains an ITAM motif. For example, a suitable intracellular signaling domain can be an ITAM motif-containing domain from any ITAM motif-containing protein. Thus, a suitable intracellular signaling domain need not contain the entire sequence of the entire protein from which it is derived. Examples of suitable ITAM motif-containing polypeptides include, but are not limited to: DAP12, FCER1G (Fc epsilon receptor I gamma chain), CD3D (CD3 delta), CD3E (CD3 epsilon), CD3G (CD3 gamma), CD3Z (CD3 zeta), and CD79A (antigen receptor complex-associated protein alpha chain).

In one embodiment, the intracellular signaling domain is derived from DAP12 (also known as TYROBP; TYRO protein tyrosine kinase binding protein; KARAP; PLOSL; DNAX-activation protein 12; KAR-associated protein; TYRO protein tyrosine kinase-binding protein; killer activating receptor associated protein; killer-activating receptor-associated protein; etc.). In one embodiment, the intracellular signaling domain is derived from FCER1G (also known as FCRG; Fc epsilon receptor I gamma chain; Fc receptor gamma-chain; fc-epsilon RI-gamma; fcRgamma; fceR1 gamma; high affinity immunoglobulin epsilon receptor subunit gamma; immunoglobulin E receptor, high affinity, gamma chain; etc.). In one embodiment, the intracellular signaling domain is derived from T-cell surface glycoprotein CD3 delta chain (also known as CD3D; CD3-DELTA; T3D; CD3 antigen, delta subunit; CD3 delta; CD3d antigen, delta polypeptide (TiT3 complex); OKT3, delta chain; T-cell receptor T3 delta chain; T-cell surface glycoprotein CD3 delta chain; etc.). In one embodiment, the intracellular signaling domain is derived from T-cell surface glycoprotein CD3 epsilon chain (also known as CD3e, T-cell surface antigen T3/Leu-4 epsilon chain, T-cell surface glycoprotein CD3 epsilon chain, AI504783, CD3, CD3epsilon, T3e, etc.). In one embodiment, the intracellular signaling domain is derived from T-cell surface glycoprotein CD3 gamma chain (also known as CD3G, T-cell receptor T3 gamma chain, CD3-GAMMA, T3G, gamma polypeptide (TiT3 complex), etc.). In one embodiment, the intracellular signaling domain is derived from T-cell surface glycoprotein CD3 zeta chain (also known as CD3Z, T-cell receptor T3 zeta chain, CD247, CD3-ZETA, CD3H, CD3Q, T3Z, TCRZ, etc.). In one embodiment, the intracellular signaling domain is derived from CD79A (also known as B-cell antigen receptor complex-associated protein alpha chain; CD79a antigen (immunoglobulin-associated alpha); MB-1 membrane glycoprotein; ig-alpha; membrane-bound immunoglobulin-associated protein; surface IgM-associated protein; etc.). In one embodiment, an intracellular signaling domain suitable for use in an FN3 CAR of the present disclosure includes a DAP10/CD28 type signaling chain. In one embodiment, an intracellular signaling domain suitable for use in an FN3

CAR of the present disclosure includes a ZAP70 polypeptide. In some embodiments, the intracellular signaling domain includes a cytoplasmic signaling domain of TCR zeta, FcR gamma, FcR beta, CD3 gamma, CD3 delta, CD3 epsilon, CD5, CD22, CD79a, CD79b, or CD66d. In one embodiment, the intracellular signaling domain in the CAR includes a cytoplasmic signaling domain of human CD3 zeta.

While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The intracellular signaling domain includes any truncated portion of the intracellular signaling domain sufficient to transduce the effector function signal.

The intracellular domains described herein can be combined with any of the antigen binding domains described herein, any of the transmembrane domains described herein, or any of the other domains described herein that may be included in the CAR.

In certain embodiments, the intracellular domain comprises a costimulatory domain of 4-1BB. In certain embodiments, the costimulatory domain of 4-1BB comprises the amino acid sequence set forth in SEQ ID NO: 36. In certain embodiments, the intracellular domain comprises an intracellular domain of CD3 or a variant thereof. In certain embodiments, the intracellular domain of CD3 comprises the amino acid sequence set forth in SEQ ID NO: 37. In certain embodiments, the intracellular domain comprises 4-1BB and CD3ζ. In certain embodiments, the intracellular domain comprises the amino acid sequences set forth in SEQ ID NO: 36 and SEQ ID NO: 37.

Tolerable variations of the individual CAR domain sequences (leader, hinge, transmembrane, and intracellular domains) will be known to those of skill in the art. For example, in certain embodiments the CAR domain comprises an amino acid sequence that has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any of the amino acid sequences set forth in SEQ ID NOs. 33-37.

In one aspect, the invention provides a chimeric antigen receptor (CAR) comprising an antigen binding domain capable of binding the IIICS domain of fibronectin, a transmembrane domain, and an intracellular domain (e.g. FDC-6 CAR). In certain embodiments, the CAR comprises the amino acid sequence set forth in SEQ ID NO: 38 or SEQ ID NO: 39.

In another aspect, the invention provides a chimeric antigen receptor (CAR) comprising an antigen binding domain capable of binding the EDB domain of fibronectin, a transmembrane domain, and an intracellular domain (e.g. L19 CAR or C6 CAR). In certain embodiments, the CAR comprises the amino acid sequence set forth in SEQ ID NO: 40, SEQ ID NO: 41, SEQ ID NO: 42 or SEQ ID NO: 43.

Tolerable variations of the CAR sequences will be known to those of skill in the art. For example, in certain embodiments the CAR comprises an amino acid sequence that has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any of the amino acid sequences set forth in SEQ ID NOs. 38-43.

TABLE 1

Nucleotide and amino acid sequences

| SEQ ID NO: | | |
|---|---|---|
| 1 | FDC-6 HCDR1 | FSLSTSGMGVG |
| 2 | FDC-6 HCDR2 | WLAHIWWDDTRRY |
| 3 | FDC-6 HCDR3 | ARMNGNYPAWFAY |
| 4 | FDC-6 LCDR1 | QNIVHSNGNTYLE |
| 5 | FDC-6 LCDR2 | LLIYKVSNRFS |
| 6 | FDC-6 LCDR3 | FQGSHIPP |
| 7 | FDC-6 VH | QVTLKESGPGILQPSQTLSLTCSFSGFSLSTSGMGVGWIRQPSGKGLE WLAHIWWDDTRRYNPALKSRLTISNDTSNNQVFLKIASVDTADTAT YYCARMNGNYPAWFAYWGQGTLVTVSS |
| 8 | FDC-6 VL | DVLMTQTPLSLPVSLGDQASISCRSSQNIVHSNGNTYLEWYLLKPGQ SPKLLIYKVSNRFSGVPDRFSGSGSGTDFTLKISRVEAEDLGIYYCFQG SHIPPTFGGGTKLEIK |
| 9 | linker | GGGGSGGGGSGGGGS |
| 10 | FDC-6 scFv (H > L) | QVTLKESGPGILQPSQTLSLTCSFSGFSLSTSGMGVGWIRQPSGKGLE WLAHIWWDDTRRYNPALKSRLTISNDTSNNQVFLKIASVDTADTAT YYCARMNGNYPAWFAYWGQGTLVTVSSGGGGSGGGGSGGGGSDV LMTQTPLSLPVSLGDQASISCRSSQNIVHSNGNTYLEWYLLKPGQSPK LLIYKVSNRFSGVPDRFSGSGSGTDFTLKISRVEAEDLGIYYCFQGSHI PPTFGGGTKLEIK |
| 11 | FDC-6 scFv (L > H) | DVLMTQTPLSLPVSLGDQASISCRSSQNIVHSNGNTYLEWYLLKPGQ SPKLLIYKVSNRFSGVPDRFSGSGSGTDFTLKISRVEAEDLGIYYCFQG |

TABLE 1-continued

| Nucleotide and amino acid sequences | | |
|---|---|---|
| SEQ ID NO: | | |
| | | SHIPPTFGGGTKLEIKGGGGSGGGGSGGGGSQVTLKESGPGILQPSQT LSLTCSFSGFSLSTSGMGVGWIRQPSGKGLEWLAHIWWDDTRRYNP ALKSRLTISNDTSNNQVFLKIASVDTADTATYYCARMNGNYPAWFA YWGQGTLVTVSS |
| 12 | C6 HCDR1 | LTFNTYAMN |
| 13 | C6 HCDR2 | WVARIRSKSNNYATYY |
| 14 | C6 HCDR3 | KQGGNSLYWYFDV |
| 15 | C6 LCDR1 | QSLLYSSNQKNYLA |
| 16 | C6 LCDR2 | LLIYWASTGES |
| 17 | C6 LCDR3 | QQYYSYPL |
| 18 | C6 VH | EVQLVESGGGLVQPKGSLKISCAASGLTFNTYAMNWVRQAPRKGLE WVARIRSKSNNYATYYADSVKDRFTISRDDSQSMLYLQMNNLKTED TAMYYCVKQGGNSLYWYFDVWGAGTTVTVSS |
| 19 | C6 VL | DIVMSQSPSSLAVSVGEKVTMSCKSSQSLLYSSNQKNYLAWYQQRP GQSPKLLIYWASTGESGVPDRFTGSGSGTDFTLTISSVKAEDLAVYYC QQYYSYPLTFGAGTKLELK |
| 20 | linker | GSTSGSGKPGSGEGSSKG |
| 21 | C6 scFv (H > L) | EVQLVESGGGLVQPKGSLKISCAASGLTFNTYAMNWVRQAPRKGLE WVARIRSKSNNYATYYADSVKDRFTISRDDSQSMLYLQMNNLKTED TAMYYCVKQGGNSLYWYFDVWGAGTTVTVSSSGGSTSGSGKPGSG EGSSKGGSDIVMSQSPSSLAVSVGEKVTMSCKSSQSLLYSSNQKNYL AWYQQRPGQSPKLLIYWASTGESGVPDRFTGSGSGTDFTLTISSVKA EDLAVYYCQQYYSYPLTFGAGTKLELK |
| 22 | C6 scFv (L>H) | DIVMSQSPSSLAVSVGEKVTMSCKSSQSLLYSSNQKNYLAWYQQRP GQSPKLLIYWASTGESGVPDRFTGSGSGTDFTLTISSVKAEDLAVYYC QQYYSYPLTFGAGTKLELKGSTSGSGKPGSGEGSSKGEVQLVESGGG LVQPKGSLKISCAASGLTFNTYAMNWVRQAPRKGLEWVARIRSKSN NYATYYADSVKDRFTISRDDSQSMLYLQMNNLKTEDTAMYYCVKQ GGNSLYWYFDVWGAGTTVTVSS |
| 23 | L19 HCDR1 | FTFSSFSMS |
| 24 | L19 HCDR2 | WVSSISGSSGTTYY |
| 25 | L19 HCDR3 | KPFPYFDY |
| 26 | L19 LCDR1 | QSVSSSFLA |
| 27 | L19 LCDR2 | LLIYYASSRAT |
| 28 | L19 LCDR3 | QQTGRIPP |
| 29 | L19 VH | EVQLLESGGGLVQPGGSLRLSCAASGFTFSSFSMSWVRQAPGKGLE WVSSISGSSGTTYYADSVKGRFTISRDNSKNTLYLQMNSLRAEDTAV YYCAKPFPYFDYWGQGTLVTVSS |
| 30 | L19 VL | EIVLTQSPGTLSLSPGERATLSCRASQSVSSSFLAWYQQKPGQAPRLLI YYASSRATGIPDRFSGSGSGTDFTLTISRLEPEDFAVYYCQQTGRIPPT FGQGTKVEIK |
| 31 | L19 scFv (H > L) | EVQLLESGGGLVQPGGSLRLSCAASGFTFSSFSMSWVRQAPGKGLE WVSSISGSSGTTYYADSVKGRFTISRDNSKNTLYLQMNSLRAEDTAV YYCAKPFPYFDYWGQGTLVTVSSGGGGSGGGGSGGGGSEIVLTQSP GTLSLSPGERATLSCRASQSVSSSFLAWYQQKPGQAPRLLIYYASSRA TGIPDRFSGSGSGTDFTLTISRLEPEDFAVYYCQQTGRIPPTFGQGTKV EIK |
| 32 | L19 scFv (L > H) | EIVLTQSPGTLSLSPGERATLSCRASQSVSSSFLAWYQQKPGQAPRLLI YYASSRATGIPDRFSGSGSGTDFTLTISRLEPEDFAVYYCQQTGRIPPT FGQGTKVEIKGGGGSGGGGSGGGGSEVQLLESGGGLVQPGGSLRLS CAASGFTFSSFSMSWVRQAPGKGLEWVSSISGSSGTTYYADSVKGRF TISRDNSKNTLYLQMNSLRAEDTAVYYCAKPFPYFDYWGQGTLVTV SS |

TABLE 1-continued

| Nucleotide and amino acid sequences | | |
|---|---|---|
| SEQ ID NO: | | |
| 33 | CD8α Leader | MALPVTALLLPLALLLHAARP |
| 34 | CD8α Hinge | TTTPAPRPPTPAPTIASQPLSLRPEACRPAAGGAVHTRGLDFACD |
| 35 | CD8α Transmembrane | IYIWAPLAGTCGVLLLSLVITLYC |
| 36 | 4-1BB ICD | KRGRKKLLYIFKQPFMRPVQTTQEEDGCSCRFPEEEEGGCEL |
| 37 | CD3ζ | RVKFSRSADAPAYKQGQNQLYNELNLGRREEYDVLDKRRGRDPEM GGKPRRKNPQEGLYNELQKDKMAEAYSEIGMKGERRRGKGHDGLY QGLSTATKDTYDALHMQALPPR |
| 38 | FDC-6 CAR (H > L) | MALPVTALLLPLALLLHAARPGSQVTLKESGPGILQPSQTLSLTCSFS GFSLSTSGMGVGWIRQPSGKGLEWLAHIWWDDTRRYNPALKSRLTI SNDTSNNQVFLKIASVDTADTATYYCARMNGNYPAWFAYWGQGTL VTVSSGGGGSGGGGSGGGGSDVLMTQTPLSLPVSLGDQASISCRSSQ NIVHSNGNTYLEWYLLKPGQSPKLLIYKVSNRFSGVPDRFSGSGSGT DFTLKISRVEAEDLGIYYCFQGSHIPPTFGGGTKLEIKSGTTTPAPRPPT PAPTIASQPLSLRPEACRPAAGGAVHTRGLDFACDIYIWAPLAGTCGV LLLSLVITLYCKRGRKKLLYIFKQPFMRPVQTTQEEDGCSCRFPEEEE GGCELRVKFSRSADAPAYKQGQNQLYNELNLGRREEYDVLDKRRG RDPEMGGKPRRKNPQEGLYNELQKDKMAEAYSEIGMKGERRRGKG HDGLYQGLSTATKDTYDALHMQALPPR |
| 39 | FDC-6 CAR (L > H) | MALPVTALLLPLALLLHAARPGSDVLMTQTPLSLPVSLGDQASISCRS SQNIVHSNGNTYLEWYLLKPGQSPKLLIYKVSNRFSGVPDRFSGSGS GTDFTLKISRVEAEDLGIYYCFQGSHIPPTFGGGTKLEIKGGGGSGGG GSGGGGSQVTLKESGPGILQPSQTLSLTCSFSGFSLSTSGMGVGWIRQ PSGKGLEWLAHIWWDDTRRYNPALKSRLTISNDTSNNQVFLKIASVD TADTATYYCARMNGNYPAWFAYWGQGTLVTVSSSGTTTPAPRPPTP APTIASQPLSLRPEACRPAAGGAVHTRGLDFACDIYIWAPLAGTCGV LLLSLVITLYCKRGRKKLLYIFKQPFMRPVQTTQEEDGCSCRFPEEEE GGCELRVKFSRSADAPAYKQGQNQLYNELNLGRREEYDVLDKRRG RDPEMGGKPRRKNPQEGLYNELQKDKMAEAYSEIGMKGERRRGKG HDGLYQGLSTATKDTYDALHMQALPPR |
| 40 | C6 CAR (H > L) | MALPVTALLLPLALLLHAARPGSEVQLVESGGGLVQPKGSLKISCAA SGLTFNTYAMNWVRQAPRKGLEWVARIRSKSNNYATYYADSVKDR FTISRDDSQSMLYLQMNNLKTEDTAMYYCVKQGGNSLYWYFDVW GAGTTVTVSSSGGSTSGSGKPGSGEGSSKGGSDIVMSQSPSSLAVSVG EKVTMSCKSSQSLLYSSNQKNYLAWYQQRPGQSPKLLIYWASTGES GVPDRFTGSGSGTDFTLTISSVKAEDLAVYYCQQYYSYPLTFGAGTK LELKSGTTTPAPRPPTPAPTIASQPLSLRPEACRPAAGGAVHTRGLDF ACDIYIWAPLAGTCGVLLLSLVITLYCKRGRKKLLYIFKQPFMRPVQT TQEEDGCSCRFPEEEEGGCELRVKFSRSADAPAYKQGQNQLYNELNL GRREEYDVLDKRRGRDPEMGGKPRRKNPQEGLYNELQKDKMAEAY SEIGMKGERRRGKGHDGLYQGLSTATKDTYDALHMQALPPR |
| 41 | C6 CAR (L > H) | MALPVTALLLPLALLLHAARPGSDIVMSQSPSSLAVSVGEKVTMSCK SSQSLLYSSNQKNYLAWYQQRPGQSPKLLIYWASTGESGVPDRFTGS GSGTDFTLTISSVKAEDLAVYYCQQYYSYPLTFGAGTKLELKGSTSG SGKPGSGEGSSKGEVQLVESGGGLVQPKGSLKISCAASGLTFNTYAM NWVRQAPRKGLEWVARIRSKSNNYATYYADSVKDRFTISRDDSQSM LYLQMNNLKTEDTAMYYCVKQGGNSLYWYFDVWGAGTTVTVSSS GTTTPAPRPPTPAPTIASQPLSLRPEACRPAAGGAVHTRGLDFACDIYI WAPLAGTCGVLLLSLVITLYCKRGRKKLLYIFKQPFMRPVQTTQEED GCSCRFPEEEEGGCELRVKFSRSADAPAYKQGQNQLYNELNLGRREE YDVLDKRRGRDPEMGGKPRRKNPQEGLYNELQKDKMAEAYSEIGM KGERRRGKGHDGLYQGLSTATKDTYDALHMQALPPR |
| 42 | L19 CAR (H > L) | MALPVTALLLPLALLLHAARPGSEVQLLESGGGLVQPGGSLRLSCAA SGFTFSSFSMSWVRQAPGKGLEWVSSISGSSGTTYYADSVKGRFTISR DNSKNTLYLQMNSLRAEDTAVYYCAKPFPYFDYWGQGTLVTVSSG GGGSGGGGSGGGGSEIVLTQSPGTLSLSPGERATLSCRASQSVSSSFL AWYQQKPGQAPRLLIYYASSRATGIPDRFSGSGSGTDFTLTISRLEPE DFAVYYCQQTGRIPPTFGQGTKVEIKSGTTTPAPRPPTPAPTIASQPLS LRPEACRPAAGGAVHTRGLDFACDIYIWAPLAGTCGVLLLSLVITLY CKRGRKKLLYIFKQPFMRPVQTTQEEDGCSCRFPEEEEGGCELRVKF SRSADAPAYKQGQNQLYNELNLGRREEYDVLDKRRGRDPEMGGKP RRKNPQEGLYNELQKDKMAEAYSEIGMKGERRRGKGHDGLYQGLS TATKDTYDALHMQALPPR |

TABLE 1-continued

| SEQ ID NO: | Nucleotide and amino acid sequences | |
|---|---|---|
| 43 | L19 CAR (L > H) | MALPVTALLLPLALLLHAARPGSEIVLTQSPGTLSLSPGERATLSCRA SQSVSSSFLAWYQQKPGQAPRLLIYYASSRATGIPDRFSGSGSGTDFT LTISRLEPEDFAVYYCQQTGRIPPTFGQGTKVEIKGGGGSGGGGSGGG GSEVQLLESGGGLVQPGGSLRLSCAASGFTFSSFSMSWVRQAPGKGL EWVSSISGSSGTTYYADSVKGRFTISRDNSKNTLYLQMNSLRAEDTA VYYCAKPFPYFDYWGQGTLVTVSSSGTTTPAPRPPTPAPTIASQPLSL RPEACRPAAGGAVHTRGLDFACDIYIWAPLAGTCGVLLLSLVITLYC KRGRKKLLYIFKQPFMRPVQTTQEEDGCSCRFPEEEEGGCELRVKFS RSADAPAYKQGQNQLYNELNLGRREEYDVLDKRRGRDPEMGGKPR RKNPQEGLYNELQKDKMAEAYSEIGMKGERRRGKGHDGLYQGLST ATKDTYDALHMQALPPR |
| 44 | FDC-6 VH nucleotide sequence | CAGGTTACTCTGAAAGAGTCTGGCCCTGGGATATTGCAGCCCTCC CAGACCCTCAGTCTGACTTGTTCTTTCTCTGGGTTCACTGAGCA CTTCTGGTATGGGTGTAGGCTGGATTCGTCAGCCTTCAGGGAAGG GTCTGGAGTGGCTGGCACACATTTGGTGGGATGATACCAGGCGCT ATAACCCAGCCCTGAAGAGCCGACTGACAATCTCCAATGATACCT CCAACAACCAGGTATTTCTCAAGATCGCCAGTGTGGACACTGCAG ATACTGCCACATACTATTGTGCTCGAATGAACGGTAACTACCCTG CCTGGTTTGCTTACTGGGGCCAAGGGACTCTGGTCACTGTCTCTTC A |
| 45 | FDC-6 VL nucleotide sequence | GATGTTTTGATGACCCAAACTCCACTCTCCCTGCCTGTCAGTCTTG GAGATCAAGCCTCCATCTCTTGCAGATCTAGTCAGAACATTGTAC ATAGTAATGGAAACACCTATTTAGAATGGTACCTGCTGAAACCAG GCCAGTCTCCAAAGCTCCTGATCTACAAAGTTTCCAACCGATTTTC TGGAGTCCCAGACAGGTTCAGTGGCAGTGGATCAGGGACAGATTT CACACTCAAGATCAGCAGAGTGGAGGCTGAGGATCTGGGAATTT ATTACTGCTTTCAAGGTTCACATATTCCTCCGACGTTCGGTGGAGG CACCAAGCTGGAAATCAAA |
| 46 | FDC-6 scFv (H > L) nucleotide sequence | CAGGTTACTCTGAAAGAGTCTGGCCCTGGGATATTGCAGCCCTCC CAGACCCTCAGTCTGACTTGTTCTTTCTCTGGGTTTTCACTGAGCA CTTCTGGTATGGGTGTAGGCTGGATTCGTCAGCCTTCAGGGAAGG GTCTGGAGTGGCTGGCACACATTTGGTGGGATGATACCAGGCGCT ATAACCCAGCCCTGAAGAGCCGACTGACAATCTCCAATGATACCT CCAACAACCAGGTATTTCTCAAGATCGCCAGTGTGGACACTGCAG ATACTGCCACATACTATTGTGCTCGAATGAACGGTAACTACCCTG CCTGGTTTGCTTACTGGGGCCAAGGGACTCTGGTCACTGTCTCTTC AGGTGGCGGAGGGAGCGGCGGTGGAGGAAGCGGAGGCGGAGGT TCCGATGTTTTGATGACCCAAACTCCACTCTCCCTGCCTGTCAGTC TTGGAGATCAAGCCTCCATCTCTTGCAGATCTAGTCAGAACATTG TACATAGTAATGGAAACACCTATTTAGAATGGTACCTGCTGAAAC CAGGCCAGTCTCCAAAGCTCCTGATCTACAAAGTTTCCAACCGAT TTTCTGGAGTCCCAGACAGGTTCAGTGGCAGTGGATCAGGGACAG ATTTCACACTCAAGATCAGCAGAGTGGAGGCTGAGGATCTGGGA ATTTATTACTGCTTTCAAGGTTCACATATTCCTCCGACGTTCGGTG GAGGCACCAAGCTGGAAATCAAA |
| 47 | FDC-6 scFv (L > H) nucleotide sequence | GATGTTTTGATGACCCAAACTCCACTCTCCCTGCCTGTCAGTCTTG GAGATCAAGCCTCCATCTCTTGCAGATCTAGTCAGAACATTGTAC ATAGTAATGGAAACACCTATTTAGAATGGTACCTGCTGAAACCAG GCCAGTCTCCAAAGCTCCTGATCTACAAAGTTTCCAACCGATTTTC TGGAGTCCCAGACAGGTTCAGTGGCAGTGGATCAGGGACAGATTT CACACTCAAGATCAGCAGAGTGGAGGCTGAGGATCTGGGAATTT ATTACTGCTTTCAAGGTTCACATATTCCTCCGACGTTCGGTGGAGG CACCAAGCTGGAAATCAAAGGTGGCGGAGGGAGCGGCGGTGGAG GAAGCGGAGGCGGAGGTTCCCAGGTTACTCTGAAAGAGTCTGGC CCTGGGATATTGCAGCCCTCCCAGACCCTCAGTCTGACTTGTTCTT TCTCTGGGTTTTCACTGAGCACTTCTGGTATGGGTGTAGGCTGGAT TCGTCAGCCTTCAGGGAAGGGTCTGGAGTGGCTGGCACACATTTG GTGGGATGATACCAGGCGCTATAACCCAGCCCTGAAGAGCCGACT GACAATCTCCAATGATACCTCCAACAACCAGGTATTTCTCAAGAT CGCCAGTGTGGACACTGCAGATACTGCCACATACTATTGTGCTCG AATGAACGGTAACTACCCTGCCTGGTTTGCTTACTGGGGCCAAGG GACTCTGGTCACTGTCTCTTCA |
| 48 | FDC-6 CAR (H > L) nucleotide sequence | ATGGCCTTACCAGTGACCGCCTTGCTCCTGCCGCTGGCCTTGCTGC TCCACGCCGCCAGGCCGGGATCCCAGGTTACTCTGAAAGAGTCTG GCCCTGGGATATTGCAGCCCTCCCAGACCCTCAGTCTGACTTGTTC TTTCTCTGGGTTTTCACTGAGCACTTCTGGTATGGGTGTAGGCTGG ATTCGTCAGCCTTCAGGGAAGGGTCTGGAGTGGCTGGCACACATT TGGTGGGATGATACCAGGCGCTATAACCCAGCCCTGAAGAGCCG ACTGACAATCTCCAATGATACCTCCAACAACCAGGTATTTCTCAA |

TABLE 1-continued

| Nucleotide and amino acid sequences | | |
|---|---|---|
| SEQ ID NO: | | |
| | | GATCGCCAGTGTGGACACTGCAGATACTGCCACATACTATTGTGC<br>TCGAATGAACGGTAACTACCCTGCCTGGTTTGCTTACTGGGGCCA<br>AGGGACTCTGGTCACTGTCTCTTCAGGTGGCGGAGGGAGCGGCGG<br>TGGAGGAAGCGGAGGCGGAGGTTCCGATGTTTTGATGACCCAAA<br>CTCCACTCTCCCTGCCTGTCAGTCTTGGAGATCAAGCCTCCATCTC<br>TTGCAGATCTAGTCAGAACATTGTACATAGTAATGGAAACACCTA<br>TTTAGAATGGTACCTGCTGAAACCAGGCCAGTCTCCAAAGCTCCT<br>GATCTACAAAGTTTCCAACCGATTTTCTGGAGTCCCAGACAGGTT<br>CAGTGGCAGTGGATCAGGGACAGATTTCACACTCAAGATCAGCA<br>GAGTGGAGGCTGAGGATCTGGGAATTTATTACTGCTTTCAAGGTT<br>CACATATTCCTCCGACGTTCGGTGGAGGCACCAAGCTGGAAATCA<br>AATCCGGAACCACGACGCCAGCGCCGCGACCACCAACACCGGCG<br>CCCACCATCGCGTCGCAGCCCCTGTCCCTGCGCCCAGAGGCGTGC<br>CGGCCAGCGGCGGGGGGCGCAGTGCACACGAGGGGGCTGGACTT<br>CGCCTGTGATATCTACATCTGGGCGCCCTTGGCCGGGACTTGTGG<br>GGTCCTTCTCCTGTCACTGGTTATCACCCTTTACTGCAAACGGGGC<br>AGAAAGAAACTCCTGTATATATTCAAACAACCATTTATGAGACCA<br>GTACAAACTACTCAAGAGGAAGATGGCTGTAGCTGCCGATTTCCA<br>GAAGAAGAAGAAGGAGGATGTGAACTGAGAGTGAAGTTCAGCAG<br>GAGCGCAGACGCCCCCGCGTACAAGCAGGGCCAGAACCAGCTCT<br>ATAACGAGCTCAATCTAGGACGAAGAGAGGAGTACGATGTTTTG<br>GACAAGAGACGTGGCCGGGACCCTGAGATGGGGGGAAAGCCGAG<br>AAGGAAGAACCCTCAGGAAGGCCTGTACAATGAACTGCAGAAAG<br>ATAAGATGGCGGAGGCCTACAGTGAGATTGGGATGAAAGGCGAG<br>CGCCGGAGGGGCAAGGGGCACGATGGCCTTTACCAGGGTCTCAG<br>TACAGCCACCAAGGACACCTACGACGCCCTTCACATGCAGGCCCT<br>GCCCCCTCGC |
| 49 | FDC-6 CAR (L > H) nucleotide sequence | ATGGCCTTACCAGTGACCGCCTTGCTCCTGCCGCTGGCCTTGCTGC<br>TCCACGCCGCCAGGCCGGGATCCGATGTTTTGATGACCCAAACTC<br>CACTCTCCCTGCCTGTCAGTCTTGGAGATCAAGCCTCCATCTCTTG<br>CAGATCTAGTCAGAACATTGTACATAGTAATGGAAACACCTATTT<br>AGAATGGTACCTGCTGAAACCAGGCCAGTCTCCAAAGCTCCTGAT<br>CTACAAAGTTTCCAACCGATTTTCTGGAGTCCCAGACAGGTTCAG<br>TGGCAGTGGATCAGGGACAGATTTCACACTCAAGATCAGCAGAGT<br>GGAGGCTGAGGATCTGGGAATTTATTACTGCTTTCAAGGTTCACA<br>TATTCCTCCGACGTTCGGTGGAGGCACCAAGCTGGAAATCAAAGG<br>TGGCGGAGGGAGCGGCGGTGGAGGAAGCGGAGGCGGAGGTTCCC<br>AGGTTACTCTGAAAGAGTCTGGCCCTGGGATATTGCAGCCCTCCC<br>AGACCCTCAGTCTGACTTGTTCTTTCTCTGGGTTTTCACTGAGCAC<br>TTCTGGTATGGGTGTAGGCTGGATTCGTCAGCCTTCAGGGAAGGG<br>TCTGGAGTGGCTGGCACACATTTGGTGGGATGATACCAGGCGCTA<br>TAACCCAGCCCTGAAGAGCCGACTGACAATCTCCAATGATACCTC<br>CAACAACCAGGTATTTCTCAAGATCGCCAGTGTGGACACTGCAGA<br>TACTGCCACATACTATTGTGCTCGAATGAACGGTAACTACCCTGC<br>CTGGTTTGCTTACTGGGGCCAAGGGACTCTGGTCACTGTCTCTTCA<br>TCCGGAACCACGACGCCAGCGCCGCGACCACCAACACCGGCGCC<br>CACCATCGCGTCGCAGCCCCTGTCCCTGCGCCCAGAGGCGTGCCG<br>GCCAGCGGCGGGGGGCGCAGTGCACACGAGGGGGCTGGACTTCG<br>CCTGTGATATCTACATCTGGGCGCCCTTGGCCGGGACTTGTGGGG<br>TCCTTCTCCTGTCACTGGTTATCACCCTTTACTGCAAACGGGGCAG<br>AAAGAAACTCCTGTATATATTCAAACAACCATTTATGAGACCAGT<br>ACAAACTACTCAAGAGGAAGATGGCTGTAGCTGCCGATTTCCAGA<br>AGAAGAAGAAGGAGGATGTGAACTGAGAGTGAAGTTCAGCAGGA<br>GCGCAGACGCCCCCGCGTACAAGCAGGGCCAGAACCAGCTCTAT<br>AACGAGCTCAATCTAGGACGAAGAGAGGAGTACGATGTTTTGGA<br>CAAGAGACGTGGCCGGGACCCTGAGATGGGGGGAAAGCCGAGAA<br>GGAAGAACCCTCAGGAAGGCCTGTACAATGAACTGCAGAAAGAT<br>AAGATGGCGGAGGCCTACAGTGAGATTGGGATGAAAGGCGAGCG<br>CCGGAGGGGCAAGGGGCACGATGGCCTTTACCAGGGTCTCAGTA<br>CAGCCACCAAGGACACCTACGACGCCCTTCACATGCAGGCCCTGC<br>CCCCTCGC |
| 50 | C6 VH nucleotide sequence | GAGGTCCAATTGGTAGAGAGTGGCGGCGGCCTCGTCCAGCCAAA<br>AGGTTCCTTGAAGATAAGCTGTGCCGCATCAGGACTGACGTTCAA<br>CACCTATGCCATGAACTGGGTCCGGCAGGCACCACGCAAGGGCCT<br>TGAGTGGGTCGCAAGAATAAGGTCTAAGTCCAATAACTACGCGAC<br>TTACTACGCGGATAGTGTAAAGGATCGCTTCACAATATCACGCGA<br>CGACTCACAATCAATGTTGTATCTCCAGATGAATAACCTTAAGAC<br>AGAGGACACTGCTATGTATTATTGCGTGAAGCAAGGCGGGAACTC<br>ACTTTATTGGTACTTTGATGTCTGGGGCGCGGGCACGACGGTCAC<br>CGTTTCTTCC |

TABLE 1-continued

Nucleotide and amino acid sequences

| SEQ ID NO: | | |
|---|---|---|
| 51 | C6 VL nucleotide sequence | GATATAGTGATGAGTCAGAGTCCAAGCTCCTTGGCGGTGAGTGTC GGGGAGAAGGTCACTATGAGCTGCAAGTCCAGTCAATCCTTGCTC TATTCTTCTAACCAAAAAAATTATTTGGCCTGGTATCAACAAAGA CCTGGTCAGTCTCCCAAACTTTTGATATATTGGGCATCTACCGGCG AATCTGGCGTTCCTGACAGGTTTACCGGGAGTGGGTCAGGAACTG ACTTCACTCTCACGATCTCTAGTGTCAAAGCCGAAGATTTGGCCG TCTATTACTGTCAGCAATATTACTCCTATCCTCTGACCTTTGGCGC TGGCACAAAGTTGGAGCTTAAG |
| 52 | C6 scFv (H > L) nucleotide sequence | GAGGTCCAATTGGTAGAGAGTGGCGGCGGCCTCGTCCAGCCAAA AGGTTCCTTGAAGATAAGCTGTGCCGCATCAGGACTGACGTTCAA CACCTATGCCATGAACTGGGTCCGGCAGGCACCACGCAAGGGCCT TGAGTGGGTCGCAAGAATAAGGTCTAAGTCCAATAACTACGCGAC TTACTACGCGGATAGTGTAAAGGATCGCTTCACAATATCACGCGA CGACTCACAATCAATGTTGTATCTCCAGATGAATAACCTTAAGAC AGAGGACACTGCTATGTATTATTGCGTGAAGCAAGGCGGGAACTC ACTTTATTGGTACTTTGATGTCTGGGGCGCGGGCACGACGGTCAC CGTTTCTTCCGGCAGTACCTCAGGGTCCGGCAAGCCAGGTAGTGG CGAGGGCAGCAGTAAGGGAGATATAGTGATGAGTCAGAGTCCAA GCTCCTTGGCGGTGAGTGTCGGGGAGAAGGTCACTATGAGCTGCA AGTCCAGTCAATCCTTGCTCTATTCTTCTAACCAAAAAAATTATTT GGCCTGGTATCAACAAAGACCTGGTCAGTCTCCCAAACTTTTGAT ATATTGGGCATCTACCGGCGAATCTGGCGTTCCTGACAGGTTTAC CGGGAGTGGGTCAGGAACTGACTTCACTCTCACGATCTCTAGTGT CAAAGCCGAAGATTTGGCCGTCTATTACTGTCAGCAATATTACTC CTATCCTCTGACCTTTGGCGCTGGCACAAAGTTGGAGCTTAAG |
| 53 | C6 scFv (L > H) nucleotide sequence | GATATAGTGATGAGTCAGAGTCCAAGCTCCTTGGCGGTGAGTGTC GGGGAGAAGGTCACTATGAGCTGCAAGTCCAGTCAATCCTTGCTC TATTCTTCTAACCAAAAAAATTATTTGGCCTGGTATCAACAAAGA CCTGGTCAGTCTCCCAAACTTTTGATATATTGGGCATCTACCGGCG AATCTGGCGTTCCTGACAGGTTTACCGGGAGTGGGTCAGGAACTG ACTTCACTCTCACGATCTCTAGTGTCAAAGCCGAAGATTTGGCCG TCTATTACTGTCAGCAATATTACTCCTATCCTCTGACCTTTGGCGC TGGCACAAAGTTGGAGCTTAAGGGCAGTACCTCAGGGTCCGGCA AGCCAGGTAGTGGCGAGGGCAGCAGTAAGGGAGAGGTCCAATTG GTAGAGAGTGGCGGCGGCCTCGTCCAGCCAAAAGGTTCCTTGAAG ATAAGCTGTGCCGCATCAGGACTGACGTTCAACACCTATGCCATG AACTGGGTCCGGCAGGCACCACGCAAGGGCCTTGAGTGGGTCGC AAGAATAAGGTCTAAGTCCAATAACTACGCGACTTACTACGCGGA TAGTGTAAAGGATCGCTTCACAATATCACGCGACGACTCACAATC AATGTTGTATCTCCAGATGAATAACCTTAAGACAGAGGACACTGC TATGTATTATTGCGTGAAGCAAGGCGGGAACTCACTTTATTGGTA CTTTGATGTCTGGGGCGCGGGCACGACGGTCACCGTTTCTTCC |
| 54 | C6 CAR (H > L) nucleotide sequence | ATGGCCTTACCAGTGACCGCCTTGCTCCTGCCGCTGGCCTTGCTGC TCCACGCCGCCAGGCCGGGATCCGAGGTCCAATTGGTAGAGAGTG GCGGCGGCCTCGTCCAGCCAAAAGGTTCCTTGAAGATAAGCTGTG CCGCATCAGGACTGACGTTCAACACCTATGCCATGAACTGGGTCC GGCAGGCACCACGCAAGGGCCTTGAGTGGGTCGCAAGAATAAGG TCTAAGTCCAATAACTACGCGACTTACTACGCGGATAGTGTAAAG GATCGCTTCACAATATCACGCGACGACTCACAATCAATGTTGTAT CTCCAGATGAATAACCTTAAGACAGAGGACACTGCTATGTATTAT TGCGTGAAGCAAGGCGGGAACTCACTTTATTGGTACTTTGATGTC TGGGGCGCGGGCACGACGGTCACCGTTTCTTCCGGCAGTACCTCA GGGTCCGGCAAGCCAGGTAGTGGCGAGGGCAGCAGTAAGGGAGA TATAGTGATGAGTCAGAGTCCAAGCTCCTTGGCGGTGAGTGTCGG GGAGAAGGTCACTATGAGCTGCAAGTCCAGTCAATCCTTGCTCTA TTCTTCTAACCAAAAAAATTATTTGGCCTGGTATCAACAAAGACC TGGTCAGTCTCCCAAACTTTTGATATATTGGGCATCTACCGGCGA ATCTGGCGTTCCTGACAGGTTTACCGGGAGTGGGTCAGGAACTGA CTTCACTCTCACGATCTCTAGTGTCAAAGCCGAAGATTTGGCCGTC TATTACTGTCAGCAATATTACTCCTATCCTCTGACCTTTGGCGCTG GCACAAAGTTGGAGCTTAAGTCCGGAACCACGACGCCAGCGCCG CGACCACCAACACCGGCGCCCACCATCGCGTCGCAGCCCCTGTCC CTGCGCCCAGAGGCGTGCCGGCCAGCGGCGGGGGGCGCAGTGCA CACGAGGGGGCTGGACTTCGCCTGTGATATCTACATCTGGGCGCC CTTGGCCGGGACTTGTGGGGTCCTTCTCCTGTCACTGGTTATCACC CTTTACTGCAAACGGGGCAGAAAGAAACTCCTGTATATATTCAAA CAACCATTTATGAGACCAGTACAAACTACTCAAGAGGAAGATGG CTGTAGCTGCCGATTTCCAGAAGAAGAAGAAGGAGGATGTGAAC TGAGAGTGAAGTTCAGCAGGAGCGCAGACGCCCCCGCGTACAAG CAGGGCCAGAACCAGCTCTATAACGAGCTCAATCTAGGACGAAG |

TABLE 1-continued

Nucleotide and amino acid sequences

| SEQ ID NO: | | |
|---|---|---|
| | | AGAGGAGTACGATGTTTTGGACAAGAGACGTGGCCGGGACCCTG AGATGGGGGGAAAGCCGAGAAGGAAGAACCCTCAGGAAGGCCTG TACAATGAACTGCAGAAAGATAAGATGGCGGAGGCCTACAGTGA GATTGGGATGAAAGGCGAGCGCCGGAGGGGCAAGGGGCACGATG GCCTTTACCAGGGTCTCAGTACAGCCACCAAGGACACCTACGACG CCCTTCACATGCAGGCCCTGCCCCCTCGC |
| 55 | C6 CAR (L > H) nucleotide sequence | ATGGCCTTACCAGTGACCGCCTTGCTCCTGCCGCTGGCCTTGCTGC TCCACGCCGCCAGGCCGGGATCCGATATAGTGATGAGTCAGAGTC CAAGCTCCTTGGCGGTGAGTGTCGGGGAGAAGGTCACTATGAGCT GCAAGTCCAGTCAATCCTTGCTCTATTCTTCTAACCAAAAAAATTA TTTGGCCTGGTATCAACAAAGACCTGGTCAGTCTCCCAAACTTTTG ATATATTGGGCATCTACCGGCGAATCTGGCGTTCCTGACAGGTTT ACCGGGAGTGGGTCAGGAACTGACTTCACTCTCACGATCTCTAGT GTCAAAGCCGAAGATTTGGCCGTCTATTACTGTCAGCAATATTAC TCCTATCCTCTGACCTTTGGCGCTGGCACAAAGTTGGAGCTTAAG GGCAGTACCTCAGGGTCCGGCAAGCCAGGTAGTGGCGAGGGCAG CAGTAAGGGAGAGGTCCAATTGGTAGAGAGTGGCGGCGGCCTCG TCCAGCCAAAAGGTTCCTTGAAGATAAGCTGTGCCGCATCAGGAC TGACGTTCAACACCTATGCCATGAACTGGGTCCGGCAGGCACCAC GCAAGGGCCTTGAGTGGGTCGCAAGAATAAGGTCTAAGTCCAAT AACTACGCGACTTACTACGCGGATAGTGTAAAGGATCGCTTCACA ATATCACGCGACGACTCACAATCAATGTTGTATCTCCAGATGAAT AACCTTAAGACAGAGGACACTGCTATGTATTATTGCGTGAAGCAA GGCGGGAACTCACTTTATTGGTACTTTGATGTCTGGGGCGCGGGC ACGACGGTCACCGTTTCTTCCTCCGGAACCACGACGCCAGCGCCG CGACCACCAACACCGGCGCCCACCATCGCGTCGCAGCCCCTGTCC CTGCGCCCAGAGGCGTGCCGGCCAGCGGCGGGGGGCGCAGTGCA CACGAGGGGGCTGGACTTCGCCTGTGATATCTACATCTGGGCGCC CTTGGCCGGGACTTGTGGGGTCCTTCTCCTGTCACTGGTTATCACC CTTTACTGCAAACGGGGCAGAAAGAAACTCCTGTATATATTCAAA CAACCATTTATGAGACCAGTACAAACTACTCAAGAGGAAGATGG CTGTAGCTGCCGATTTCCAGAAGAAGAAGAAGGAGGATGTGAAC TGAGAGTGAAGTTCAGCAGGAGCGCAGACGCCCCCGCGTACAAG CAGGGCCAGAACCAGCTCTATAACGAGCTCAATCTAGGACGAAG AGAGGAGTACGATGTTTTGGACAAGAGACGTGGCCGGGACCCTG AGATGGGGGGAAAGCCGAGAAGGAAGAACCCTCAGGAAGGCCTG TACAATGAACTGCAGAAAGATAAGATGGCGGAGGCCTACAGTGA GATTGGGATGAAAGGCGAGCGCCGGAGGGGCAAGGGGCACGATG GCCTTTACCAGGGTCTCAGTACAGCCACCAAGGACACCTACGACG CCCTTCACATGCAGGCCCTGCCCCCTCGC |
| 56 | L19 VH nucleotide sequence | GAGGTACAGCTCTTGGAGTCTGGGGGTGGTTTGGTTCAACCAGGT GGCTCTCTGCGCCTGTCCTGTGCGGCTTCTGGTTTTACCTTCTCTTC ATTCTCTATGTCCTGGGTTCGACAGGCACCTGGAAAGGGACTGGA GTGGGTTTCCTCTATAAGCGGCAGTTCTGGCACGACGTATTATGC CGACTCCGTCAAGGGAAGGTTCACCATTTCTCGGGATAATTCAAA GAACACACTCTACTTGCAGATGAACTCATTGAGAGCAGAAGACAC AGCAGTGTACTATTGTGCGAAGCCCTTTCCGTATTTCGATTACTGG GGCCAGGGCACATTGGTTACTGTTAGCAGT |
| 57 | L19 VL nucleotide sequence | GAGATCGTTTTGACACAATCTCCGGGCACACTCTCTCTCAGTCCA GGCGAACGCGCAACTTTGTCTTGTCGAGCCAGCCAGAGCGTTTCC TCCTCATTCCTTGCGTGGTATCAGCAGAAGCCGGGCCAGGCACCC CGCCTCCTGATTTACTACGCATCATCTAGGGCAACAGGTATTCCTG ACAGGTTCAGTGGCTCAGGCTCTGGCACAGATTTTACACTCACTA TTTCCAGATTGGAGCCAGAGGATTTTGCGGTTTACTATTGCCAGC AAACTGGGCGAATCCCACCGACATTCGGACAAGGTACGAAGGTC GAAATCAAG |
| 58 | L19 scFv (H > L) nucleotide sequence | GAGGTACAGCTCTTGGAGTCTGGGGGTGGTTTGGTTCAACCAGGT GGCTCTCTGCGCCTGTCCTGTGCGGCTTCTGGTTTTACCTTCTCTTC ATTCTCTATGTCCTGGGTTCGACAGGCACCTGGAAAGGGACTGGA GTGGGTTTCCTCTATAAGCGGCAGTTCTGGCACGACGTATTATGC CGACTCCGTCAAGGGAAGGTTCACCATTTCTCGGGATAATTCAAA GAACACACTCTACTTGCAGATGAACTCATTGAGAGCAGAAGACAC AGCAGTGTACTATTGTGCGAAGCCCTTTCCGTATTTCGATTACTGG GGCCAGGGCACATTGGTTACTGTTAGCAGTGGTGGCGGAGGGA GCGGCGGTGGAGGAAGCGGAGGCGGAGGTTCCGAGATCGTT TTGACACAATCTCCGGGCACACTCTCTCTCAGTCCAGGCGAACGC GCAACTTTGTCTTGTCGAGCCAGCCAGAGCGTTTCCTCCTCATTCC TTGCGTGGTATCAGCAGAAGCCGGGCCAGGCACCCCGCCTCCTGA TTTACTACGCATCATCTAGGGCAACAGGTATTCCTGACAGGTTCA GTGGCTCAGGCTCTGGCACAGATTTTACACTCACTATTTCCAGATT |

TABLE 1-continued

| Nucleotide and amino acid sequences | | |
|---|---|---|
| SEQ ID NO: | | |
| | | GGAGCCAGAGGATTTTGCGGTTTACTATTGCCAGCAAACTGGGCG<br>AATCCCACCGACATTCGGACAAGGTACGAAGGTCGAAATCAAG |
| 59 | L19 scFv (L > H) nucleotide sequence | GAGATCGTTTTGACACAATCTCCGGGCACACTCTCTCTCAGTCCA<br>GGCGAACGCGCAACTTTGTCTTGTCGAGCCAGCCAGAGCGTTTCC<br>TCCTCATTCCTTGCGTGGTATCAGCAGAAGCCGGGCCAGGCACCC<br>CGCCTCCTGATTTACTACGCATCATCTAGGGCAACAGGTATTCCTG<br>ACAGGTTCAGTGGCTCAGGCTCTGGCACAGATTTTACACTCACTA<br>TTTCCAGATTGGAGCCAGAGGATTTTGCGGTTTACTATTGCCAGC<br>AAACTGGGCGAATCCCACCGACATTCGGACAAGGTACGAAGGTC<br>GAAATCAAGGGTGGCGGAGGGAGCGGCGGTGGAGGAAGCG<br>GAGGCGGAGGTTCCGAGGTACAGCTCTTGGAGTCTGGGGGTGG<br>TTTGGTTCAACCAGGTGGCTCTCTGCGCCTGTCCTGTGCGGCTTCT<br>GGTTTTACCTTCTCTTCATTCTCTATGTCCTGGGTTCGACAGGCAC<br>CTGGAAAGGGACTGGAGTGGGTTTCCTCTATAAGCGGCAGTTCTG<br>GCACGACGTATTATGCCGACTCCGTCAAGGGAAGGTTCACCATTT<br>CTCGGGATAATTCAAAGAACACACTCTACTTGCAGATGAACTCAT<br>TGAGAGCAGAAGACACAGCAGTGTACTATTGTGCGAAGCCCTTTC<br>CGTATTTCGATTACTGGGGCCAGGGCACATTGGTTACTGTTAGCA<br>GT |
| 60 | L19 CAR (H > L) nucleotide sequence | ATGGCCTTACCAGTGACCGCCTTGCTCCTGCCGCTGGCCTTGCTGC<br>TCCACGCCGCCAGGCCGGGATCCGAGGTACAGCTCTTGGAGTCTG<br>GGGGTGGTTTGGTTCAACCAGGTGGCTCTCTGCGCCTGTCCTGTGC<br>GGCTTCTGGTTTTACCTTCTCTTCATTCTCTATGTCCTGGGTTCGAC<br>AGGCACCTGGAAAGGGACTGGAGTGGGTTTCCTCTATAAGCGGCA<br>GTTCTGGCACGACGTATTATGCCGACTCCGTCAAGGGAAGGTTCA<br>CCATTTCTCGGGATAATTCAAAGAACACACTCTACTTGCAGATGA<br>ACTCATTGAGAGCAGAAGACACAGCAGTGTACTATTGTGCGAAGC<br>CCTTTCCGTATTTCGATTACTGGGGCCAGGGCACATTGGTTACTGT<br>TAGCAGTGGTGGCGGAGGGAGCGGCGGTGGAGGAAGCGGA<br>GGCGGAGGTTCCGAGATCGTTTTGACACAATCTCCGGGCACACT<br>CTCTCTCAGTCCAGGCGAACGCGCAACTTTGTCTTGTCGAGCCAG<br>CCAGAGCGTTTCCTCCTCATTCCTTGCGTGGTATCAGCAGAAGCC<br>GGGCCAGGCACCCCGCCTCCTGATTTACTACGCATCATCTAGGGC<br>AACAGGTATTCCTGACAGGTTCAGTGGCTCAGGCTCTGGCACAGA<br>TTTTACACTCACTATTTCCAGATTGGAGCCAGAGGATTTTGCGGTT<br>TACTATTGCCAGCAAACTGGGCGAATCCCACCGACATTCGGACAA<br>GGTACGAAGGTCGAAATCAAGTCCGGAACCACGACGCCAGCGCC<br>GCGACCACCAACACCGGCGCCCACCATCGCGTCGCAGCCCCTGTC<br>CCTGCGCCCAGAGGCGTGCCGGCCAGCGGCGGGGGGCGCAGTGC<br>ACACGAGGGGGCTGGACTTCGCCTGTGATATCTACATCTGGGCGC<br>CCTTGGCCGGGACTTGTGGGGTCCTTCTCCTGTCACTGGTTATCAC<br>CCTTTACTGCAAACGGGGCAGAAAGAAACTCCTGTATATATTCAA<br>ACAACCATTTATGAGACCAGTACAAACTACTCAAGAGGAAGATG<br>GCTGTAGCTGCCGATTTCCAGAAGAAGAAGAAGGAGGATGTGAA<br>CTGAGAGTGAAGTTCAGCAGGAGCGCAGACGCCCCCGCGTACAA<br>GCAGGGCCAGAACCAGCTCTATAACGAGCTCAATCTAGGACGAA<br>GAGAGGAGTACGATGTTTTGGACAAGAGACGTGGCCGGGACCCT<br>GAGATGGGGGGAAAGCCGAGAAGGAAGAACCCTCAGGAAGGCCT<br>GTACAATGAACTGCAGAAAGATAAGATGGCGGAGGCCTACAGTG<br>AGATTGGGATGAAAGGCGAGCGCCGGAGGGGCAAGGGGCACGAT<br>GGCCTTTACCAGGGTCTCAGTACAGCCACCAAGGACACCTACGAC<br>GCCCTTCACATGCAGGCCCTGCCCCCTCGC |
| 61 | L19 CAR (L > H) nucleotide sequence | ATGGCCTTACCAGTGACCGCCTTGCTCCTGCCGCTGGCCTTGCTGC<br>TCCACGCCGCCAGGCCGGGATCCGAGATCGTTTTGACACAATCTC<br>CGGGCACACTCTCTCTCAGTCCAGGCGAACGCGCAACTTTGTCTT<br>GTCGAGCCAGCCAGAGCGTTTCCTCCTCATTCCTTGCGTGGTATCA<br>GCAGAAGCCGGGCCAGGCACCCCGCCTCCTGATTTACTACGCATC<br>ATCTAGGGCAACAGGTATTCCTGACAGGTTCAGTGGCTCAGGCTC<br>TGGCACAGATTTTACACTCACTATTTCCAGATTGGAGCCAGAGGA<br>TTTTGCGGTTTACTATTGCCAGCAAACTGGGCGAATCCCACCGAC<br>ATTCGGACAAGGTACGAAGGTCGAAATCAAGGGTGGCGGAGGG<br>AGCGGCGGTGGAGGAAGCGGAGGCGGAGGTTCCGAGGTACA<br>GCTCTTGGAGTCTGGGGGTGGTTTGGTTCAACCAGGTGGCTCTCT<br>GCGCCTGTCCTGTGCGGCTTCTGGTTTTACCTTCTCTTCATTCTCTA<br>TGTCCTGGGTTCGACAGGCACCTGGAAAGGGACTGGAGTGGGTTT<br>CCTCTATAAGCGGCAGTTCTGGCACGACGTATTATGCCGACTCCG<br>TCAAGGGAAGGTTCACCATTTCTCGGGATAATTCAAAGAACACAC<br>TCTACTTGCAGATGAACTCATTGAGAGCAGAAGACACAGCAGTGT<br>ACTATTGTGCGAAGCCCTTTCCGTATTTCGATTACTGGGGCCAGG<br>GCACATTGGTTACTGTTAGCAGTTCCGGAACCACGACGCCAGCGC<br>CGCGACCACCAACACCGGCGCCCACCATCGCGTCGCAGCCCCTGT |

TABLE 1-continued

Nucleotide and amino acid sequences

| SEQ ID NO: | |
|---|---|
| | CCCTGCGCCCAGAGGCGTGCCGGCCAGCGGCGGGGGGCGCAGTG<br>CACACGAGGGGGCTGGACTTCGCCTGTGATATCTACATCTGGGCG<br>CCCTTGGCCGGGACTTGTGGGGTCCTTCTCCTGTCACTGGTTATCA<br>CCCTTTACTGCAAACGGGGCAGAAAGAAACTCCTGTATATATTCA<br>AACAACCATTTATGAGACCAGTACAAACTACTCAAGAGGAAGAT<br>GGCTGTAGCTGCCGATTTCCAGAAGAAGAAGAAGGAGGATGTGA<br>ACTGAGAGTGAAGTTCAGCAGGAGCGCAGACGCCCCCGCGTACA<br>AGCAGGGCCAGAACCAGCTCTATAACGAGCTCAATCTAGGACGA<br>AGAGAGGAGTACGATGTTTTGGACAAGAGACGTGGCCGGGACCC<br>TGAGATGGGGGGAAAGCCGAGAAGGAAGAACCCTCAGGAAGGCC<br>TGTACAATGAACTGCAGAAAGATAAGATGGCGGAGGCCTACAGT<br>GAGATTGGGATGAAAGGCGAGCGCCGGAGGGGCAAGGGGCACG<br>ATGGCCTTTACCAGGGTCTCAGTACAGCCACCAAGGACACCTACG<br>ACGCCCTTCACATGCAGGCCCTGCCCCCTCGC |

C. Nucleic Acids and Expression Vectors

The present disclosure provides a nucleic acid encoding a CAR. The nucleic acid of the present disclosure may comprises a polynucleotide sequence encoding any one of the CARs disclosed herein.

In certain aspects, the invention includes a nucleic acid comprising a polynucleotide sequence encoding a chimeric antigen receptor (CAR) capable of binding the IIICS domain of fibronectin comprising an antigen binding domain, a transmembrane domain, and an intracellular domain, wherein the antigen-binding domain comprises: a heavy chain variable region that comprises three heavy chain complementarity determining regions (HCDRs), wherein HCDR1 comprises the amino acid sequence set forth in SEQ ID NO: 1, HCDR2 comprises the amino acid sequence set forth in SEQ ID NO: 2, and HCDR3 comprises the amino acid sequence set forth in SEQ ID NO: 3; and a light chain variable region that comprises three light chain complementarity determining regions (LCDRs), wherein LCDR1 comprises the amino acid sequence set forth in SEQ ID NO: 4, LCDR2 comprises the amino acid sequence set forth in SEQ ID NO: 5, and LCDR3 comprises the amino acid sequence set forth in SEQ ID NO: 6.

In certain embodiments, the antigen binding domain comprises a heavy chain variable region encoded by a polynucleotide sequence at least 60%, 65%, 70%, 75%, 80%, 85%, 90%, 95%, 96%, 97%, 98%, 99%, or 100% identical to SEQ ID NO: 44 and/or a light chain variable region encoded by a polynucleotide sequence at least 60%, 65%, 70%, 75%, 80%, 85%, 90%, 95%, 96%, 97%, 98%, 99%, or 100% identical to SEQ ID NO: 45.

In certain embodiments, the antigen binding domain is a single-chain variable fragment (scFv) encoded by a polynucleotide sequence at least 60%, 65%, 70%, 75%, 80%, 85%, 90%, 95%, 96%, 97%, 98%, 99%, or 100% identical to SEQ ID NO: 46 or SEQ ID NO: 47.

In certain aspects, the invention includes a nucleic acid comprising a polynucleotide sequence encoding a chimeric antigen receptor (CAR) capable of binding the EDB domain of fibronectin comprising an antigen binding domain, a transmembrane domain, and an intracellular domain, wherein the antigen-binding domain comprises: a heavy chain variable region that comprises three heavy chain complementarity determining regions (HCDRs), wherein HCDR1 comprises the amino acid sequence set forth in SEQ ID NO: 12, HCDR2 comprises the amino acid sequence set forth in SEQ ID NO: 13, and HCDR3 comprises the amino acid sequence set forth in SEQ ID NO: 14; and a light chain variable region that comprises three light chain complementarity determining regions (LCDRs), wherein LCDR1 comprises the amino acid sequence set forth in SEQ ID NO: 15, LCDR2 comprises the amino acid sequence set forth in SEQ ID NO: 16, and LCDR3 comprises the amino acid sequence set forth in SEQ ID NO: 17.

In certain embodiments, the antigen binding domain comprises a heavy chain variable region encoded by a polynucleotide sequence at least 60%, 65%, 70%, 75%, 80%, 85%, 90%, 95%, 96%, 97%, 98%, 99%, or 100% identical to SEQ ID NO: 50 and/or a light chain variable region encoded by a polynucleotide sequence at least 60%, 65%, 70%, 75%, 80%, 85%, 90%, 95%, 96%, 97%, 98%, 99%, or 100% identical to SEQ ID NO: 51.

In certain embodiments, the antigen binding domain is a single-chain variable fragment (scFv) encoded by a polynucleotide sequence at least 60%, 65%, 70%, 75%, 80%, 85%, 90%, 95%, 96%, 97%, 98%, 99%, or 100% identical to SEQ ID NO: 52 or SEQ ID NO: 53.

In certain aspects, the invention includes a nucleic acid comprising a polynucleotide sequence encoding a chimeric antigen receptor (CAR) capable of binding the EDB domain of fibronectin comprising an antigen binding domain, a transmembrane domain, and an intracellular domain, wherein the antigen-binding domain comprises: a heavy chain variable region that comprises three heavy chain complementarity determining regions (HCDRs), wherein HCDR1 comprises the amino acid sequence set forth in SEQ ID NO: 23, HCDR2 comprises the amino acid sequence set forth in SEQ ID NO: 24, and HCDR3 comprises the amino acid sequence set forth in SEQ ID NO: 25; and a light chain variable region that comprises three light chain complementarity determining regions (LCDRs), wherein LCDR1 comprises the amino acid sequence set forth in SEQ ID NO: 26, LCDR2 comprises the amino acid sequence set forth in SEQ ID NO: 27, and LCDR3 comprises the amino acid sequence set forth in SEQ ID NO: 28.

In certain embodiments, the antigen binding domain comprises a heavy chain variable region encoded by a polynucleotide sequence at least 60%, 65%, 70%, 75%, 80%, 85%, 90%, 95%, 96%, 97%, 98%, 99%, or 100% identical to SEQ ID NO: 56 and/or a light chain variable region encoded by a polynucleotide sequence at least 60%, 65%, 70%, 75%, 80%, 85%, 90%, 95%, 96%, 97%, 98%, 99%, or 100% identical to SEQ ID NO: 57.

In certain embodiments, the antigen binding domain is a single-chain variable fragment (scFv) encoded by a polynucleotide sequence at least 60%, 65%, 70%, 75%, 80%, 85%, 90%, 95%, 96%, 97%, 98%, 99%, or 100% identical to SEQ ID NO: 58 or SEQ ID NO: 59.

The invention also provides a nucleic acid comprising a polynucleotide sequence encoding a chimeric antigen receptor (CAR) capable of binding the IIICS domain of fibronectin, comprising a polynucleotide sequence at least 60%, 65%, 70%, 75%, 80%, 85%, 90%, 95%, 96%, 97%, 98%, 99%, or 100% identical to SEQ ID NO: 48 or 49.

The invention also provides a nucleic acid comprising a polynucleotide sequence encoding a chimeric antigen receptor (CAR) capable of binding the EDB domain of fibronectin, comprising a polynucleotide sequence at least 60%, 65%, 70%, 75%, 80%, 85%, 90%, 95%, 96%, 97%, 98%, 99%, or 100% identical to SEQ ID NO: 54, 55, 60 or 61.

In certain embodiments, a nucleic acid of the present disclosure comprises a first polynucleotide sequence and a second polynucleotide sequence. The first and second polynucleotide sequence may be separated by a linker. A linker for use in the present disclosure allows for multiple proteins to be encoded by the same nucleic acid sequence (e.g., a multicistronic or bicistronic sequence), which are translated as a polyprotein that is dissociated into separate protein components. In certain embodiments, the nucleic acid comprises from 5' to 3' the first polynucleotide sequence, the linker, and the second polynucleotide sequence. In certain embodiments, the nucleic acid comprises from 5' to 3' the second polynucleotide sequence, the linker, and the first polynucleotide sequence.

In some embodiments, the linker comprises a nucleic acid sequence that encodes for an internal ribosome entry site (IRES). As used herein, "an internal ribosome entry site" or "IRES" refers to an element that promotes direct internal ribosome entry to the initiation codon, such as ATG, of a protein coding region, thereby leading to cap-independent translation of the gene. Various internal ribosome entry sites are known to those of skill in the art, including, without limitation, IRES obtainable from viral or cellular mRNA sources, e.g., immunogloublin heavy-chain binding protein (BiP); vascular endothelial growth factor (VEGF); fibroblast growth factor 2; insulin-like growth factor; translational initiation factor eIF4G; yeast transcription factors TFIID and HAP4; and IRES obtainable from, e.g., cardiovirus, rhinovirus, aphthovirus, HCV, Friend murine leukemia virus (FrMLV), and Moloney murine leukemia virus (MoMLV). Those of skill in the art would be able to select the appropriate IRES for use in the present invention.

In some embodiments, the linker comprises a nucleic acid sequence that encodes for a self-cleaving peptide. As used herein, a "self-cleaving peptide" or "2A peptide" refers to an oligopeptide that allow multiple proteins to be encoded as polyproteins, which dissociate into component proteins upon translation. Use of the term "self-cleaving" is not intended to imply a proteolytic cleavage reaction. Various self-cleaving or 2A peptides are known to those of skill in the art, including, without limitation, those found in members of the Picornaviridae virus family, e.g., foot-and-mouth disease virus (FMDV), equine rhinitis A virus (ERAVO, Thosea asigna virus (TaV), and porcine tescho virus-1 (PTV-1); and carioviruses such as Theilovirus and encephalomyocarditis viruses. 2A peptides derived from FMDV, ERAV, PTV-1, and TaV are referred to herein as "F2A," "E2A," "P2A," and "T2A," respectively. Those of skill in the art would be able to select the appropriate self-cleaving peptide for use in the present invention.

In some embodiments, a linker further comprises a nucleic acid sequence that encodes a furin cleavage site. Furin is a ubiquitously expressed protease that resides in the trans-golgi and processes protein precursors before their secretion. Furin cleaves at the COOH— terminus of its consensus recognition sequence. Various furin consensus recognition sequences (or "furin cleavage sites") are known to those of skill in the art, including, without limitation, Arg-X1-Lys-Arg (SEQ ID NO:117) or Arg-X1-Arg-Arg (SEQ ID NO:118), X2-Arg-X1-X3-Arg (SEQ ID NO:119) and Arg-X1-X1-Arg (SEQ ID NO:120), such as an Arg-Gln-Lys-Arg (SEQ ID NO:121), where X1 is any naturally occurring amino acid, X2 is Lys or Arg, and X3 is Lys or Arg. Those of skill in the art would be able to select the appropriate Furin cleavage site for use in the present invention.

In some embodiments, the linker comprises a nucleic acid sequence encoding a combination of a Furin cleavage site and a 2A peptide. Examples include, without limitation, a linker comprising a nucleic acid sequence encoding a Furin cleavage site and F2A, a linker comprising a nucleic acid sequence encoding a Furin cleavage site and E2A, a linker comprising a nucleic acid sequence encoding a Furin cleavage site and P2A, a linker comprising a nucleic acid sequence encoding a Furin cleavage site and T2A. Those of skill in the art would be able to select the appropriate combination for use in the present invention. In such embodiments, the linker may further comprise a spacer sequence between the Furin cleavage site and the 2A peptide. In some embodiments, the linker comprises a Furin cleavage site 5' to a 2A peptide. In some embodiments, the linker comprises a 2A peptide 5' to a Furin cleavage site. Various spacer sequences are known in the art, including, without limitation, glycine serine (GS) spacers such as $(GS)_n$, $(GSGGS)_n$ (SEQ ID NO:62) and $(GGGS)_n$ (SEQ ID NO:63), where n represents an integer of at least 1. Exemplary spacer sequences can comprise amino acid sequences including, without limitation, GGSG (SEQ ID NO:65), GGSGG (SEQ ID NO:66), GSGSG (SEQ ID NO:67), GSGGG (SEQ ID NO:68), GGGSG (SEQ ID NO:69), GSSSG (SEQ ID NO:70), and the like. Those of skill in the art would be able to select the appropriate spacer sequence for use in the present invention.

In some embodiments, a nucleic acid of the present disclosure may be operably linked to a transcriptional control element, e.g., a promoter, and enhancer, etc. Suitable promoter and enhancer elements are known to those of skill in the art.

In certain embodiments, the nucleic acid encoding an exogenous CAR is in operable linkage with a promoter. In certain embodiments, the promoter is a phosphoglycerate kinase-1 (PGK) promoter.

For expression in a bacterial cell, suitable promoters include, but are not limited to, lacI, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters. Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

In some embodiments, the promoter is a CD8 cell-specific promoter, a CD4 cell-specific promoter, a neutrophil-specific promoter, or an NK-specific promoter. For example, a CD4 gene promoter can be used; see, e.g., Salmon et al. Proc. Natl. Acad. Sci. USA (1993) 90:7739; and Marodon et al. (2003) Blood 101:3416. As another example, a CD8 gene promoter can be used. NK cell-specific expression can be achieved by use of an NcrI (p46) promoter; see, e.g., Eckelhart et al. Blood (2011) 117:1565.

For expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHOS promoter, a CUP1 promoter, a GALT promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in Pichia). Selection of the appropriate vector and promoter is well within the level of ordinary skill in the art. Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, J. Bacteriol. (1991) 173(1): 86-93; Alpuche-Aranda et al., Proc. Natl. Acad. Sci. USA (1992) 89(21): 10079-83), a nirB promoter (Harborne et al. Mol. Micro. (1992) 6:2805-2813), and the like (see, e.g., Dunstan et al., Infect. Immun. (1999) 67:5133-5141; McKelvie et al., Vaccine (2004) 22:3243-3255; and Chatfield et al., Biotechnol. (1992) 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al., Infect. Immun. (2002) 70:1087-1096); an rpsM promoter (see, e.g., Valdivia and Falkow Mol. Microbiol. (1996). 22:367); a tet promoter (see, e.g., Hillen, W. and Wissmann, A. (1989) In Saenger, W. and Heinemann, U. (eds), Topics in Molecular and Structural Biology, Protein—Nucleic Acid Interaction. Macmillan, London, UK, Vol. 10, pp. 143-162); an SP6 promoter (see, e.g., Melton et al., Nucl. Acids Res. (1984) 12:7035); and the like. Suitable strong promoters for use in prokaryotes such as *Escherichia coli* include, but are not limited to Trc, Tac, T5, T7, and PLambda. Non-limiting examples of operators for use in bacterial host cells include a lactose promoter operator (Lad repressor protein changes conformation when contacted with lactose, thereby preventing the Lad repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, e.g., deBoer et al., Proc. Natl. Acad. Sci. U.S.A. (1983) 80:21-25).

Other examples of suitable promoters include the immediate early cytomegalovirus (CMV) promoter sequence. This promoter sequence is a strong constitutive promoter sequence capable of driving high levels of expression of any polynucleotide sequence operatively linked thereto. Other constitutive promoter sequences may also be used, including, but not limited to a simian virus 40 (SV40) early promoter, a mouse mammary tumor virus (MMTV) or human immunodeficiency virus (HIV) long terminal repeat (LTR) promoter, a MoMuLV promoter, an avian leukemia virus promoter, an Epstein-Barr virus immediate early promoter, a Rous sarcoma virus promoter, the EF-1 alpha promoter, as well as human gene promoters such as, but not limited to, an actin promoter, a myosin promoter, a hemoglobin promoter, and a creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In some embodiments, the locus or construct or transgene containing the suitable promoter is irreversibly switched through the induction of an inducible system. Suitable systems for induction of an irreversible switch are well known in the art, e.g., induction of an irreversible switch may make use of a Cre-lox-mediated recombination (see, e.g., Fuhrmann-Benzakein, et al., Proc. Natl. Acad. Sci. USA (2000) 28:e99, the disclosure of which is incorporated herein by reference). Any suitable combination of recombinase, endonuclease, ligase, recombination sites, etc. known to the art may be used in generating an irreversibly switchable promoter. Methods, mechanisms, and requirements for performing site-specific recombination, described elsewhere herein, find use in generating irreversibly switched promoters and are well known in the art, see, e.g., Grindley et al. Annual Review of Biochemistry (2006) 567-605; and Tropp, Molecular Biology (2012) (Jones & Bartlett Publishers, Sudbury, Mass.), the disclosures of which are incorporated herein by reference.

In some embodiments, a nucleic acid of the present disclosure further comprises a nucleic acid sequence encoding a CAR inducible expression cassette. In one embodiment, the CAR inducible expression cassette is for the production of a transgenic polypeptide product that is released upon CAR signaling. See, e.g., Chmielewski and Abken, Expert Opin. Biol. Ther. (2015) 15(8): 1145-1154; and Abken, Immunotherapy (2015) 7(5): 535-544. In some embodiments, a nucleic acid of the present disclosure further comprises a nucleic acid sequence encoding a cytokine operably linked to a T-cell activation responsive promoter. In some embodiments, the cytokine operably linked to a T-cell activation responsive promoter is present on a separate nucleic acid sequence. In one embodiment, the cytokine is IL-12.

A nucleic acid of the present disclosure may be present within an expression vector and/or a cloning vector. An expression vector can include a selectable marker, an origin of replication, and other features that provide for replication and/or maintenance of the vector. Suitable expression vectors include, e.g., plasmids, viral vectors, and the like. Large numbers of suitable vectors and promoters are known to those of skill in the art; many are commercially available for generating a subject recombinant construct. The following vectors are provided by way of example, and should not be construed in anyway as limiting: Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus (see, e.g., Li et al., Invest. Opthalmol. Vis. Sci. (1994) 35: 2543-2549; Borras et al., Gene Ther. (1999) 6: 515-524; Li and Davidson, Proc. Natl. Acad. Sci. USA (1995) 92: 7700-7704; Sakamoto et al., H. Gene Ther. (1999) 5: 1088-1097; WO 94/12649, WO 93/03769; WO 93/19191; WO 94/28938; WO 95/11984 and WO 95/00655); adeno-associated virus (see, e.g., Ali et al., Hum. Gene Ther. (1998) 9: 81-86, Flannery et al., Proc. Natl. Acad. Sci. USA (1997) 94: 6916-6921; Bennett et al., Invest. Opthalmol. Vis. Sci. (1997) 38: 2857-2863; Jomary et al., Gene Ther. (1997) 4:683 690, Rolling et al., Hum. Gene Ther. (1999) 10: 641-648; Ali et al., Hum. Mol. Genet. (1996) 5: 591-594; Srivastava in WO 93/09239, Samulski et al., J. Vir. (1989) 63: 3822-3828; Mendelson et al., Virol. (1988) 166: 154-165; and Flotte et al., Proc. Natl. Acad. Sci. USA (1993) 90: 10613-10617); SV40; herpes simplex virus; human immunodeficiency virus (see, e.g., Miyoshi et al., Proc. Natl. Acad. Sci. USA (1997) 94: 10319-23; Takahashi et al., J. Virol. (1999) 73: 7812-7816); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

Additional expression vectors suitable for use are, e.g., without limitation, a lentivirus vector, a gamma retrovirus vector, a foamy virus vector, an adeno-associated virus vector, an adenovirus vector, a pox virus vector, a herpes virus vector, an engineered hybrid virus vector, a transposon mediated vector, and the like. Viral vector technology is well known in the art and is described, for example, in Sambrook et al., 2012, Molecular Cloning: A Laboratory Manual, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses.

In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

In some embodiments, an expression vector (e.g., a lentiviral vector) may be used to introduce the CAR into an immune cell or precursor thereof (e.g., a T cell). Accordingly, an expression vector (e.g., a lentiviral vector) of the present invention may comprise a nucleic acid encoding for a CAR. In some embodiments, the expression vector (e.g., lentiviral vector) will comprise additional elements that will aid in the functional expression of the CAR encoded therein. In some embodiments, an expression vector comprising a nucleic acid encoding for a CAR further comprises a mammalian promoter. In one embodiment, the vector further comprises an elongation-factor-1-alpha promoter (EF-1$\alpha$ promoter). Use of an EF-1$\alpha$ promoter may increase the efficiency in expression of downstream transgenes (e.g., a CAR encoding nucleic acid sequence). Physiologic promoters (e.g., an EF-1a promoter) may be less likely to induce integration mediated genotoxicity, and may abrogate the ability of the retroviral vector to transform stem cells. Other physiological promoters suitable for use in a vector (e.g., lentiviral vector) are known to those of skill in the art and may be incorporated into a vector of the present invention. In some embodiments, the vector (e.g., lentiviral vector) further comprises a non-requisite cis acting sequence that may improve titers and gene expression. One non-limiting example of a non-requisite cis acting sequence is the central polypurine tract and central termination sequence (cPPT/CTS) which is important for efficient reverse transcription and nuclear import. Other non-requisite cis acting sequences are known to those of skill in the art and may be incorporated into a vector (e.g., lentiviral vector) of the present invention. In some embodiments, the vector further comprises a posttranscriptional regulatory element. Posttranscriptional regulatory elements may improve RNA translation, improve transgene expression and stabilize RNA transcripts. One example of a posttranscriptional regulatory element is the woodchuck hepatitis virus posttranscriptional regulatory element (WPRE). Accordingly, in some embodiments a vector for the present invention further comprises a WPRE sequence. Various posttranscriptional regulator elements are known to those of skill in the art and may be incorporated into a vector (e.g., lentiviral vector) of the present invention. A vector of the present invention may further comprise additional elements such as a rev response element (RRE) for RNA transport, packaging sequences, and 5' and 3' long terminal repeats (LTRs). The term "long terminal repeat" or "LTR" refers to domains of base pairs located at the ends of retroviral DNAs which comprise U3, R and U5 regions. LTRs generally provide functions required for the expression of retroviral genes (e.g., promotion, initiation and polyadenylation of gene transcripts) and to viral replication. In one embodiment, a vector (e.g., lentiviral vector) of the present invention includes a 3' U3 deleted LTR. Accordingly, a vector (e.g., lentiviral vector) of the present invention may comprise any combination of the elements described herein to enhance the efficiency of functional expression of transgenes. For example, a vector (e.g., lentiviral vector) of the present invention may comprise a WPRE sequence, cPPT sequence, RRE sequence, 5'LTR, 3' U3 deleted LTR' in addition to a nucleic acid encoding for a CAR.

Vectors of the present invention may be self-inactivating vectors. As used herein, the term "self-inactivating vector" refers to vectors in which the 3' LTR enhancer promoter region (U3 region) has been modified (e.g., by deletion or substitution). A self-inactivating vector may prevent viral transcription beyond the first round of viral replication. Consequently, a self-inactivating vector may be capable of infecting and then integrating into a host genome (e.g., a mammalian genome) only once, and cannot be passed further. Accordingly, self-inactivating vectors may greatly reduce the risk of creating a replication-competent virus.

In some embodiments, a nucleic acid of the present invention may be RNA, e.g., in vitro synthesized RNA. Methods for in vitro synthesis of RNA are known to those of skill in the art; any known method can be used to synthesize RNA comprising a sequence encoding a CAR of the present disclosure. Methods for introducing RNA into a host cell are known in the art. See, e.g., Zhao et al. Cancer Res. (2010) 15: 9053. Introducing RNA comprising a nucleotide sequence encoding a CAR of the present disclosure into a host cell can be carried out in vitro, ex vivo or in vivo. For example, a host cell (e.g., an NK cell, a cytotoxic T lymphocyte, etc.) can be electroporated in vitro or ex vivo with RNA comprising a nucleotide sequence encoding a CAR of the present disclosure.

In order to assess the expression of a polypeptide or portions thereof, the expression vector to be introduced into a cell may also contain either a selectable marker gene or a reporter gene, or both, to facilitate identification and selection of expressing cells from the population of cells sought to be transfected or infected through viral vectors. In some embodiments, the selectable marker may be carried on a separate piece of DNA and used in a co-transfection procedure. Both selectable markers and reporter genes may be flanked with appropriate regulatory sequences to enable expression in the host cells. Useful selectable markers include, without limitation, antibiotic-resistance genes.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assessed at a suitable time after the DNA has been introduced into the recipient cells. Suitable reporter genes may include, without limitation, genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82).

In some embodiments, a nucleic acid of the present disclosure is provided for the production of a CAR as described herein, e.g., in a mammalian cell. In some embodiments, a nucleic acid of the present disclosure provides for amplification of the CAR-encoding nucleic acid.

D. Modified Immune Cells

The present invention provides modified immune cells or precursors thereof (e.g., a T cell) comprising a CAR as described herein. Also provided are modified immune cells or precursor cell thereof comprising a nucleic acid encoding a CAR. Accordingly, such modified cells possess the specificity directed by the CAR that is expressed therein. For example, a modified cell of the present disclosure comprising a fibronectic CAR possesses specificity for fibronectin on a target cell (e.g., a cancer cell).

In one aspect, the invention includes a modified immune cell or precursor cell thereof, comprising a CAR comprising an antigen binding domain capable of binding the IIICS domain of fibronectin, a transmembrane domain, and an intracellular domain. In another aspect, the invention includes a modified immune cell or precursor cell thereof, comprising a CAR comprising an antigen binding domain capable of binding the EDA domain of fibronectin, a transmembrane domain, and an intracellular domain. In another aspect, the invention includes a modified immune cell or precursor cell thereof, comprising a CAR comprising an antigen binding domain capable of binding the EDB domain of fibronectin, a transmembrane domain, and an intracellular domain.

In certain embodiments, the modified cell is a modified immune cell. In certain embodiments, the modified cell is an autologous cell. In certain embodiments, the modified cell is an autologous cell obtained from a human subject. In certain embodiments, the modified cell is a T cell.

E. Methods of Treatment

The modified cells (e.g., T cells) described herein may be included in a composition for immunotherapy. The composition may include a pharmaceutical composition and further include a pharmaceutically acceptable carrier. A therapeutically effective amount of the pharmaceutical composition comprising the modified T cells may be administered.

In one aspect, the invention includes a method for adoptive cell transfer therapy comprising administering to a subject in need thereof a modified T cell of the present invention. In another aspect, the invention includes a method of treating a disease or condition in a subject comprising administering to a subject in need thereof a population of modified T cells.

Methods for administration of immune cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338. In some embodiments, the cell therapy, e.g., adoptive T cell therapy is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

In some embodiments, the subject has been treated with a therapeutic agent targeting the disease or condition, e.g.

the tumor, prior to administration of the cells or composition containing the cells. In some aspects, the subject is refractory or non-responsive to the other therapeutic agent. In some embodiments, the subject has persistent or relapsed disease, e.g., following treatment with another therapeutic intervention, including chemotherapy, radiation, and/or hematopoietic stem cell transplantation (HSCT), e.g., allogenic HSCT. In some embodiments, the administration effectively treats the subject despite the subject having become resistant to another therapy.

In some embodiments, the subject is responsive to the other therapeutic agent, and treatment with the therapeutic agent reduces disease burden. In some aspects, the subject is initially responsive to the therapeutic agent, but exhibits a relapse of the disease or condition over time. In some embodiments, the subject has not relapsed. In some such embodiments, the subject is determined to be at risk for relapse, such as at a high risk of relapse, and thus the cells are administered prophylactically, e.g., to reduce the likelihood of or prevent relapse. In some aspects, the subject has not received prior treatment with another therapeutic agent.

In some embodiments, the subject has persistent or relapsed disease, e.g., following treatment with another therapeutic intervention, including chemotherapy, radiation, and/or hematopoietic stem cell transplantation (HSCT), e.g., allogenic HSCT. In some embodiments, the administration effectively treats the subject despite the subject having become resistant to another therapy.

The modified immune cells of the present invention can be administered to an animal, preferably a mammal, even more preferably a human, to treat a cancer. In addition, the cells of the present invention can be used for the treatment of any condition related to a cancer, especially a cell-mediated immune response against a tumor cell(s), where it is desirable to treat or alleviate the disease. The types of cancers to be treated with the modified cells or pharmaceutical compositions of the invention include, carcinoma, blastoma, and sarcoma, and certain leukemia or lymphoid malignancies, benign and malignant tumors, and malignancies e.g., sarcomas, carcinomas, and melanomas. Other exemplary cancers include but are not limited breast cancer, prostate cancer, ovarian cancer, cervical cancer, skin cancer, pancreatic cancer, colorectal cancer, renal cancer, liver cancer, brain cancer, lymphoma, leukemia, lung cancer, thyroid cancer, and the like. The cancers may be non-solid tumors (such as hematological tumors) or solid tumors. Adult tumors/cancers and pediatric tumors/cancers are also included. In one embodiment, the cancer is a solid tumor or a hematological tumor. In one embodiment, the cancer is a carcinoma. In one embodiment, the cancer is a sarcoma. In one embodiment, the cancer is a leukemia. In one embodiment the cancer is a solid tumor.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

Carcinomas that can be amenable to therapy by a method disclosed herein include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelial carcinoma, and nasopharyngeal carcinoma.

Sarcomas that can be amenable to therapy by a method disclosed herein include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

In certain exemplary embodiments, the modified immune cells of the invention are used to treat a myeloma, or a condition related to myeloma. Examples of myeloma or conditions related thereto include, without limitation, light chain myeloma, non-secretory myeloma, monoclonal gamopathy of undetermined significance (MGUS), plasmacytoma (e.g., solitary, multiple solitary, extramedullary plasmacytoma), amyloidosis, and multiple myeloma. In one embodiment, a method of the present disclosure is used to treat multiple myeloma. In one embodiment, a method of the present disclosure is used to treat refractory myeloma. In one embodiment, a method of the present disclosure is used to treat relapsed myeloma.

In certain exemplary embodiments, the modified immune cells of the invention are used to treat a melanoma, or a condition related to melanoma. Examples of melanoma or conditions related thereto include, without limitation, superficial spreading melanoma, nodular melanoma, lentigo maligna melanoma, acral lentiginous melanoma, amelanotic melanoma, or melanoma of the skin (e.g., cutaneous, eye, vulva, vagina, rectum melanoma). In one embodiment, a method of the present disclosure is used to treat cutaneous melanoma. In one embodiment, a method of the present disclosure is used to treat refractory melanoma. In one embodiment, a method of the present disclosure is used to treat relapsed melanoma.

In yet other exemplary embodiments, the modified immune cells of the invention are used to treat a sarcoma, or a condition related to sarcoma. Examples of sarcoma or conditions related thereto include, without limitation, angiosarcoma, chondrosarcoma, Ewing's sarcoma, fibrosarcoma, gastrointestinal stromal tumor, leiomyosarcoma, liposarcoma, malignant peripheral nerve sheath tumor, osteosarcoma, pleomorphic sarcoma, rhabdomyosarcoma, and synovial sarcoma. In one embodiment, a method of the present disclosure is used to treat synovial sarcoma. In one embodiment, a method of the present disclosure is used to treat liposarcoma such as myxoid/round cell liposarcoma, differentiated/dedifferentiated liposarcoma, and pleomorphic liposarcoma. In one embodiment, a method of the present disclosure is used to treat myxoid/round cell liposarcoma. In one embodiment, a method of the present disclosure is used to treat a refractory sarcoma. In one embodiment, a method of the present disclosure is used to treat a relapsed sarcoma.

The cells of the invention to be administered may be autologous, with respect to the subject undergoing therapy.

The administration of the cells of the invention may be carried out in any convenient manner known to those of skill in the art. The cells of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the cells of the invention are injected directly into a site of inflammation in the subject, a local disease site in the subject, a lymph node, an organ, a tumor, and the like.

In some embodiments, the cells are administered at a desired dosage, which in some aspects includes a desired dose or number of cells or cell type(s) and/or a desired ratio of cell types. Thus, the dosage of cells in some embodiments is based on a total number of cells (or number per kg body weight) and a desired ratio of the individual populations or sub-types, such as the CD4+ to CD8+ ratio. In some embodiments, the dosage of cells is based on a desired total number (or number per kg of body weight) of cells in the individual populations or of individual cell types. In some embodiments, the dosage is based on a combination of such features, such as a desired number of total cells, desired ratio, and desired total number of cells in the individual populations.

In some embodiments, the populations or sub-types of cells, such as $CD8^+$ and $CD4^+$ T cells, are administered at or within a tolerated difference of a desired dose of total cells, such as a desired dose of T cells. In some aspects, the desired dose is a desired number of cells or a desired number of cells per unit of body weight of the subject to whom the cells are administered, e.g., cells/kg. In some aspects, the desired dose is at or above a minimum number of cells or minimum number of cells per unit of body weight. In some aspects, among the total cells, administered at the desired dose, the individual populations or sub-types are present at or near a desired output ratio (such as $CD4^+$ to $CD8^+$ ratio), e.g., within a certain tolerated difference or error of such a ratio.

In some embodiments, the cells are administered at or within a tolerated difference of a desired dose of one or more of the individual populations or sub-types of cells, such as a desired dose of CD4+ cells and/or a desired dose of CD8+ cells. In some aspects, the desired dose is a desired number of cells of the sub-type or population, or a desired number of such cells per unit of body weight of the subject to whom the cells are administered, e.g., cells/kg. In some aspects, the desired dose is at or above a minimum number of cells of the population or subtype, or minimum number of cells of the population or sub-type per unit of body weight. Thus, in some embodiments, the dosage is based on a desired fixed dose of total cells and a desired ratio, and/or based on a desired fixed dose of one or more, e.g., each, of the individual sub-types or sub-populations. Thus, in some embodiments, the dosage is based on a desired fixed or minimum dose of T cells and a desired ratio of $CD4^+$ to $CD8^+$ cells, and/or is based on a desired fixed or minimum dose of $CD4^+$ and/or $CD8^+$ cells.

In certain embodiments, the cells, or individual populations of sub-types of cells, are administered to the subject at a range of about one million to about 100 billion cells, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges.

In some embodiments, the dose of total cells and/or dose of individual sub-populations of cells is within a range of between at or about $1\times10^5$ cells/kg to about $1\times10^{11}$ cells/kg $10^4$ and at or about $10^{11}$ cells/kilograms (kg) body weight, such as between $10^5$ and $10^6$ cells/kg body weight, for example, at or about $1\times10^5$ cells/kg, $1.5\times10^5$ cells/kg, $2\times10^5$ cells/kg, or $1\times10^6$ cells/kg body weight. For example, in some embodiments, the cells are administered at, or within a certain range of error of, between at or about $10^4$ and at or about $10^9$ T cells/kilograms (kg) body weight, such as between $10^5$ and $10^6$ T cells/kg body weight, for example, at or about $1\times10^5$ T cells/kg, $1.5\times10^5$ T cells/kg, $2\times10^5$ T cells/kg, or $1\times10^6$ T cells/kg body weight. In other exemplary embodiments, a suitable dosage range of modified cells for use in a method of the present disclosure includes, without limitation, from about $1\times10^5$ cells/kg to about $1\times10^6$ cells/kg, from about $1\times10^6$ cells/kg to about $1\times10^9$ cells/kg, from about $1\times10^9$ cells/kg about $1\times10^8$ cells/kg, from about $1\times10^8$ cells/kg about $1\times10^9$ cells/kg, from about $1\times10^9$ cells/kg about $1\times10^{10}$ cells/kg, from about $1\times10^{10}$ cells/kg about $1\times10^{11}$ cells/kg. In an exemplary embodiment, a suitable dosage for use in a method of the present disclosure is about $1\times10^8$ cells/kg. In an exemplary embodiment, a suitable dosage for use in a method of the present disclosure is about $1\times10^7$ cells/kg. In other embodiments, a suitable dosage is from about $1\times10^7$ total cells to about $5\times10^7$ total cells. In some embodiments, a suitable dosage is from about $1\times10^8$ total cells to about $5\times10^8$ total cells. In some embodiments, a suitable dosage is from about $1.4\times10^7$ total cells to about $1.1\times10^9$ total cells. In an exemplary embodiment, a suitable dosage for use in a method of the present disclosure is about $7\times10^9$ total cells.

In some embodiments, the cells are administered at or within a certain range of error of between at or about $10^4$ and at or about $10^9$ $CD4^+$ and/or $CD8^+$ cells/kilograms (kg) body weight, such as between $10^5$ and $10^6$ $CD4^+$ and/or $CD8^+$ cells/kg body weight, for example, at or about $1\times10^5$ $CD4^+$ and/or $CD8^+$ cells/kg, $1.5\times10^5$ $CD4^+$ and/or $CD8^+$ cells/kg, $2\times10^5$ $CD4^+$ and/or $CD8^+$ cells/kg, or $1\times10^6$ $CD4^+$ and/or $CD8^+$ cells/kg body weight. In some embodiments, the cells are administered at or within a certain range of error of, greater than, and/or at least about $1\times10^6$, about $2.5\times10^6$, about $5\times10^6$, about $7.5\times10^6$, or about $9\times10^6$ $CD4^+$ cells, and/or at least about $1\times10^6$, about $2.5\times10^6$, about $5\times10^6$, about $7.5\times10^6$, or about $9\times10^6$ CD8+ cells, and/or at least about $1\times10^6$, about $2.5\times10^6$, about $5\times10^6$, about $7.5\times10^6$, or about $9\times10^6$ T cells. In some embodiments, the cells are administered at or within a certain range of error of between about $10^8$ and $10^{12}$ or between about $10^{10}$ and $10^{11}$ T cells, between about $10^8$ and $10^{12}$ or between about $10^{10}$ and $10^{11}$ $CD4^+$ cells, and/or between about $10^8$ and $10^{12}$ or between about $10^{10}$ and $10^{11}$ $CD8^+$ cells.

In some embodiments, the cells are administered at or within a tolerated range of a desired output ratio of multiple cell populations or sub-types, such as CD4+ and CD8+ cells or sub-types. In some aspects, the desired ratio can be a specific ratio or can be a range of ratios, for example, in some embodiments, the desired ratio (e.g., ratio of $CD4^+$ to $CD8^+$ cells) is between at or about 5:1 and at or about 5:1 (or greater than about 1:5 and less than about 5:1), or between at or about 1:3 and at or about 3:1 (or greater than about 1:3 and less than about 3:1), such as between at or about 2:1 and at or about 1:5 (or greater than about 1:5 and less than about 2:1, such as at or about 5:1, 4.5:1, 4:1, 3.5:1, 3:1, 2.5:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9: 1:2, 1:2.5, 1:3, 1:3.5, 1:4, 1:4.5, or 1:5. In some aspects, the tolerated difference is within about 1%, about 2%, about 3%, about 4% about 5%, about 10%, about 15%, about 20%, about 25%, about 30%, about 35%, about 40%, about 45%, about 50% of the desired ratio, including any value in between these ranges.

In some embodiments, a dose of modified cells is administered to a subject in need thereof, in a single dose or multiple doses. In some embodiments, a dose of modified cells is administered in multiple doses, e.g., once a week or every 7 days, once every 2 weeks or every 14 days, once every 3 weeks or every 21 days, once every 4 weeks or every 28 days. In an exemplary embodiment, a single dose of modified cells is administered to a subject in need thereof. In an exemplary embodiment, a single dose of modified cells is administered to a subject in need thereof by rapid intravenous infusion.

For the prevention or treatment of disease, the appropriate dosage may depend on the type of disease to be treated, the type of cells or recombinant receptors, the severity and course of the disease, whether the cells are administered for preventive or therapeutic purposes, previous therapy, the subject's clinical history and response to the cells, and the discretion of the attending physician. The compositions and cells are in some embodiments suitably administered to the subject at one time or over a series of treatments.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agents includes a cytokine, such as IL-2, for example, to enhance persistence. In some embodiments, the methods comprise administration of a chemotherapeutic agent.

In certain embodiments, the modified cells of the invention (e.g., a modified cell comprising a CAR) may be administered to a subject in combination with an immune checkpoint antibody (e.g., an anti-PD1, anti-CTLA-4, or anti-PDL1 antibody). For example, the modified cell may be administered in combination with an antibody or antibody fragment targeting, for example, PD-1 (programmed death 1 protein). Examples of anti-PD-1 antibodies include, but are not limited to, pembrolizumab (KEYTRUDA®, formerly lambrolizumab, also known as MK-3475), and nivolumab (BMS-936558, MDX-1106, ONO-4538, OPDIVA®) or an antigen-binding fragment thereof. In certain embodiments, the modified cell may be administered in combination with an anti-PD-L1 antibody or antigen-binding fragment thereof. Examples of anti-PD-L1 antibodies include, but are not limited to, BMS-936559, MPDL3280A (TECENTRIQ®, Atezolizumab), and MEDI4736 (Durvalumab, Imfinzi). In certain embodiments, the modified cell may be administered in combination with an anti-CTLA-4 antibody or antigen-binding fragment thereof. An example of an anti-CTLA-4 antibody includes, but is not limited to, Ipilimumab (trade name Yervoy). Other types of immune checkpoint modulators may also be used including, but not limited to, small molecules, siRNA, miRNA, and CRISPR systems. Immune checkpoint modulators may be administered before, after, or concurrently with the modified cell comprising the CAR. In certain embodiments, combination treatment comprising an immune checkpoint modulator may increase the therapeutic efficacy of a therapy comprising a modified cell of the present invention.

Following administration of the cells, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells is measured by assaying expression and/or secretion of one or more cytokines, such as CD 107a, IFNγ, IL-2, and TNF. In some aspects the biological activity is measured by assessing clinical outcome, such as reduction in tumor burden or load.

In certain embodiments, the subject is provided a secondary treatment. Secondary treatments include but are not limited to chemotherapy, radiation, surgery, and medications.

In some embodiments, the subject can be administered a conditioning therapy prior to CAR T cell therapy. In some embodiments, the conditioning therapy comprises administering an effective amount of cyclophosphamide to the subject. In some embodiments, the conditioning therapy comprises administering an effective amount of fludarabine to the subject. In preferred embodiments, the conditioning therapy comprises administering an effective amount of a combination of cyclophosphamide and fludarabine to the subject. Administration of a conditioning therapy prior to CAR T cell therapy may increase the efficacy of the CAR T cell therapy. Methods of conditioning patients for T cell therapy are described in U.S. Pat. No. 9,855,298, which is incorporated herein by reference in its entirety.

In some embodiments, a specific dosage regimen of the present disclosure includes a lymphodepletion step prior to the administration of the modified T cells. In an exemplary embodiment, the lymphodepletion step includes administration of cyclophosphamide and/or fludarabine.

In some embodiments, the lymphodepletion step includes administration of cyclophosphamide at a dose of between about 200 mg/m$^2$/day and about 2000 mg/m$^2$/day (e.g., 200 mg/m$^2$/day, 300 mg/m$^2$/day, or 500 mg/m$^2$/day). In an exemplary embodiment, the dose of cyclophosphamide is about 300 mg/m$^2$/day. In some embodiments, the lymphodepletion step includes administration of fludarabine at a dose of between about 20 mg/m$^2$/day and about 900 mg/m$^2$/day (e.g., 20 mg/m$^2$/day, 25 mg/m$^2$/day, 30 mg/m$^2$/day, or 60 mg/m$^2$/day). In an exemplary embodiment, the dose of fludarabine is about 30 mg/m$^2$/day.

In some embodiment, the lymphodepletion step includes administration of cyclophosphamide at a dose of between about 200 mg/m$^2$/day and about 2000 mg/m$^2$/day (e.g., 200 mg/m$^2$/day, 300 mg/m$^2$/day, or 500 mg/m$^2$/day), and fludarabine at a dose of between about 20 mg/m$^2$/day and about 900 mg/m$^2$/day (e.g., 20 mg/m$^2$/day, 25 mg/m$^2$/day, 30 mg/m$^2$/day, or 60 mg/m$^2$/day). In an exemplary embodiment, the lymphodepletion step includes administration of cyclophosphamide at a dose of about 300 mg/m$^2$/day, and fludarabine at a dose of about 30 mg/m$^2$/day.

In an exemplary embodiment, the dosing of cyclophosphamide is 300 mg/m$^2$/day over three days, and the dosing of fludarabine is 30 mg/m$^2$/day over three days.

Dosing of lymphodepletion chemotherapy may be scheduled on Days −6 to −4 (with a −1 day window, i.e., dosing on Days −7 to −5) relative to T cell (e.g., CAR-T, TCR-T, a modified T cell, etc.) infusion on Day 0.

In an exemplary embodiment, for a subject having cancer, the subject receives lymphodepleting chemotherapy including 300 mg/m$^2$ of cyclophosphamide by intravenous infusion 3 days prior to administration of the modified T cells. In an exemplary embodiment, for a subject having cancer, the subject receives lymphodepleting chemotherapy including 300 mg/m$^2$ of cyclophosphamide by intravenous infusion for 3 days prior to administration of the modified T cells.

In an exemplary embodiment, for a subject having cancer, the subject receives lymphodepleting chemotherapy including fludarabine at a dose of between about 20 mg/m$^2$/day and about 900 mg/m$^2$/day (e.g., 20 mg/m$^2$/day, 25 mg/m$^2$/day, 30 mg/m$^2$/day, or 60 mg/m$^2$/day). In an exemplary embodiment, for a subject having cancer, the subject receives lymphodepleting chemotherapy including fludarabine at a dose of 30 mg/m$^2$ for 3 days.

In an exemplary embodiment, for a subject having cancer, the subject receives lymphodepleting chemotherapy including cyclophosphamide at a dose of between about 200 mg/m$^2$/day and about 2000 mg/m$^2$/day (e.g., 200 mg/m$^2$/day, 300 mg/m$^2$/day, or 500 mg/m$^2$/day), and fludarabine at a dose of between about 20 mg/m$^2$/day and about 900 mg/m$^2$/day (e.g., 20 mg/m$^2$/day, 25 mg/m$^2$/day, 30 mg/m$^2$/day, or 60 mg/m$^2$/day). In an exemplary embodiment, for a subject having cancer, the subject receives lymphodepleting chemotherapy including cyclophosphamide at a dose of about 300 mg/m$^2$/day, and fludarabine at a dose of 30 mg/m$^2$ for 3 days.

Cells of the invention can be administered in dosages and routes and at times to be determined in appropriate preclinical and clinical experimentation and trials. Cell compositions may be administered multiple times at dosages within these ranges. Administration of the cells of the invention may be combined with other methods useful to treat the desired disease or condition as determined by those of skill in the art.

It is known in the art that one of the adverse effects following infusion of CAR T cells is the onset of immune activation, known as cytokine release syndrome (CRS). CRS is immune activation resulting in elevated inflammatory cytokines. CRS is a known on-target toxicity, development of which likely correlates with efficacy. Clinical and laboratory measures range from mild CRS (constitutional symptoms and/or grade-2 organ toxicity) to severe CRS (sCRS; grade≥3 organ toxicity, aggressive clinical intervention, and/or potentially life threatening). Clinical features include: high fever, malaise, fatigue, myalgia, nausea, anorexia, tachycardia/hypotension, capillary leak, cardiac dysfunction, renal impairment, hepatic failure, and disseminated intravascular coagulation. Dramatic elevations of cytokines including interferon-gamma, granulocyte macrophage colony-stimulating factor, IL-10, and IL-6 have been shown following CAR T-cell infusion. One CRS signature is elevation of cytokines including IL-6 (severe elevation), IFN-gamma, TNF-alpha (moderate), and IL-2 (mild). Elevations in clinically available markers of inflammation including ferritin and C-reactive protein (CRP) have also been observed to correlate with the CRS syndrome. The presence of CRS generally correlates with expansion and progressive immune activation of adoptively transferred cells. It has been demonstrated that the degree of CRS severity is dictated by disease burden at the time of infusion as patients with high tumor burden experience a more sCRS.

Accordingly, the invention provides for, following the diagnosis of CRS, appropriate CRS management strategies to mitigate the physiological symptoms of uncontrolled inflammation without dampening the antitumor efficacy of the engineered cells (e.g., CAR T cells). CRS management strategies are known in the art. For example, systemic corticosteroids may be administered to rapidly reverse symptoms of sCRS (e.g., grade 3 CRS) without compromising initial antitumor response.

In some embodiments, an anti-IL-6R antibody may be administered. An example of an anti-IL-6R antibody is the Food and Drug Administration-approved monoclonal antibody tocilizumab, also known as atlizumab (marketed as Actemra, or RoActemra). Tocilizumab is a humanized monoclonal antibody against the interleukin-6 receptor (IL-6R). Administration of tocilizumab has demonstrated near-immediate reversal of CRS.

CRS is generally managed based on the severity of the observed syndrome and interventions are tailored as such. CRS management decisions may be based upon clinical signs and symptoms and response to interventions, not solely on laboratory values alone.

Mild to moderate cases generally are treated with symptom management with fluid therapy, non-steroidal anti-inflammatory drug (NSAID) and antihistamines as needed for adequate symptom relief. More severe cases include patients with any degree of hemodynamic instability; with any hemodynamic instability, the administration of tocilizumab is recommended. The first-line management of CRS may be tocilizumab, in some embodiments, at the labeled dose of 8 mg/kg IV over 60 minutes (not to exceed 800 mg/dose); tocilizumab can be repeated Q8 hours. If suboptimal response to the first dose of tocilizumab, additional doses of tocilizumab may be considered. Tocilizumab can be administered alone or in combination with corticosteroid therapy. Patients with continued or progressive CRS symptoms, inadequate clinical improvement in 12-18 hours or poor response to tocilizumab, may be treated with high-dose corticosteroid therapy, generally hydrocortisone 100 mg IV or methylprednisolone 1-2 mg/kg. In patients with more severe hemodynamic instability or more severe respiratory symptoms, patients may be administered high-dose corticosteroid therapy early in the course of the CRS. CRS management guidance may be based on published standards (Lee et al. (2019) *Biol Blood Marrow Transplant*, doi.org/10.1016/j.bbmt.2018.12.758; Neelapu et al. (2018) *Nat Rev Clin Oncology,* 15:47; Teachey et al. (2016) *Cancer Discov,* 6(6):664-679).

Features consistent with Macrophage Activation Syndrome (MAS) or Hemophagocytic lymphohistiocytosis (HLH) have been observed in patients treated with CAR-T therapy (Henter, 2007), coincident with clinical manifestations of the CRS. MAS appears to be a reaction to immune activation that occurs from the CRS, and should therefore be considered a manifestation of CRS. MAS is similar to HLH (also a reaction to immune stimulation). The clinical syndrome of MAS is characterized by high grade non-remitting fever, cytopenias affecting at least two of three lineages, and hepatosplenomegaly. It is associated with high serum ferritin, soluble interleukin-2 receptor, and triglycerides, and a decrease of circulating natural killer (NK) activity.

In one aspect, the invention includes a method of treating cancer in a subject in need thereof, comprising administering to the subject any one of the modified immune or precursor cells disclosed herein. Yet another aspect of the invention includes a method of treating cancer in a subject in need thereof, comprising administering to the subject a modified immune or precursor cell generated by any one of the methods disclosed herein.

F. Sources of Immune Cells

In certain embodiments, a source of immune cells (e.g. T cells) is obtained from a subject for ex vivo manipulation. Sources of target cells for ex vivo manipulation may also include, e.g., autologous or heterologous donor blood, cord blood, or bone marrow. For example the source of immune cells may be from the subject to be treated with the modified immune cells of the invention, e.g., the subject's blood, the subject's cord blood, or the subject's bone marrow. Non-limiting examples of subjects include humans, dogs, cats, mice, rats, and transgenic species thereof. Preferably, the subject is a human.

Immune cells can be obtained from a number of sources, including blood, peripheral blood mononuclear cells, bone marrow, lymph node tissue, spleen tissue, umbilical cord, lymph, or lymphoid organs. Immune cells are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). In some aspects, the cells are human cells. With reference to the subject to be treated, the cells may be allogeneic and/or autologous. The cells typically are primary cells, such as those isolated directly from a subject and/or isolated from a subject and frozen.

In certain embodiments, the immune cell is a T cell, e.g., a CD8+ T cell (e.g., a CD8+ naive T cell, central memory T cell, or effector memory T cell), a CD4+ T cell, a natural killer T cell (NKT cells), a regulatory T cell (Treg), a stem cell memory T cell, a lymphoid progenitor cell a hematopoietic stem cell, a natural killer cell (NK cell) or a dendritic cell. In some embodiments, the cells are monocytes or granulocytes, e.g., myeloid cells, macrophages, neutrophils, dendritic cells, mast cells, eosinophils, and/or basophils. In an embodiment, the target cell is an induced pluripotent stem (iPS) cell or a cell derived from an iPS cell, e.g., an iPS cell generated from a subject, manipulated to alter (e.g., induce a mutation in) or manipulate the expression of one or more target genes, and differentiated into, e.g., a T cell, e.g., a CD8+ T cell (e.g., a CD8+ naive T cell, central memory T cell, or effector memory T cell), a CD4+ T cell, a stem cell memory T cell, a lymphoid progenitor cell or a hematopoietic stem cell.

In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. Among the sub-types and subpopulations of T cells and/or of CD4+ and/or of CD8+ T cells are naive T (TN) cells, effector T cells (TEFF), memory T cells and sub-types thereof, such as stem cell memory T (TSCM), central memory T (TCM), effector memory T (TEM), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells. In certain embodiments, any number of T cell lines available in the art, may be used.

In some embodiments, the methods include isolating immune cells from the subject, preparing, processing, culturing, and/or engineering them. In some embodiments, preparation of the engineered cells includes one or more culture and/or preparation steps. The cells for engineering as described may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered. Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, and pig. In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets. In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some aspects, a washing step is accomplished by tangential flow filtration (TFF) according to the manufacturer's instructions. In some embodiments, the cells are resuspended in a variety of biocompatible buffers after washing. In certain embodiments, components of a blood cell sample are removed and the cells directly resuspended in culture media. In some embodiments, the methods include density-based cell separation methods, such as the preparation of white blood cells from peripheral blood by lysing the red blood cells and centrifugation through a Percoll or Ficoll gradient.

In one embodiment, immune are obtained cells from the circulating blood of an individual are obtained by apheresis or leukapheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media, such as phosphate buffered saline (PBS) or wash solution lacks calcium and may lack magnesium or may lack many if not all divalent cations, for subsequent processing steps. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population. The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

In some embodiments, one or more of the T cell populations is enriched for or depleted of cells that are positive for (marker+) or express high levels (marker$^{high}$) of one or more particular markers, such as surface markers, or that are negative for (marker −) or express relatively low levels (marker$^{low}$) of one or more markers. For example, in some aspects, specific subpopulations of T cells, such as cells positive or expressing high levels of one or more surface markers, e.g., CD28+, CD62L+, CCR7+, CD27+, CD127+, CD4+, CD8+, CD45RA+, and/or CD45RO+ T cells, are isolated by positive or negative selection techniques. In some cases, such markers are those that are absent or expressed at relatively low levels on certain populations of T cells (such as non-memory cells) but are present or expressed at relatively higher levels on certain other populations of T cells (such as memory cells). In one embodiment, the cells (such as the CD8+ cells or the T cells, e.g., CD3+ cells) are enriched for (i.e., positively selected for) cells that are positive or expressing high surface levels of CD45RO, CCR7, CD28, CD27, CD44, CD 127, and/or CD62L and/or depleted of (e.g., negatively selected for) cells that are positive for or express high surface levels of CD45RA. In some embodiments, cells are enriched for or depleted of cells positive or expressing high surface levels of CD 122, CD95, CD25, CD27, and/or IL7-Ra (CD 127). In some examples, CD8+ T cells are enriched for cells positive for CD45RO (or negative for CD45RA) and for CD62L. For example, CD3+, CD28+ T cells can be positively selected using CD3/CD28 conjugated magnetic beads (e.g., DYNABEADS® M-450 CD3/CD28 T Cell Expander).

In some embodiments, T cells are separated from a PBMC sample by negative selection of markers expressed on non-T cells, such as B cells, monocytes, or other white blood cells, such as CD14. In some aspects, a CD4+ or CD8+ selection step is used to separate CD4+ helper and CD8+ cytotoxic T cells. Such CD4+ and CD8+ populations can be further sorted into sub-populations by positive or negative selection for markers expressed or expressed to a relatively higher degree on one or more naive, memory, and/or effector T cell subpopulations. In some embodiments, CD8+ cells are further enriched for or depleted of naive, central memory, effector memory, and/or central memory stem cells, such as by positive or negative selection based on surface antigens associated with the respective subpopulation. In some embodiments, enrichment for central memory T (TCM) cells is carried out to increase efficacy, such as to improve long-term survival, expansion, and/or engraftment following administration, which in some aspects is particularly robust in such sub-populations. In some embodiments, combining TCM-enriched CD8+ T cells and CD4+ T cells further enhances efficacy.

In some embodiments, memory T cells are present in both CD62L+ and CD62L− subsets of CD8+ peripheral blood lymphocytes. PBMC can be enriched for or depleted of CD62L-CD8+ and/or CD62L+CD8+ fractions, such as using anti-CD8 and anti-CD62L antibodies. In some embodiments, a CD4+ T cell population and a CD8+ T cell sub-population, e.g., a sub-population enriched for central memory (TCM) cells. In some embodiments, the enrichment for central memory T (TCM) cells is based on positive or high surface expression of CD45RO, CD62L, CCR7, CD28, CD3, and/or CD 127; in some aspects, it is based on negative selection for cells expressing or highly expressing CD45RA and/or granzyme B. In some aspects, isolation of a CD8+ population enriched for TCM cells is carried out by depletion of cells expressing CD4, CD 14, CD45RA, and positive selection or enrichment for cells expressing CD62L. In one aspect, enrichment for central memory T (TCM) cells is carried out starting with a negative fraction of cells selected based on CD4 expression, which is subjected to a negative selection based on expression of CD 14 and CD45RA, and a positive selection based on CD62L. Such selections in some aspects are carried out simultaneously and in other aspects are carried out sequentially, in either order. In some aspects, the same CD4 expression-based selection step used in preparing the CD8+ cell population or subpopulation, also is used to generate the CD4+ cell population or sub-population, such that both the positive and negative fractions from the CD4-based separation are retained and used in subsequent steps of the methods, optionally following one or more further positive or negative selection steps.

CD4+T helper cells are sorted into naive, central memory, and effector cells by identifying cell populations that have cell surface antigens. CD4+ lymphocytes can be obtained by standard methods. In some embodiments, naive CD4+T lymphocytes are CD45RO−, CD45RA+, CD62L+, CD4+ T cells. In some embodiments, central memory CD4+ cells are CD62L+ and CD45RO+. In some embodiments, effector CD4+ cells are CD62L- and CD45RO. In one example, to enrich for CD4+ cells by negative selection, a monoclonal antibody cocktail typically includes antibodies to CD14, CD20, CD1 lb, CD16, HLA-DR, and CD8. In some embodiments, the antibody or binding partner is bound to a solid support or matrix, such as a magnetic bead or paramagnetic bead, to allow for separation of cells for positive and/or negative selection.

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor. The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells. In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR component and/or costimulatory receptor, e.g., anti-CD3, anti-CD28, for example, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2 and/or IL-15, for example, an IL-2 concentration of at least about 10 units/mL.

In another embodiment, T cells are isolated from peripheral blood by lysing the red blood cells and depleting the monocytes, for example, by centrifugation through a PERCOLL™ gradient. Alternatively, T cells can be isolated from an umbilical cord. In any event, a specific subpopulation of T cells can be further isolated by positive or negative selection techniques.

The cord blood mononuclear cells so isolated can be depleted of cells expressing certain antigens, including, but not limited to, CD34, CD8, CD14, CD19, and CD56. Depletion of these cells can be accomplished using an isolated antibody, a biological sample comprising an antibody, such as ascites, an antibody bound to a physical support, and a cell bound antibody.

Enrichment of a T cell population by negative selection can be accomplished using a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. n yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion.

T cells can also be frozen after the washing step, which does not require the monocyte-removal step. While not wishing to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, in a non-limiting example, one method involves using PBS containing 20% DMSO and 8% human serum albumin, or other suitable cell freezing media. The cells are then frozen to −80° C. at a rate of 1° C. per minute and stored in the vapor phase of a liquid nitrogen storage tank. Other methods of controlled freezing may be used as well as uncontrolled freezing immediately at −20° C. or in liquid nitrogen.

In one embodiment, the population of T cells is comprised within cells such as peripheral blood mononuclear cells, cord blood cells, a purified population of T cells, and a T cell line. In another embodiment, peripheral blood mononuclear cells comprise the population of T cells. In yet another embodiment, purified T cells comprise the population of T cells.

In certain embodiments, T regulatory cells (Tregs) can be isolated from a sample. The sample can include, but is not limited to, umbilical cord blood or peripheral blood. In certain embodiments, the Tregs are isolated by flow-cytometry sorting. The sample can be enriched for Tregs prior to isolation by any means known in the art. The isolated Tregs can be cryopreserved, and/or expanded prior to use. Methods for isolating Tregs are described in U.S. Pat. Nos. 7,754,482, 8,722,400, and 9,555,105, and U.S. patent application Ser. No. 13/639,927, contents of which are incorporated herein in their entirety.

G. Expansion of Immune Cells

Whether prior to or after modification of cells to express a CAR, the cells can be activated and expanded in number using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Publication No. 20060121005. For example, the T cells of the invention may be expanded by contact with a surface having attached thereto an agent that stimulates a CD3/TCR complex associated signal and a ligand that stimulates a co-stimulatory molecule on the surface of the T cells. In particular, T cell populations may be stimulated by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, T cells can be contacted with an anti-CD3 antibody and an anti-CD28 antibody, under conditions appropriate for stimulating proliferation of the T cells. Examples of an anti-CD28 antibody include 9.3, B-T3, XR-CD28 (Diaclone, Besancon, France) and these can be used in the invention, as can other methods and reagents known in the art (see, e.g., ten Berge et al., Transplant Proc. (1998) 30(8): 3975-3977; Haanen et al., J. Exp. Med. (1999) 190(9): 1319-1328; and Garland et al., J. Immunol. Methods (1999) 227(1-2): 53-63).

Expanding T cells by the methods disclosed herein can be multiplied by about 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater, and any and all whole or partial integers therebetween. In one embodiment, the T cells expand in the range of about 20 fold to about 50 fold.

Following culturing, the T cells can be incubated in cell medium in a culture apparatus for a period of time or until the cells reach confluency or high cell density for optimal passage before passing the cells to another culture apparatus. The culturing apparatus can be of any culture apparatus commonly used for culturing cells in vitro. Preferably, the level of confluence is 70% or greater before passing the cells to another culture apparatus. More preferably, the level of confluence is 90% or greater. A period of time can be any time suitable for the culture of cells in vitro. The T cell medium may be replaced during the culture of the T cells at any time. Preferably, the T cell medium is replaced about every 2 to 3 days. The T cells are then harvested from the culture apparatus whereupon the T cells can be used immediately or cryopreserved to be stored for use at a later time. In one embodiment, the invention includes cryopreserving the expanded T cells. The cryopreserved T cells are thawed prior to introducing nucleic acids into the T cell.

In another embodiment, the method comprises isolating T cells and expanding the T cells. In another embodiment, the invention further comprises cryopreserving the T cells prior to expansion. In yet another embodiment, the cryopreserved T cells are thawed for electroporation with the RNA encoding the chimeric membrane protein.

Another procedure for ex vivo expansion cells is described in U.S. Pat. No. 5,199,942 (incorporated herein by reference). Expansion, such as described in U.S. Pat. No. 5,199,942 can be an alternative or in addition to other methods of expansion described herein. Briefly, ex vivo culture and expansion of T cells comprises the addition to the cellular growth factors, such as those described in U.S. Pat. No. 5,199,942, or other factors, such as flt3-L, IL-1, IL-3 and c-kit ligand. In one embodiment, expanding the T cells comprises culturing the T cells with a factor selected from the group consisting of flt3-L, IL-1, IL-3 and c-kit ligand.

The culturing step as described herein (contact with agents as described herein or after electroporation) can be very short, for example less than 24 hours such as 1, 2, 3, 4, 5, 6, 7, 8, 9, 10, 11, 12, 13, 14, 15, 16, 17, 18, 19, 20, 21, 22, or 23 hours. The culturing step as described further herein (contact with agents as described herein) can be longer, for example 1, 2, 3, 4, 5, 6, 7, 8, 9, 10, 11, 12, 13, 14, or more days.

Various terms are used to describe cells in culture. Cell culture refers generally to cells taken from a living organism and grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but is not limited to the seeding density, substrate, medium, and time between passaging.

In one embodiment, the cells may be cultured for several hours (about 3 hours) to about 14 days or any hourly integer value in between. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-gamma, IL-4, IL-7, GM-CSF, IL-10, IL-12, IL-15, TGF-beta, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

The medium used to culture the T cells may include an agent that can co-stimulate the T cells. For example, an agent that can stimulate CD3 is an antibody to CD3, and an agent that can stimulate CD28 is an antibody to CD28. A cell isolated by the methods disclosed herein can be expanded approximately 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater. In one embodiment, the T cells expand in the range of about 20 fold to about 50 fold, or more. In one embodiment, human T regulatory cells are expanded via anti-CD3 antibody coated KT64.86 artificial antigen presenting cells (aAPCs). Methods for expanding and activating T cells can be found in U.S. Pat. Nos. 7,754,482, 8,722,400, and 9,555,105, contents of which are incorporated herein in their entirety.

In one embodiment, the method of expanding the T cells can further comprise isolating the expanded T cells for further applications. In another embodiment, the method of expanding can further comprise a subsequent electroporation of the expanded T cells followed by culturing. The subsequent electroporation may include introducing a nucleic acid encoding an agent, such as a transducing the expanded T cells, transfecting the expanded T cells, or electroporating the expanded T cells with a nucleic acid, into the expanded population of T cells, wherein the agent further stimulates the T cell. The agent may stimulate the T cells, such as by stimulating further expansion, effector function, or another T cell function.

H. Pharmaceutical Compositions and Formulations

Also provided are populations of immune cells of the invention, compositions containing such cells and/or enriched for such cells, such as in which cells expressing CAR make up at least 50%, 60%, 70%, 80%, 90%, 91%, 92%, 93%, 94%, 95%, 96%, 97%, 98%, 99%, or more of the total cells in the composition or cells of a certain type such as T cells or CD8+ or CD4+ cells. Among the compositions are pharmaceutical compositions and formulations for administration, such as for adoptive cell therapy. Also provided are therapeutic methods for administering the cells and compositions to subjects, e.g., patients.

Also provided are compositions including the cells for administration, including pharmaceutical compositions and formulations, such as unit dose form compositions including the number of cells for administration in a given dose or fraction thereof. The pharmaceutical compositions and formulations generally include one or more optional pharmaceutically acceptable carrier or excipient. In some embodiments, the composition includes at least one additional therapeutic agent.

The term "pharmaceutical formulation" refers to a preparation which is in such form as to permit the biological activity of an active ingredient contained therein to be effective, and which contains no additional components which are unacceptably toxic to a subject to which the formulation would be administered. A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative. In some aspects, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol;

resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being treated with the cells, preferably those with activities complementary to the cells, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, and/or vincristine. The pharmaceutical composition in some embodiments contains the cells in amounts effective to treat or prevent the disease or condition, such as a therapeutically effective or prophylactically effective amount. Therapeutic or prophylactic efficacy in some embodiments is monitored by periodic assessment of treated subjects. The desired dosage can be delivered by a single bolus administration of the cells, by multiple bolus administrations of the cells, or by continuous infusion administration of the cells.

Formulations include those for oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, and intraperitoneal administration. In some embodiments, the cells are administered to the subject using peripheral systemic delivery by intravenous, intraperitoneal, or subcutaneous injection. Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyoi (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

While the present invention has been described with reference to the specific embodiments thereof, it should be understood by those skilled in the art that various changes may be made and equivalents may be substituted without departing from the true spirit and scope of the invention. It will be readily apparent to those skilled in the art that other suitable modifications and adaptations of the methods described herein may be made using suitable equivalents without departing from the scope of the embodiments disclosed herein. In addition, many modifications may be made to adapt a particular situation, material, composition of matter, process, process step or steps, to the objective, spirit and scope of the present invention. All such modifications are intended to be within the scope of the claims appended hereto. Having now described certain embodiments in detail, the same will be more clearly understood by reference to the following examples, which are included for purposes of illustration only and are not intended to be limiting.

EXPERIMENTAL EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods

Molecular Cloning: The scFv of FDC6, L19, and C6 were synthesized and cloned into the destination pTRPE lentiviral vector. These vectors are third-generation lentiviral production vectors utilizing the EF1α promoter, and containing the CD8a leader sequence, hinge, transmembrane domain, and 4-1BB and CD3z intracellular signaling domains.

Figure 19:
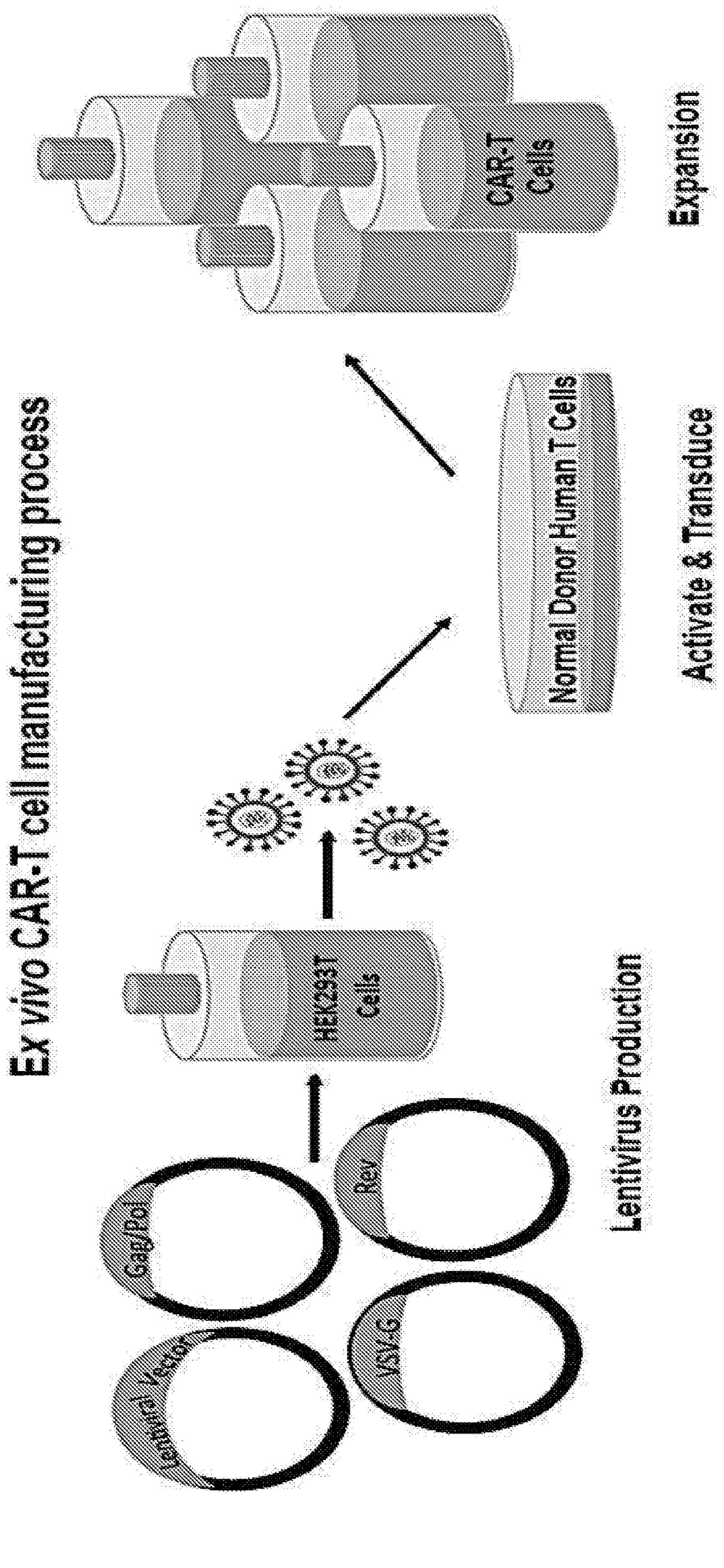
FIG. 19 is a diagram illustrating the manufacturing process used to produce ex vivo CAR-T cells. HEK293T cells are transfected with lentiviral expression vectors in addition to gag/pol, rev, and env packaging mix. Virus is collected and concentrated at 24 and 48 hours. Normal donor T cells are activated with CD3/CD28 magnetic Dynabeads (Thermo Fisher Scientific), transduced with lentivirus 16 hours after bead activation, and cultured/expanded with the addition of IL-2 until optimum resting cell size is reached. Cells are cryopreserved and stored for use in functional assays.

Transduction and Expansion of Normal Donor T Cells: HEK 293T cells were transfected with pTRPE-FDC6-BBz, pTRPE-L19-BBz, pTRPE-5E5-CD2z, pELPS-CD19-BBz, and pTRPE-C6-BBz in addition to gag/pol, env, and Vsvg packaging mix. Virus was collected and concentrated at 24 and 48 hours. Normal donor T cells were obtained from the Human Immunology Core (HIC) at the University of Pennsylvania where they were negatively selected from apheresis. The normal donor T cells were activated in vitro with CD3/CD28 magnetic Dynabeads (Thermo Fischer Scientific), transduced with lentivirus 16 hours after bead activation, and cultured in RPMI 1640 medium (Gibco) supplemented with 10% FBS, 1% penicillin-streptomycin (Gibco), 1% HEPES (Gibco), and 1% GlutaMax (Gibco) (R10 complete growth medium), with the addition of 30 U/mL of IL-2 for 10-17 days (illustrated in FIG. 19).

Cell Culture: The adherent LNCaP, PC3, and DU145 prostate cancer cells lines were obtained from ATCC and maintained with R10 complete growth medium. The human embryonic kidney 293T cell line was also obtained from ATCC and maintained on R10. All T cells used in assays were obtained from the Human Immunology Core at the University of Pennsylvania and activated and transduced in R10, expanded in R10 supplemented with IL-2, and maintained in R10 during use in assays. PC3 cells were lentivirally transduced with pTRPE-CBG-T2A-GFP lentiviral vector for use in animal studies.

Flow Cytometry: Before each staining, cells were washed in either phosphate-buffered saline (PBS), or PBS containing 2% FBS, and stains were performed on ice. CAR positive T cells were detected by staining with biotinylated goat anti mouse F(ab)2 antibody (Jackson ImmunoResearch) and PE-conjugated streptavidin, or Protein L staining followed by PE-conjugated streptavidin where indicated. Flow analysis was performed by gating singlets on FSC-H versus FSC-A and SSC-H versus SSC-A, then on forward versus side scatter characteristics. All flow cytometry was performed on LSRFortessa or LSRII multi-laser Becton Dickinson cytometers.

Cytokine Secretion: FDC6-CAR, L19-CAR, C6-CAR, or 5E5-CD2z CAR-T cells were incubated with PC3 target cells at a 1:1 ratio for 16 hours in R10 medium at 37° C. NTD and CD19-CAR-T cells were used as a control in the same conditions where indicated. After 16 hours, supernatant was collected and analyzed for IFN-γ production using the Human DuoSet ELISA kit (R&D Systems).

Cytotoxicity Assays: Cytotoxicity assays were performed using the xCELLigence real-time cell analysis (RTCA) system, which measures rate of de-adherence as target cells are lysed/undergo cytolytic responses after the addition of cytolytic cells. Adherent PC3, DU145, and LNCaP (where noted) target cells in culture were suspended using trypsin (0.05%) and counted on a Beckman Coulter multisizer Coulter Counter, then 1E4 PC3 target cells were plated on an xCELLigence assay E-plate and allowed to adhere overnight at 37° C. After overnight incubation, T cells, were added at the indicated effector:target ratios, and co-cultures were returned to 37° C., and de-adherence data was monitored and recorded automatically and continuously for 7 days.

Figure 20:
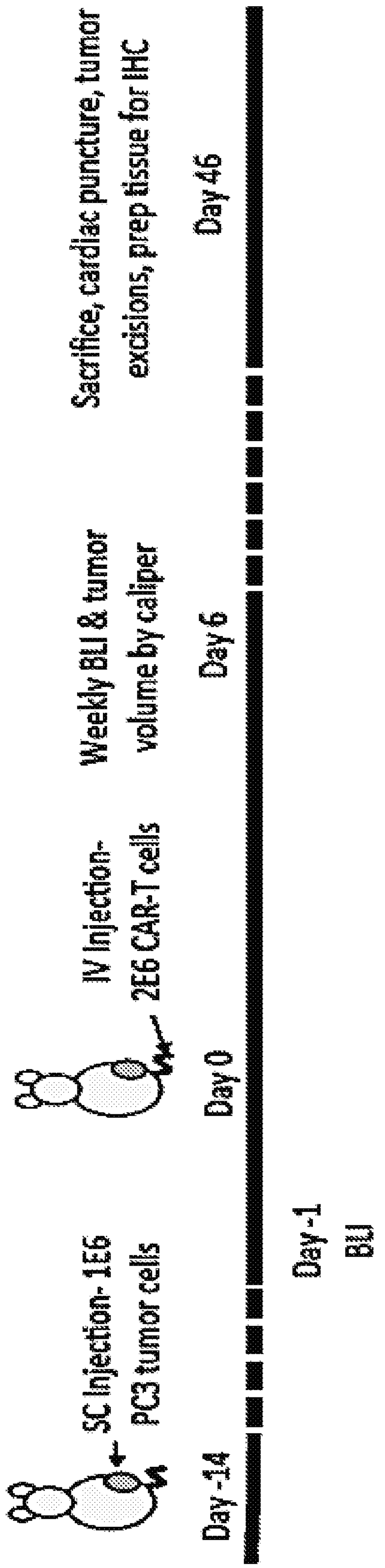
FIG. 20 is a diagram illustrating the setup of a pilot study assessing in vivo efficacy of oncofetal FN-targeting CAR-T cells. Depicted is the workflow of the pilot study from tumor establishment to sacrifice.

In-Vivo Study: One million PC3-CBG-T2A-GFP tumor cells were subcutaneously injected into each of the 20 mice in the cohort (5 mice per group, 4 groups). Tumors were established for 14 days until treatment with CAR-T cell groups NTD, FDC6-BBz, L19-BBz, and 5E5-BBz. On day −1, bioluminescent imaging (BLI) was conducted to obtain baseline imaging of tumors before treatment. On day 0, 2E6 CAR-T cells were administered intravenously through the tail vein of each mouse. Weekly body weigh measurements, BLI and caliper measurements were taken to monitor weight and tumor burden. Mice were sacrificed at Day 46 and tumors were excised and prepped for IHC analysis (in vivo study workflow is illustrated in FIG. 20).

Example 1: Targeting CAR T Cells to the Tumor Microenvironment for the Treatment of Solid Tumors The objective of the present studies was to increase the efficacy of chimeric antigen receptor (CAR)-T cells against solid tumors by designing CARs that target the dense stroma or extracellular matrix (ECM) of the tumor microenvironment. Immune recognition and activation against this physical barrier in the tumor microenvironment may in turn increase recruitment and invasion of the endogenous unmodified immune system, in addition to lysing tumor through cytolytic mechanisms of the engineered tumor-specific CAR-T cells. To this end, CARs that target cancer-specific isoforms of fibronectin (FN) were developed and tested herein.

Figure 18:
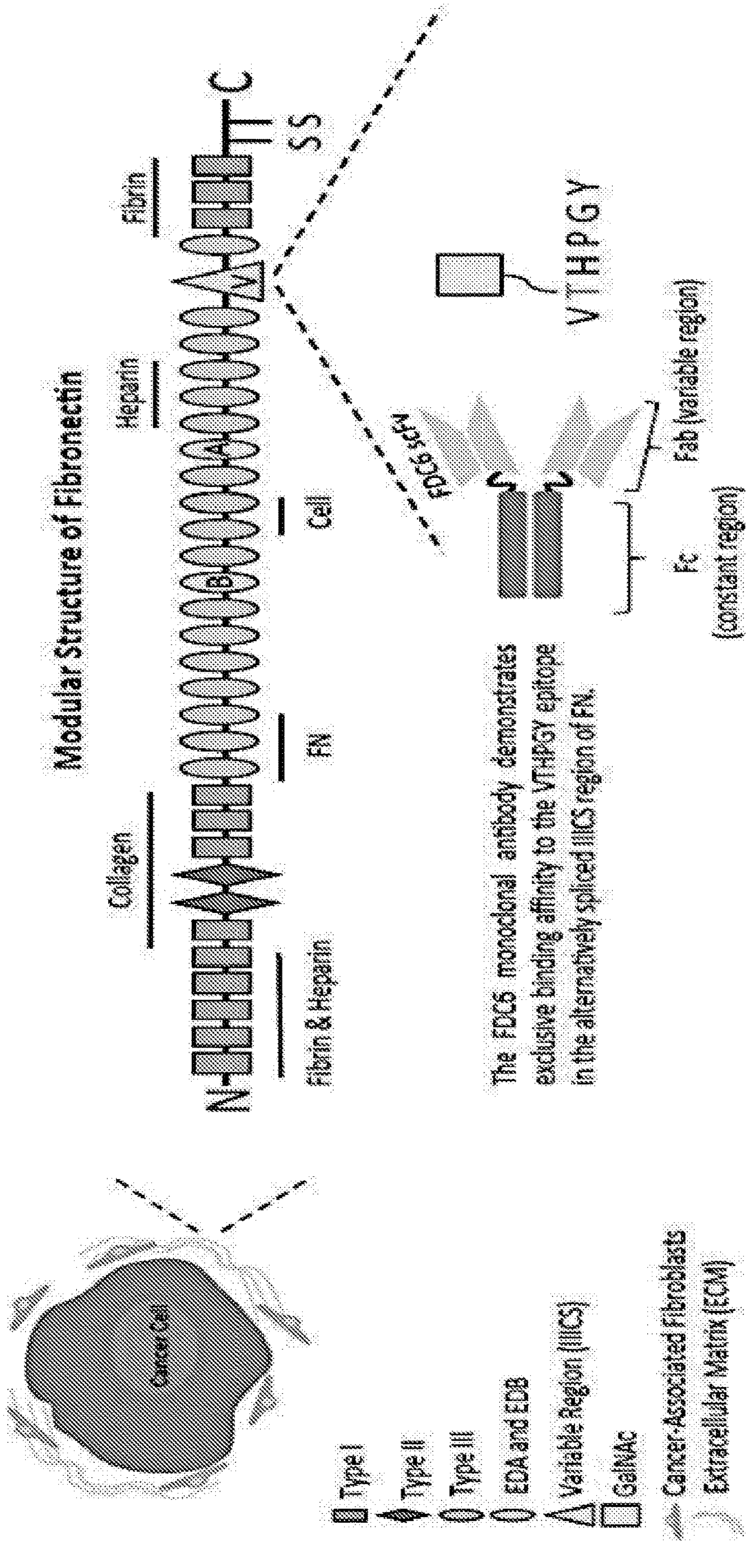
FIG. 18 is a diagram illustrating cancer-specific forms of Fibronectin (FN) including the EDB, EDA, and IIICS domains (adapted from Freire-de-Lima, Front Oncol. 2014; 4:59). FN is a large molecular weight, ubiquitous ECM glycoprotein that exists in multiple isoforms, which are generated through alternative splicing. Of the three alternatively spliced domains (EDB, EDA and IIICS), the EDB and IIICS (or variable domain) are of the highest interest. Previous studies support, and data of the current disclosure corroborates, these cancer-specific isoforms of FN are upregulated in prostate cancer after stimulation with TGFβ. Additionally, the IIICS domain is targetable due to the addition of a covalently-linked GalNAc to the threonine residue of the VTHPGY sequence, creating Tn-antigen, and a well-established antibody is available that recognizes this epitope.

Fibronectin is a large molecular weight, ubiquitous extracellular matrix (ECM) glycoprotein that exists in multiple isoforms, which are generated through alternative splicing. These include three alternatively spliced domains, EDB, EDA, and IIICS (or variable domain) (FIG. 18). These cancer-specific isoforms are upregulated in prostate cancer after stimulation with TGFβ.

Example 2: IIICS-FN-CARs

CARs that target the IIICS domain of fibronectin were developed herein. The IIICS domain has a specific amino acid sequence (VTHPGY) where a covalently-linked GalNAc gets added to the threonine residue, creating the Tn-antigen. The FDC-6 antibody recognizes this epitope exclusively (Matsuura and Hakomori *Proc Natl Acad Sci USA* (1985) 82(19):6517-21).

Figure 2:
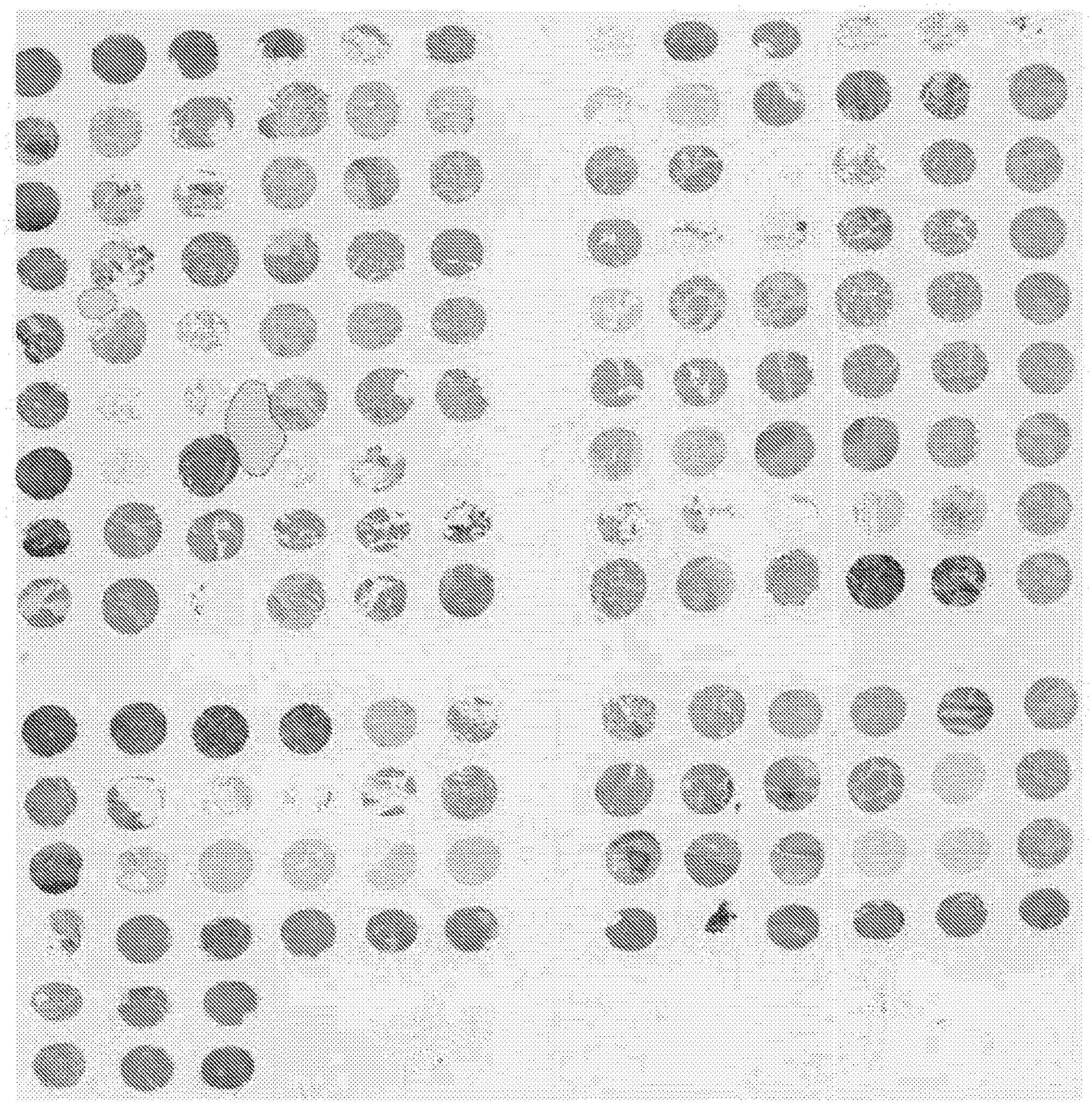
FIG. 2 illustrates the finding that the FDC-6 antibody also reacts to the stroma of many different metastatic prostate tumors. Tumor microarrays of metastatic prostate cancer tumors show the FDC-6 monoclonal antibody reacts to the stroma in metastatic prostate tumor sections.

There are ten different spice variants of oncofetal fibronectin produced through alternative splicing at the IIICS domain. As illustrated in FIG. 1, the FDC-6 antibody reacts highly to oncofetal FN, which is highly present in the stroma of human breast cancer tissue. The FDC-6 antibody also reacts to the stroma of many different metastatic prostate tumors (FIG. 2).

CARs were designed that included scFvs derived from the FDC-6 antibody, a CD8α hinge, a CD8α transmembrane domain, a 4-1BB intracellular domain, and a CD3ζ domain (referred to as FDC-6 CARs or IIICS-FN-CARs)(FIG. 18). One FDC-6 CAR contained the scFv in the orientation of heavy chain variable region to light chain variable region (H>L), and another contained the scFv in the light chain variable region to heavy chain variable region orientation (L>H). The CAR specifically targeted the IIICS domain of fibronectin.

Figure 3:
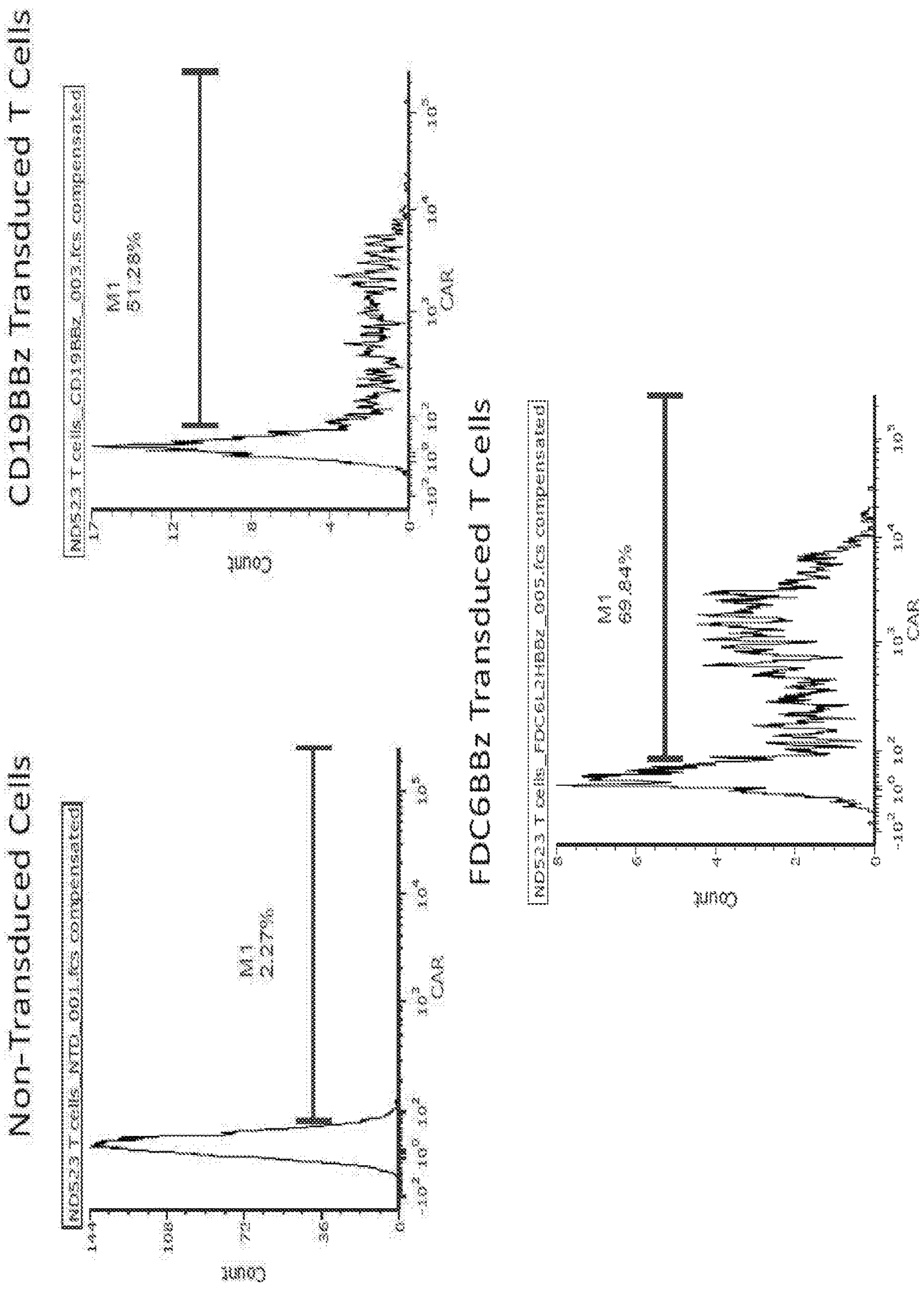
FIG. 3 depicts FDC6-CAR expression on normal donor T cells. After transduction of normal donor T cells with virus containing the FDC6-CAR, the T cells showed a >60% expression of CAR (CAR is detected here by protein L staining). CD19 CAR was used as a control.
Figure 8:
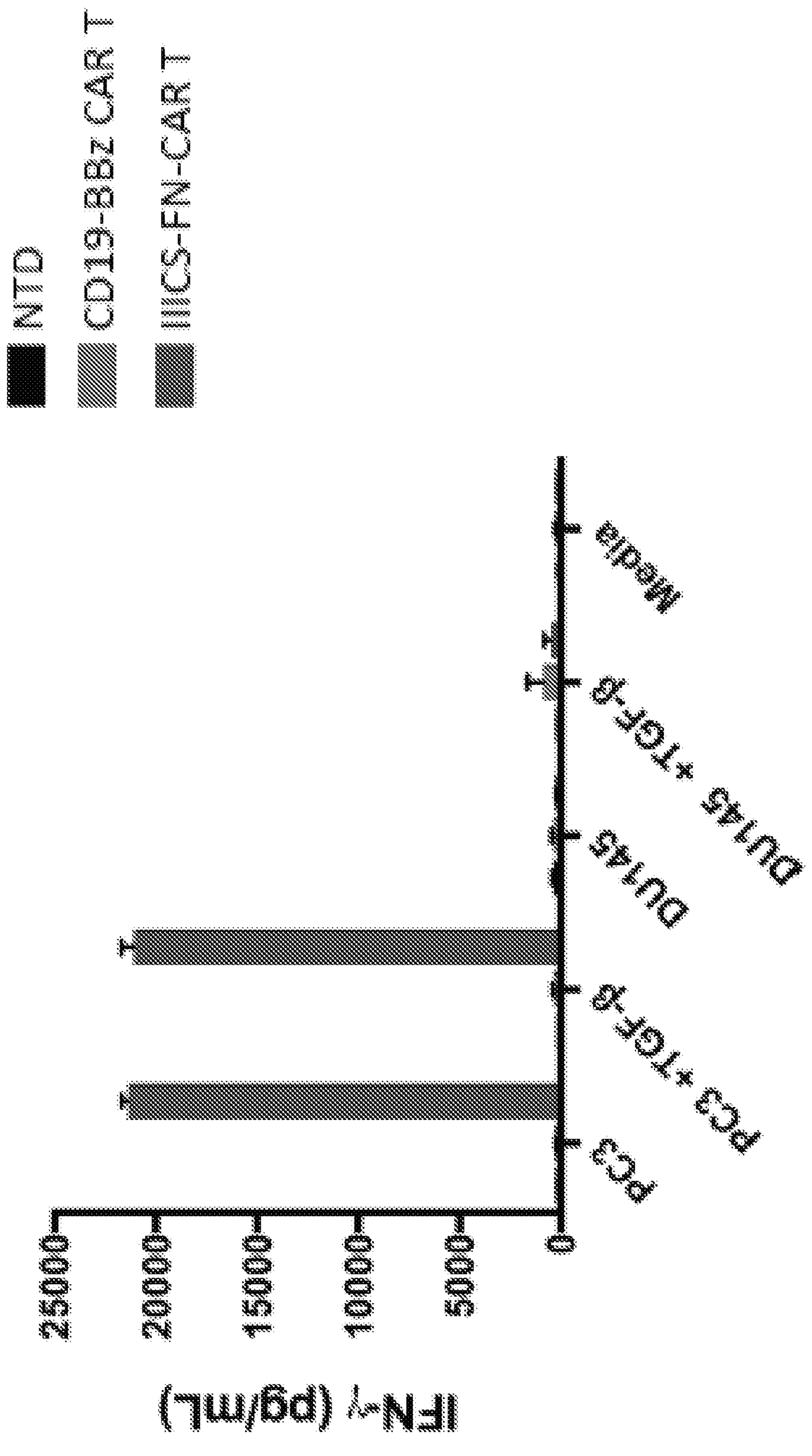
FIG. 8 illustrates the finding that the IIICS-FN-CAR reacts highly to PC3 tumor and no difference is observed in IFN-γ secretion before and after TGFβ stimulation. FDC6-CAR-T cells show specific reactivity against PC3 tumor. There is high IFN-γ secretion when co-cultured with PC3 cells, and the concentration is similar before and after TGF-β stimulation. For this reason, future studies assess activity of the FDC6-CAR against PC3 and DU145 tumor without TGF-β stimulation. Little to no reactivity is demonstrated with FDC6-CAR-T cells against DU145 tumor. CD19-BBz CAR T cells are used here as a non-specific control.

Expression of the FDC6 CAR on normal donor T cells was measured. After transduction of normal donor T cells with virus containing the FDC6-CAR, the T cells showed a >60% expression of the CAR (FIG. 3). The IIICS-FN-CAR reacted highly to PC3 tumor and no difference was observed in IFN-γ secretion before and after TGFβ stimulation (FIG. 8). FDC6-CAR-T cells showed specific reactivity against PC3 tumors. There was high IFN-γ secretion when co-cultured with PC3 cells, and the concentration was similar before and after TGF-β stimulation. For this reason, future studies assessed activity of the FDC6-CAR against PC3 and DU145 tumor without TGF-β stimulation. Little to no reactivity was demonstrated with FDC6-CAR-T cells against DU145 tumor. CD19-BBz CAR T cells are used here as a non-specific control.

Example 3: EDB-FN CARs

CARs that target the EDB domain of fibronectin were also designed and tested herein. The CARs were comprised of an scFv specific for the EDB domain of fibronectin, a CD8α hinge, a CD8α transmembrane domain, a 4-1BB intracellular domain and a CD3ζ domain (referred to as L19 CARs, C6 CARs, or EDB-FN CARs). One C6 CAR contained the scFv in the orientation of heavy chain variable region to light chain variable region (H>L), and another contained the scFv in the light chain variable region to heavy chain variable region orientation (L>H).

Figure 4:
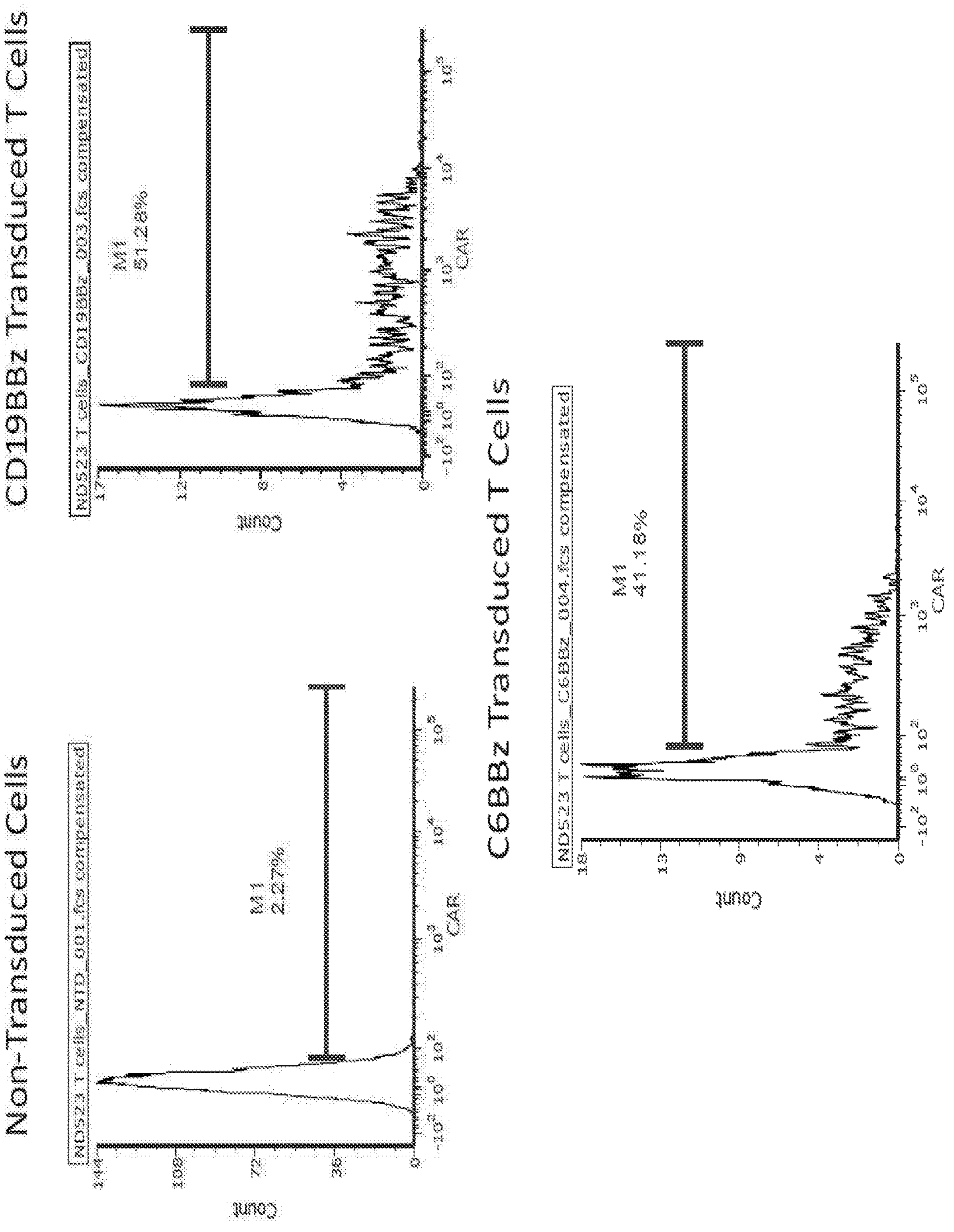
FIG. 4 illustrates C6-CAR expression on normal donor T cells.
Figure 5:
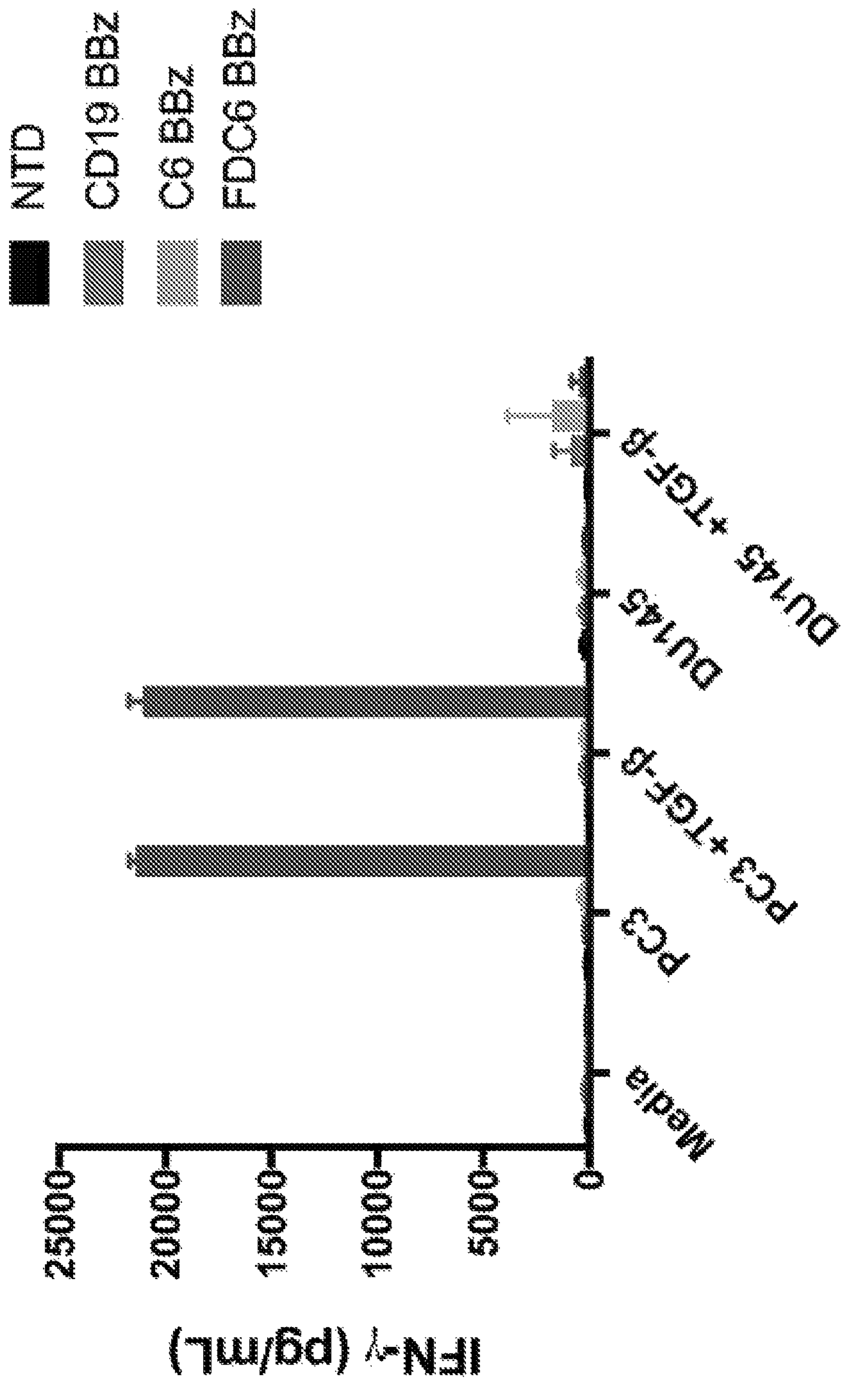
FIG. 5 illustrates the finding that the FDC6-CAR reacts highly to PC3 tumor and no difference is observed in IFN-γ secretion before and after TGFβ stimulation.
Figure 6A:
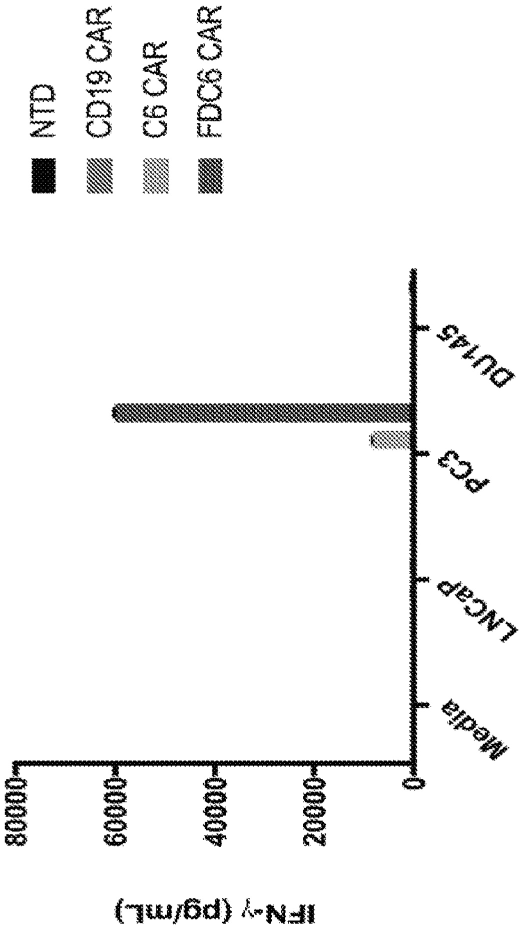
FIGS. 6A-6B illustrate the finding that C6- and FDC6-CARs react to PC3 tumors and show cytotoxic effects and tumor growth impedance.
Figure 6B:
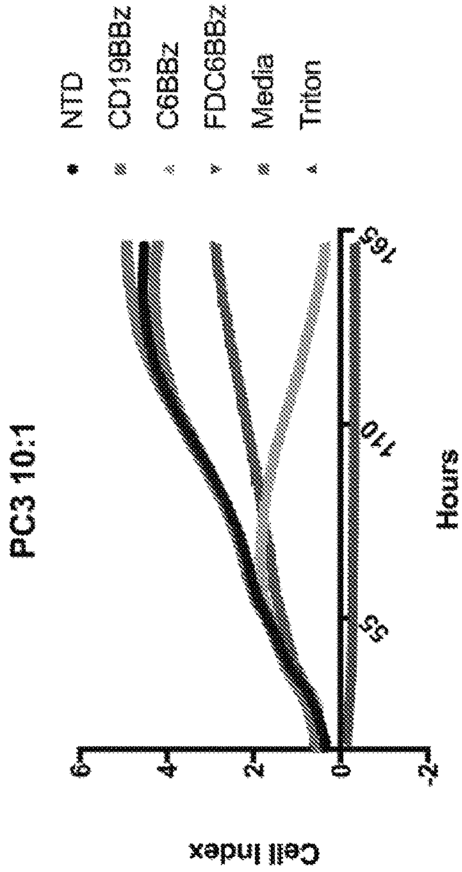

C6 CAR expression was analyzed on normal donor T cells (FIG. 4). The FDC6-CAR reacted highly to PC3 tumor and no difference is observed in IFN-γ secretion before and after TGFβ stimulation (FIG. 5). The C6- and FDC6-CARs reacted to PC3 tumors and show cytotoxic effects and tumor growth impedance (FIGS. 6A-6B). FIG. 6A shows results of a human IFN-γ ELISA illustrating CAR specific reactivity. FIG. 6B shows results from an xCELLigence assay for cytotoxicity.

One L19 CAR contained the scFv in the orientation of heavy chain variable region to light chain variable region (H>L), and another contained the scFv in the light chain variable region to heavy chain variable region orientation (L>H).

Figure 7:
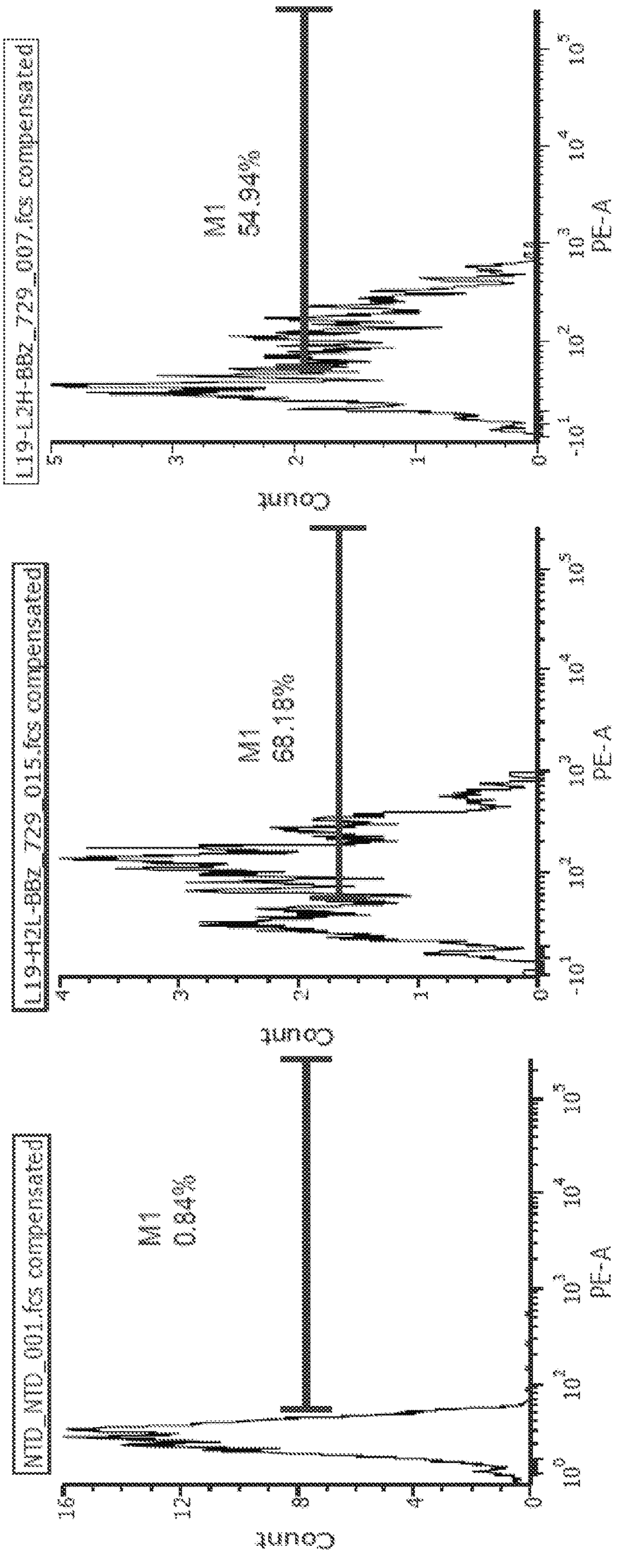
FIG. 7 illustrates L19-CAR expression on SupT1 cells. After transduction of SupT1 cells with virus containing the L19 CARs (with the scFv in the heavy to light, and light to heavy orientation), the cells showed high expression of CAR, detected by protein L staining.

L19-CAR expression on SupT1 cells was measured. After transduction of SupT1 cells with virus containing the L19 CARs (with the scFv in the heavy to light, and light to heavy orientation), the cells showed high expression of CAR, detected by protein L staining (FIG. 7).

Example 4: Testing Fibronectin CARs In Vitro and In Vivo

Figure 9:
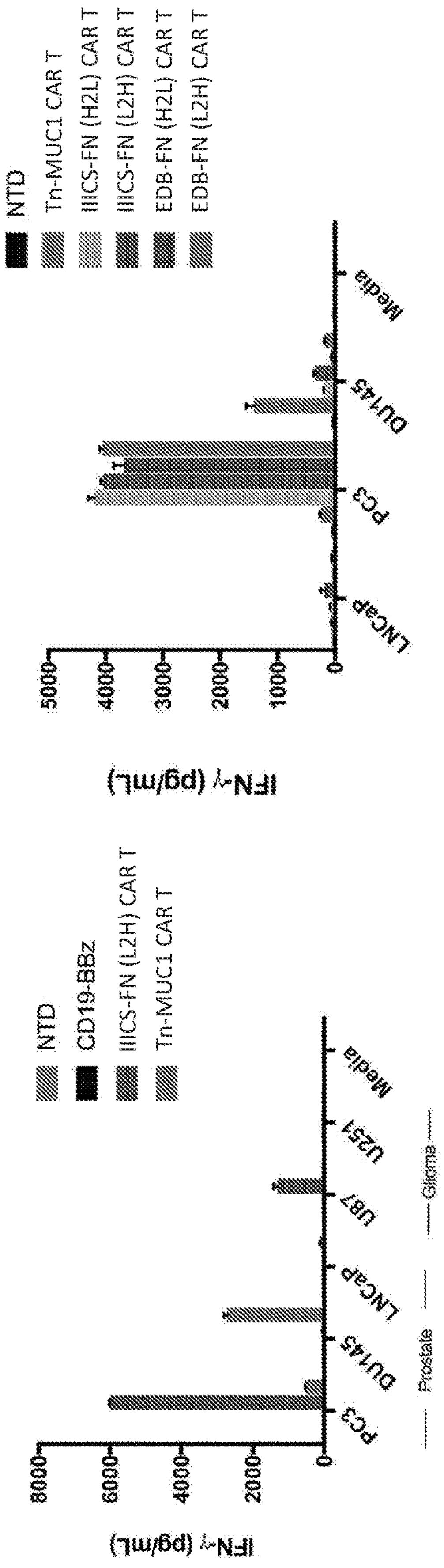
FIG. 9 illustrates the finding that fibronectin CAR T cells and TnMUC1 CAR T cells are reactive against metastatic prostate cancer lines. FD6 and L19 directed CAR-T cells show high IFN-γ secretion when co-cultured with PC3 tumor specifically, but little to none against LNCaP or DU145. Whereas, the well-defined TnMUC1 targeting CAR-T cells (5E5-CD2z CAR) exhibited a greater reactivity against DU145 tumor compared to PC3 and LNCaP.

Fibronectin CAR T cells and TnMUC1 CAR T cells were demonstrated to be reactive against metastatic prostate cancer lines (FIG. 9). FDC6 and L19 directed CAR-T cells showed high IFN-γ secretion when co-cultured with PC3 tumor specifically, but little to none against LNCaP or DU145. Whereas, the well-defined TnMUC1 targeting CAR-T cells (5E5-CD2z CAR) exhibited a greater reactivity against DU145 tumor compared to PC3 and LNCaP (FIG. 9).

Figure 10:
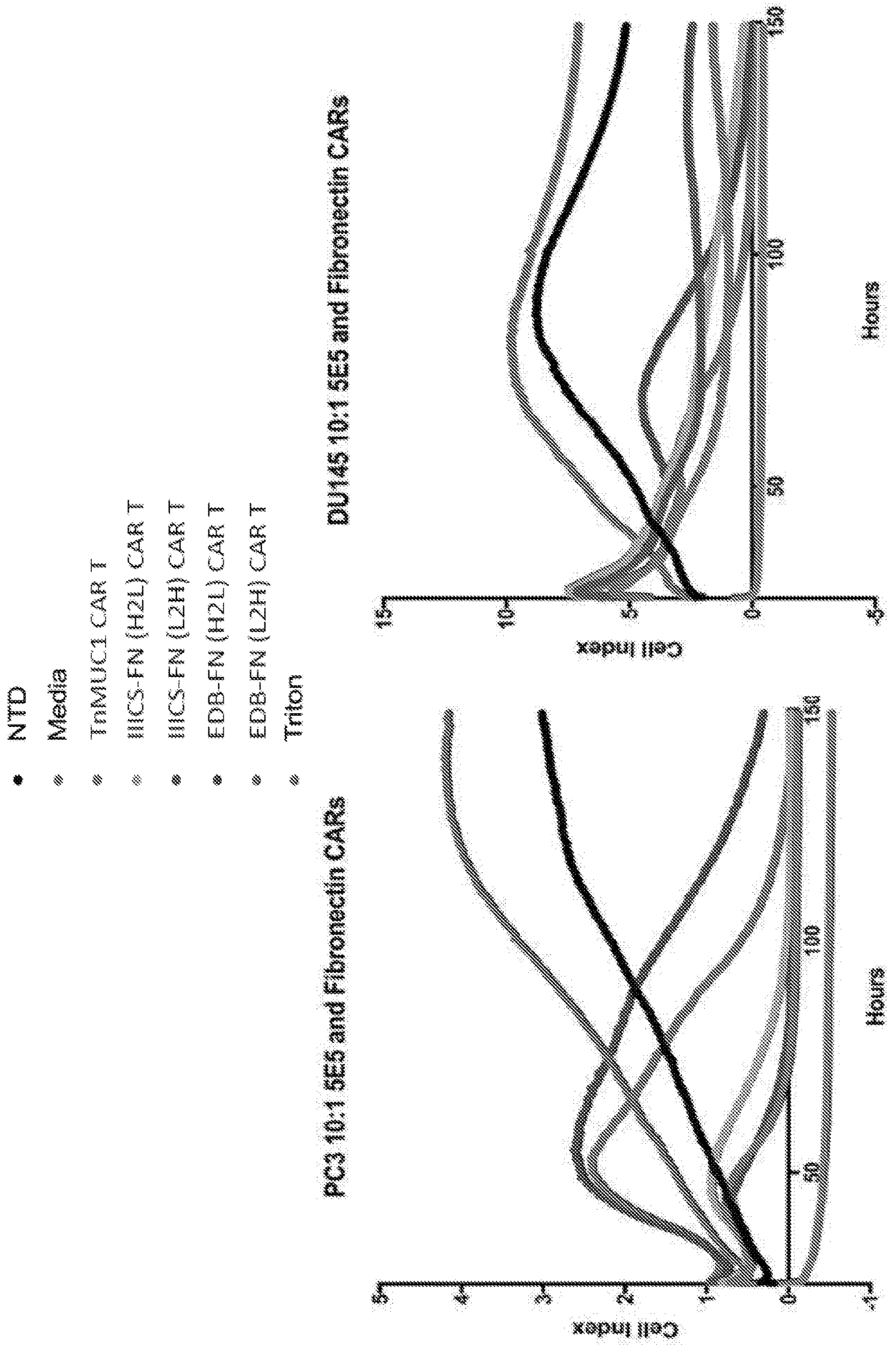
FIG. 10 illustrates the finding that fibronectin CAR-T cells exhibit cytotoxic effects comparable to that observed with TnMUC1 CAR-T cells against aggressive prostate cancer cell lines at a high E:T ratio. Cytotoxicity was assessed using xCELLigence RTCA system.
Figure 11:
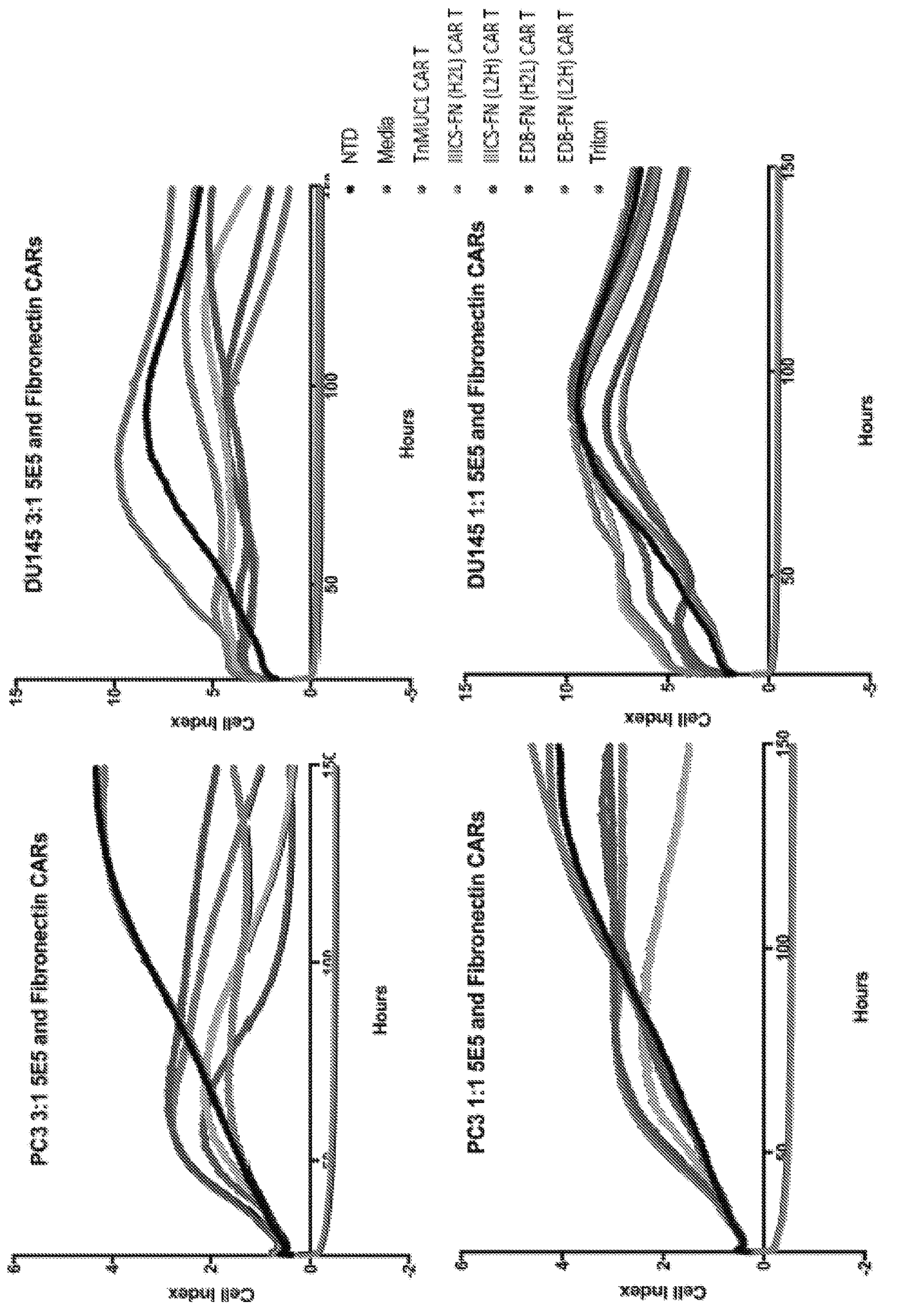
FIG. 11 illustrates the finding that fibronectin CAR-T cells exhibit better control of tumor growth than TnMUC1 CAR-T cells against aggressive prostate cancer cell lines at lower E:T ratios. Fibronectin CAR-T cells demonstrate better tumor growth impedance at low E:T ratios (3:1 and 1:1) against metastatic prostate cancer compared to TnMUC1 targeting CAR-T cells. Cytotoxicity was monitored using the xCELLigence RTCA system.

Fibronectin CAR-T cells exhibited cytotoxic effects comparable to that observed with TnMUC1 CAR-T cells against aggressive prostate cancer cell lines at a high E:T ratio. Cytotoxicity was assessed using xCELLigence RTCA system (FIG. 10). Additionally, fibronectin CAR-T cells exhibited better control of tumor growth than TnMUC1 CAR-T cells against aggressive prostate cancer cell lines at lower E:T ratios (3:1 and 1:1) (FIG. 11).

Figure 12:
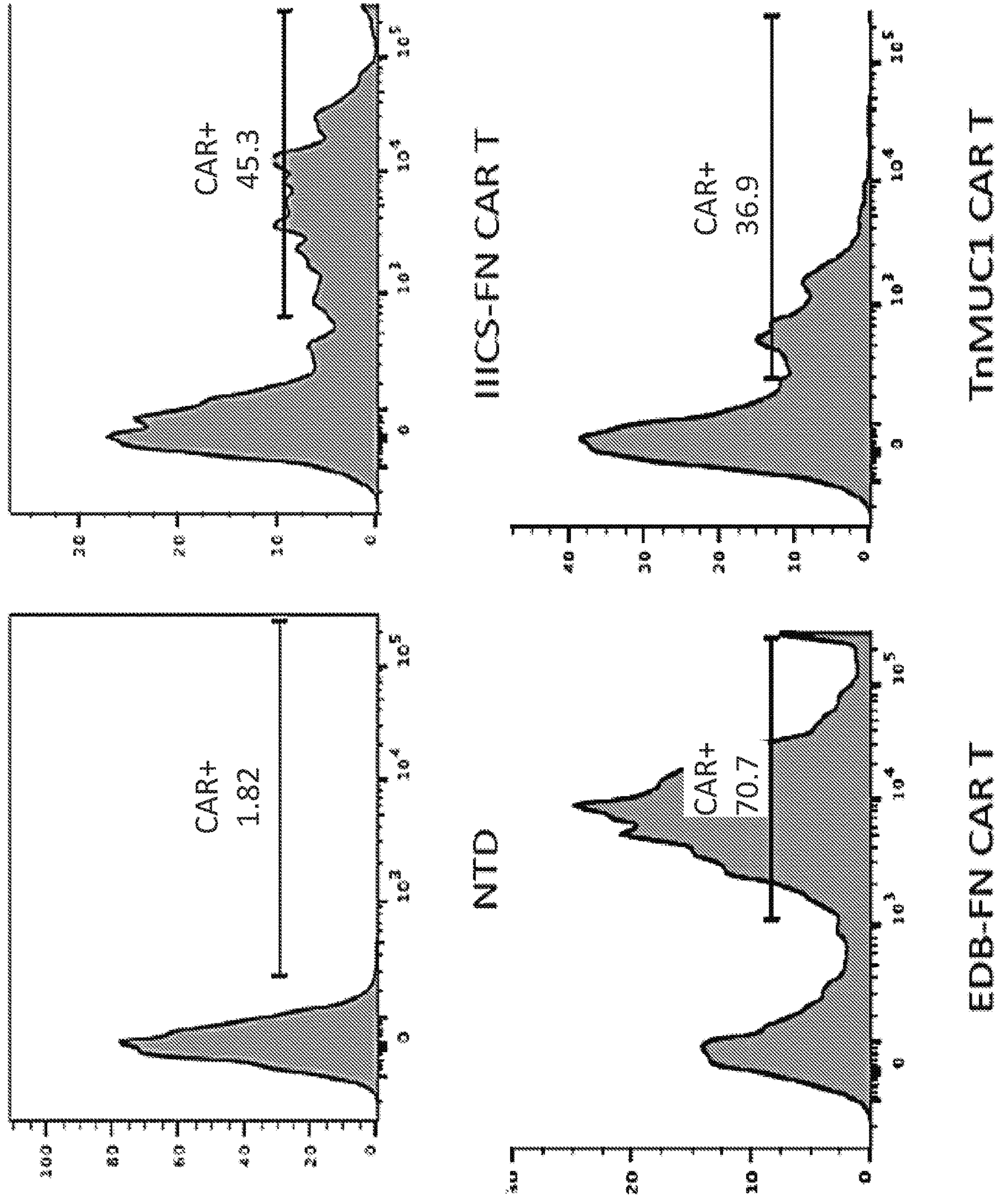
FIG. 12 illustrates CAR expression on ND510 T cells IV injected into NSG mice. Flow cytometry histograms showing CAR expression of each T cell group used in the in-vivo study. CARs were assessed by protein L immunostaining.

CAR expression was measured on ND510 T cells i.v. injected into NSG mice. Flow cytometry histograms show CAR expression of each T cell group used in the in vivo study. CARs were assessed by protein L immunostaining (FIG. 12).

Figure 13:
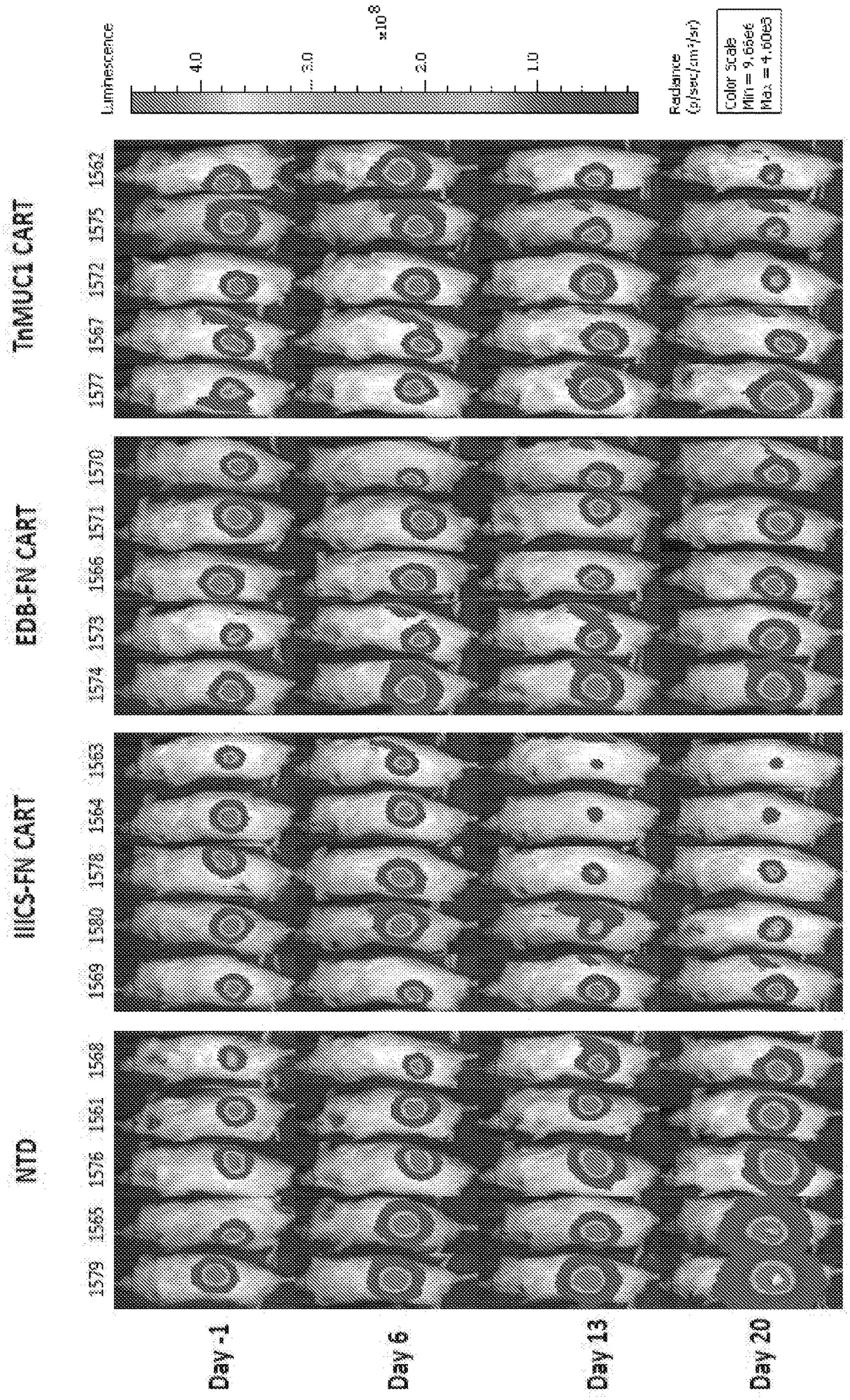
FIG. 13 depicts serial bioluminescence imaging (BLI) of PC3 tumors in NSG mice. Mice were treated with CAR-T cells on day 0. Mice were randomized at day −1 into tumor groups but caging remained the same.

NSG mice were treated with CAR-T cells on day 0 then serial bioluminescence imaging (BLI) of PC3 tumors was performed (FIG. 13).

Figure 14A:
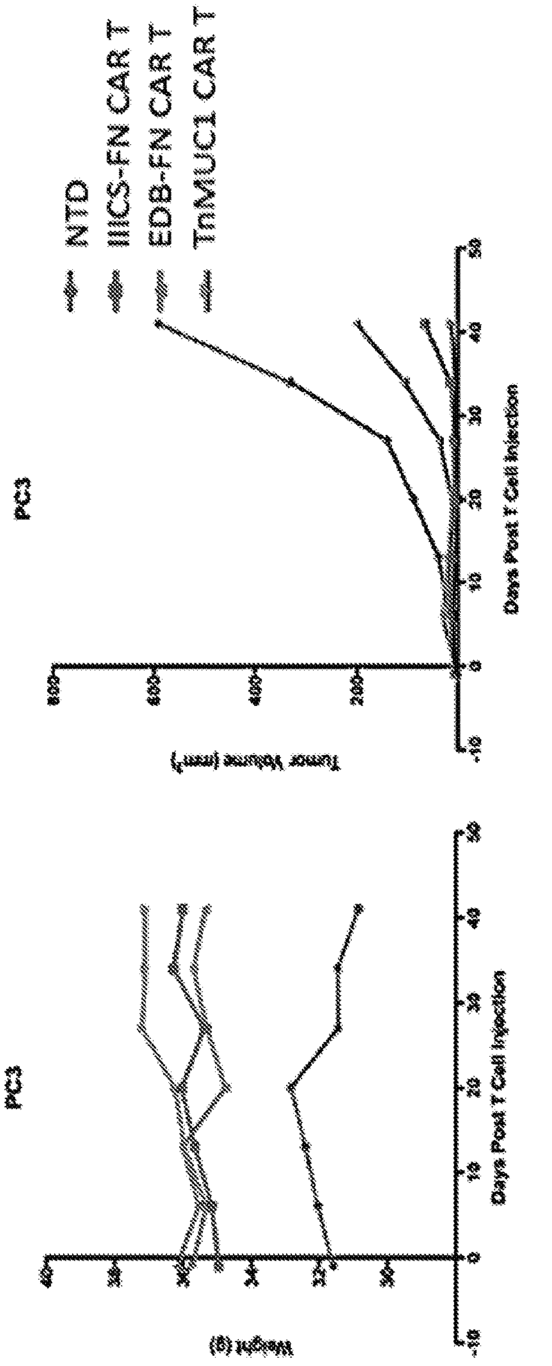
FIGS. 14A-14C illustrate the finding that anti-FN CAR-T cells promote rapid anti-tumor rejection.
Figure 14B:
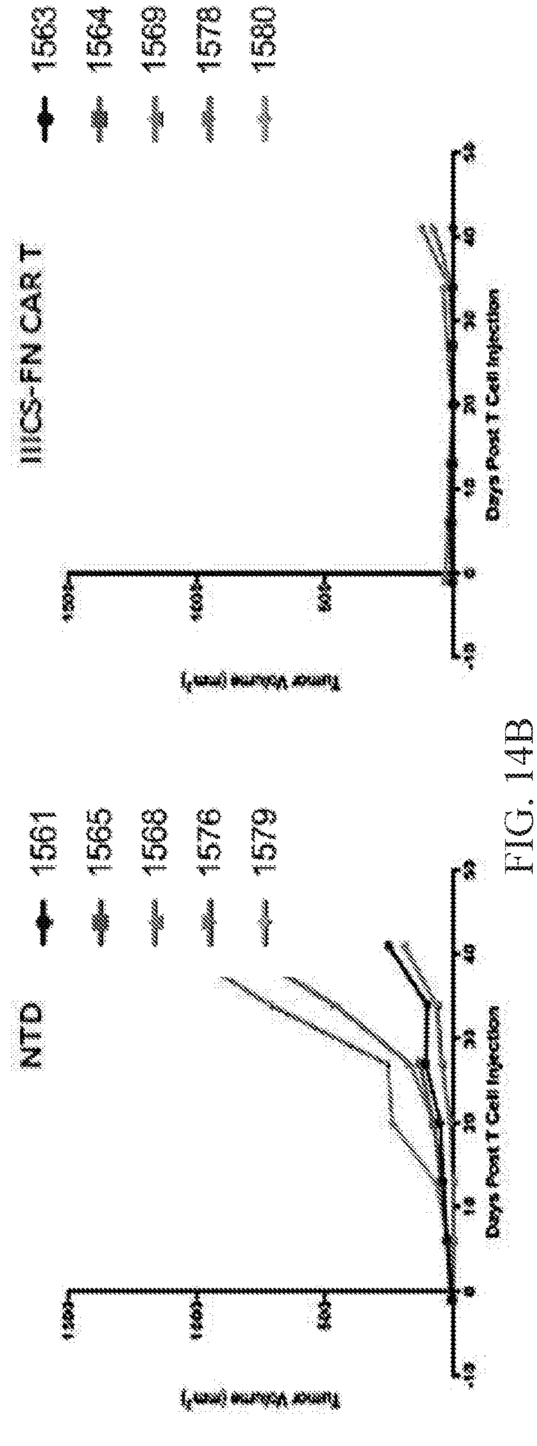
Figure 14C:
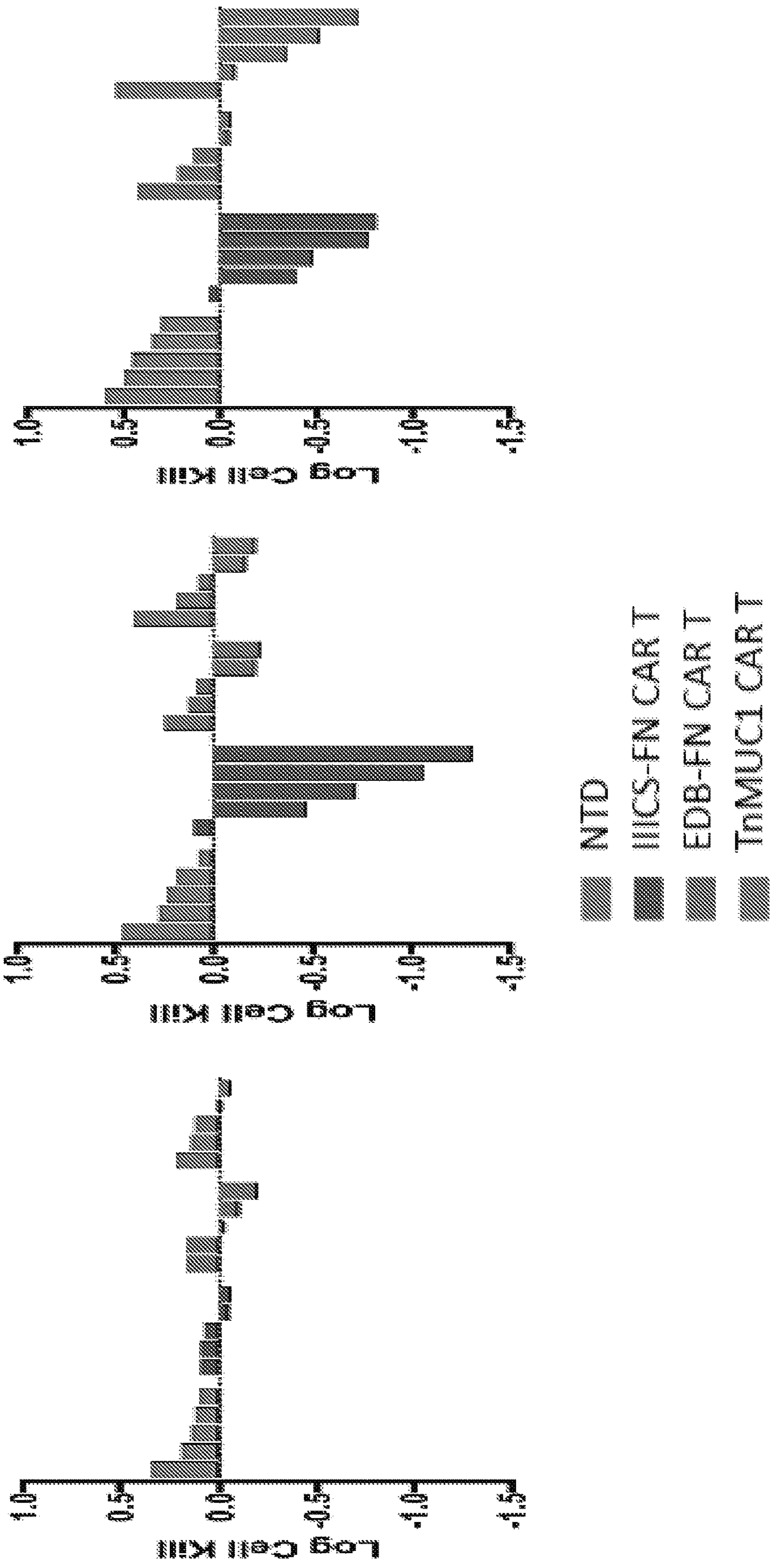

Anti-IIICS-FN CAR-T cells promote rapid anti-tumor rejection (FIGS. 14A-14C). FIG. 14A shows weekly body weight (grams) and tumor volume (derived by caliper measurement) of each group. FIG. 14B shows weekly tumor volume of each mouse in the NTD group compared to the IIICS-FN CAR T cell group. FIG. 14C shows Log-fold change in tumor BLI overtime.

Figure 15:
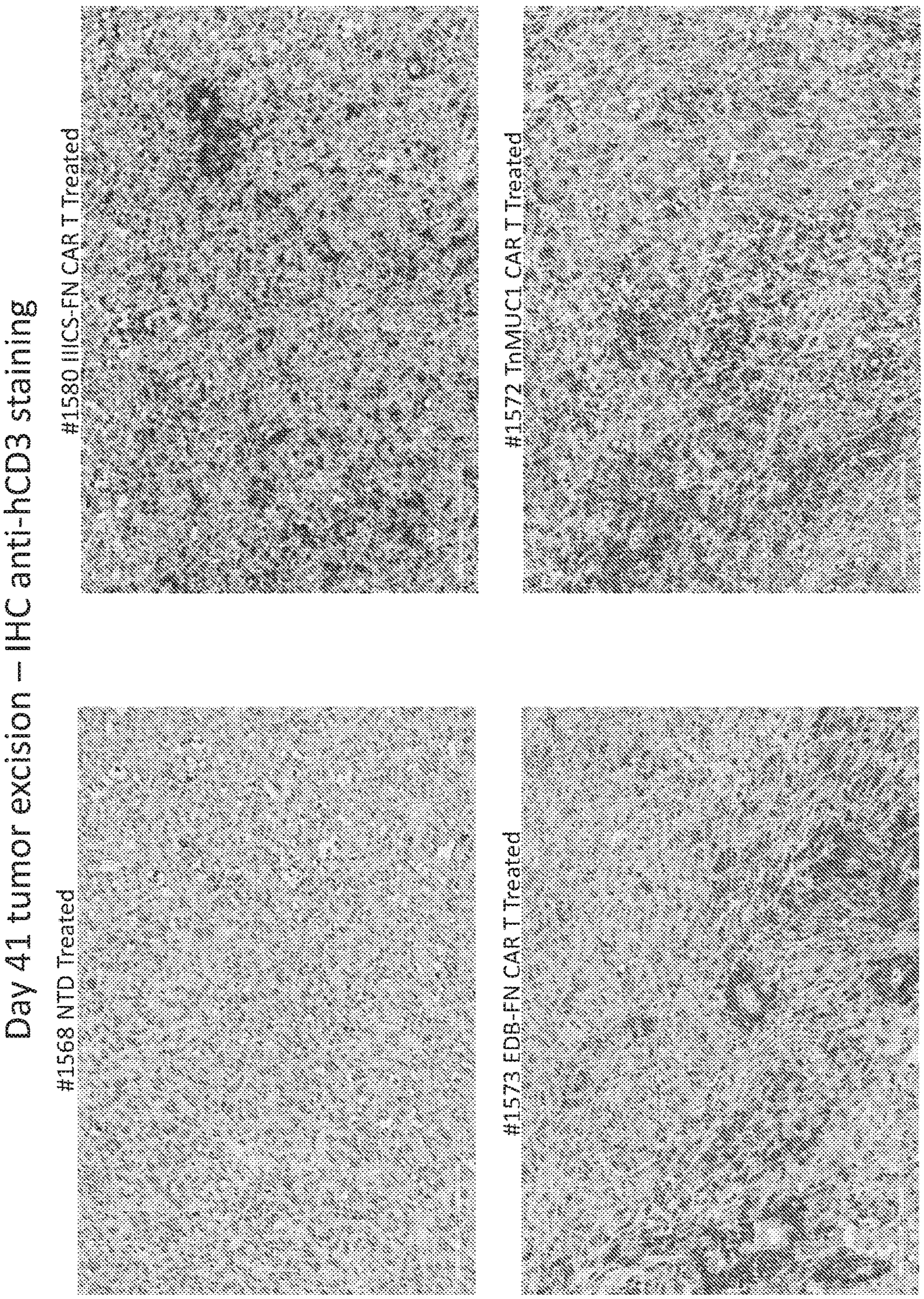
FIG. 15 illustrates superior T cell infiltration into tumors treated with either IICS-FN, EDB-FN, or TnMUC1 targeting CAR-T cells compared with NTD controls, as evidenced by immunohistochemical staining (representative images).

Immunohistochemical staining of hCD3 demonstrates T cell infiltration in PC3 tumors treated with either IIICS-FN, EDB-FN, or TnMUC1 CAR T cells (FIG. 15), demonstrating superior T cell infiltration into tumors treated with the CAR-T groups compared to NTD T cells.

Figure 16:
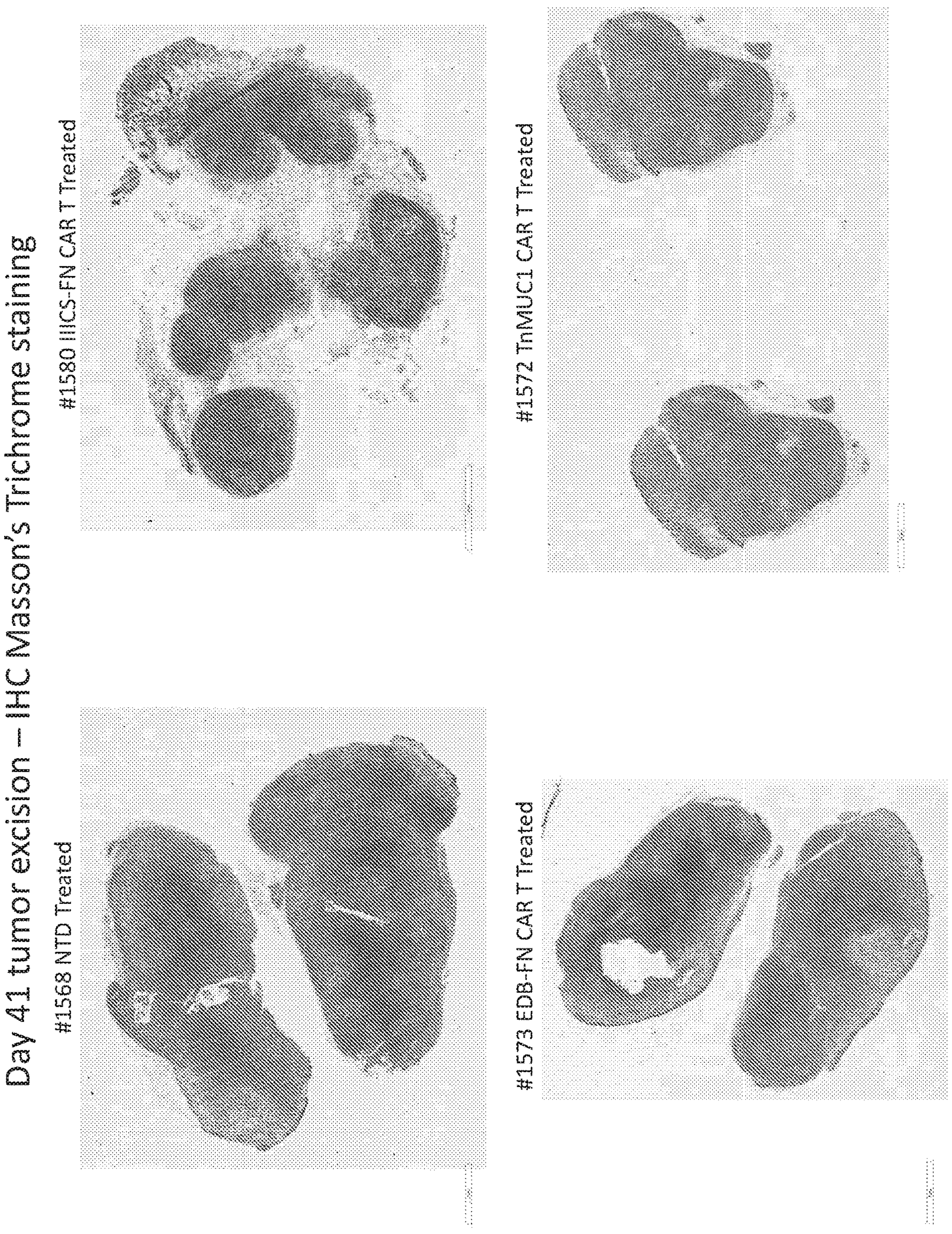
FIG. 16 illustrates Masson's Trichrome staining on PC3 tumors treated with each effector group. This demonstrates the superior tumor reduction elicited by IIICS-FN and TnMUC1 targeting CAR-T cells compared to NTD T cells and EDB-FN targeting CAR-T cells, as evidenced cytoplasm reduction (red stain) with visible collagen deposits (blue stain) remaining in tumors treated with IIICS-FN CAR-T cells and Tn-MUC1 CAR-T cells (representative images).

Masson's Trichrome stain on PC3 tumors sections treated with either NTD T cells or IIICS-FN, EDB-FN, or TnMUC1 CAR T cells (FIG. 16) show clear tumor reduction, as indicated by the cytoplasm recession (red stain) with visible collagen deposits (blue stain) remaining, in the tumors treated with both IIICS-FN and TnMUC1 CAR T cells compared to tumors treated with NTD T cells and EDB-FN CAR T cells.

Figure 17A:
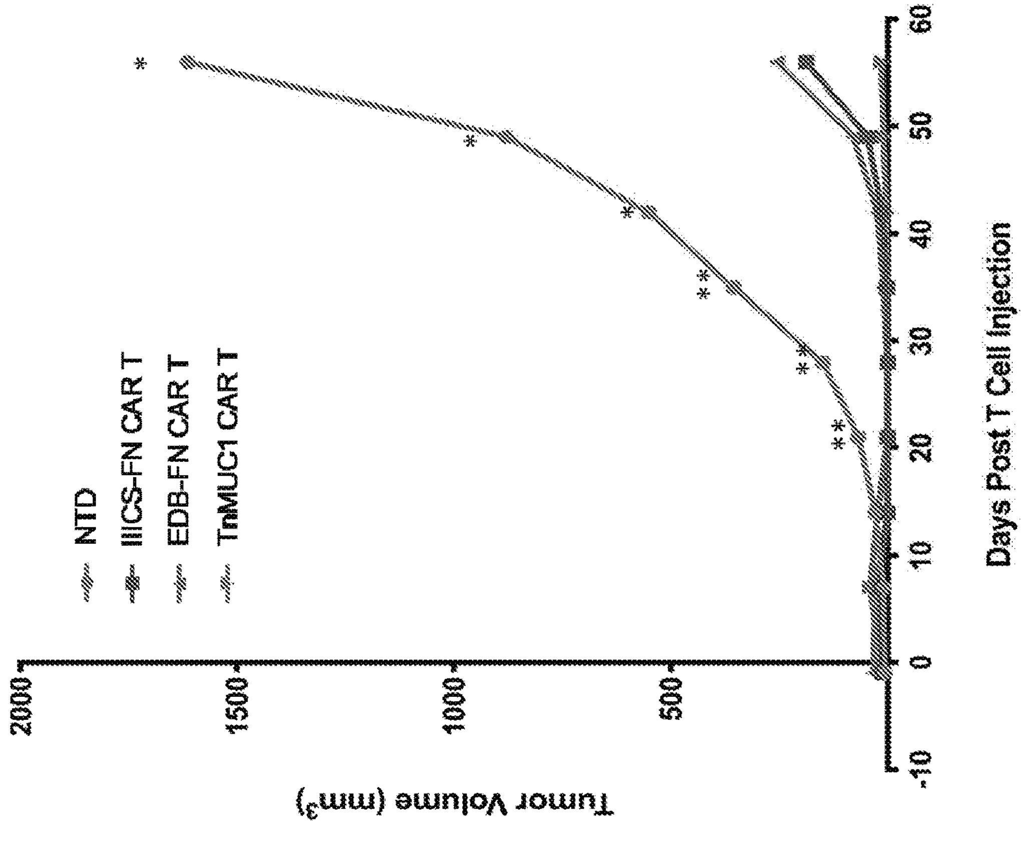
FIGS. 17A-B demonstrate that FN and TnMUC-1 targeting CAR-T cells promote rapid tumor rejection and better control of tumor growth overtime compared to tumors treated with NTD T-cells.
Figure 17B:
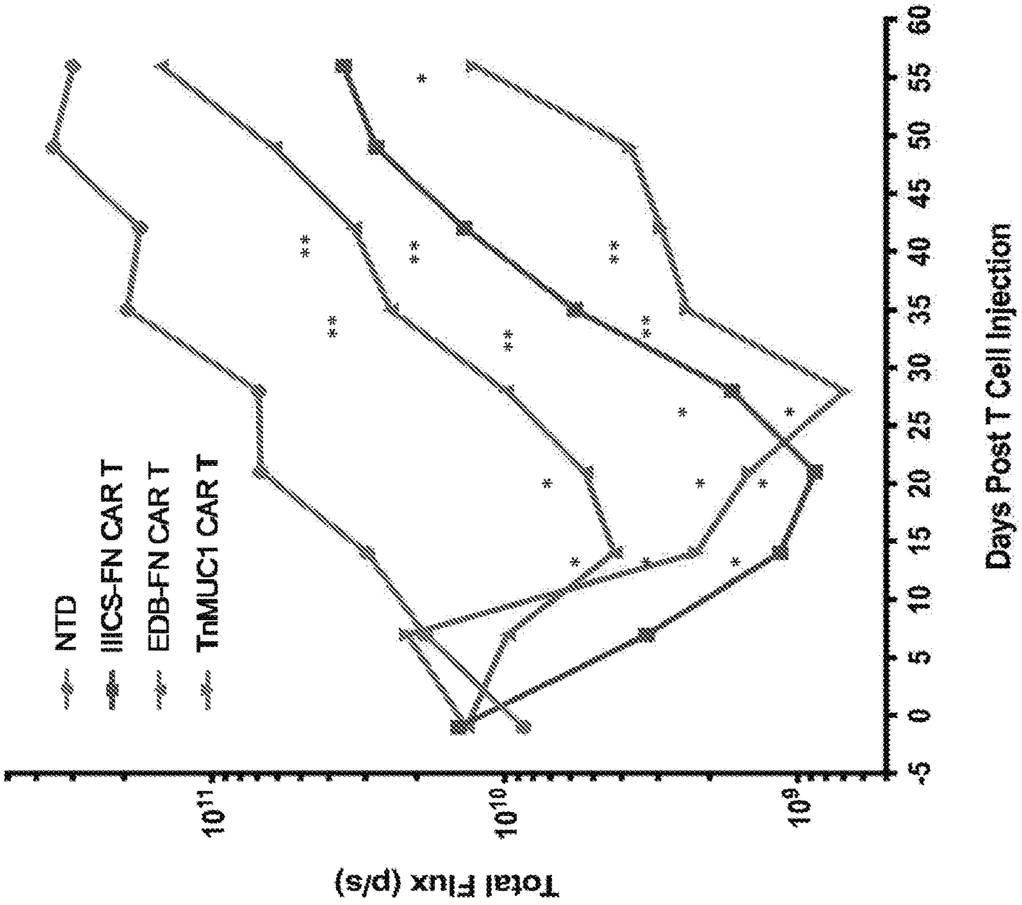

The NSG model depicted in FIGS. 13-14 was repeated and the results of the more statistically robust model are shown in FIG. 17 (n=8-10 animal per group). The findings in FIGS. 17A-B further support those presented in FIGS. 13-14. FIGS., demonstrating that FN and TnMUC-1 targeting CAR-T cells promote rapid tumor rejection and better control of tumor growth overtime compared to tumors treated with NTD T-cells.

Enumerated Embodiments

The following enumerated embodiments are provided, the numbering of which is not to be construed as designating levels of importance.

Embodiment 1 provides a chimeric antigen receptor (CAR) comprising an antigen binding domain capable of binding the IIICS domain of fibronectin, a transmembrane domain, and an intracellular domain.

Embodiment 2 provides the CAR of embodiment 1, wherein the antigen binding domain comprises at least one heavy chain variable region (HCDR) comprising the nucleotide sequence selected from the group consisting of SEQ ID NO: 1, SEQ ID NO: 2, and SEQ ID NO: 3.

Embodiment 3 provides the CAR of embodiment 1 or embodiment 2, wherein the antigen binding domain comprises at least one light chain variable region (LCDR) comprising the nucleotide sequence selected from the group consisting of SEQ ID NO: 4, SEQ ID NO: 5, and SEQ ID NO: 6.

Embodiment 4 The CAR of any one of embodiments 1-3, wherein the antigen binding domain comprises a heavy chain variable region comprising an amino acid sequence at least 80%, 85%, 90%, 95%, 96%, 97%, 98%, 99%, or 100% identical to SEQ ID NO: 7.

Embodiment 5 provides the CAR of any one of embodiments 1-4, wherein the antigen binding domain comprises a light chain variable region comprising an amino acid sequence at least 80%, 85%, 90%, 95%, 96%, 97%, 98%, 99%, or 100% identical to SEQ ID NO: 8.

Embodiment 6 provides the CAR of any one of embodiments of 1-5, wherein the antigen binding domain is a single-chain variable fragment (scFv) comprising an amino acid sequence at least 80%, 85%, 90%, 95%, 96%, 97%, 98%, 99%, or 100% identical to SEQ ID NO: 10 or SEQ ID NO: 11.

Embodiment 7 provides a chimeric antigen receptor (CAR) comprising an antigen binding domain capable of binding the EDB domain of fibronectin, a transmembrane domain, and an intracellular domain.

Embodiment 8 provides the CAR of embodiment 7, wherein the antigen binding domain comprises at least one heavy chain variable region (HCDR) comprising the nucleotide sequence selected from the group consisting of SEQ ID NO: 12, SEQ ID NO: 13, and SEQ ID NO: 14.

Embodiment 9 provides the CAR of embodiment 7 or embodiment 8, wherein the antigen binding domain comprises at least one light chain variable region (LCDR) comprising the nucleotide sequence selected from the group consisting of SEQ ID NO: 15, SEQ ID NO: 16, and SEQ ID NO: 17.

Embodiment 10 provides the CAR of any one of embodiments 7-9, wherein the antigen binding domain comprises a heavy chain variable region comprising an amino acid sequence at least 80%, 85%, 90%, 95%, 96%, 97%, 98%, 99%, or 100% identical to SEQ ID NO: 18.

Embodiment 11 provides the CAR of any one of embodiments 7-10, wherein the antigen binding domain comprises a light chain variable region comprising an amino acid sequence at least 80%, 85%, 90%, 95%, 96%, 97%, 98%, 99%, or 100% identical to SEQ ID NO: 19.

Embodiment 12 provides the CAR of embodiment 7, wherein the antigen binding domain comprises at least one heavy chain variable region (HCDR) comprising the nucleotide sequence selected from the group consisting of SEQ ID NO: 23, SEQ ID NO: 24, and SEQ ID NO: 25.

Embodiment 13 provides the CAR of embodiment 7 or 12, wherein the antigen binding domain comprises at least one light chain variable region (LCDR) comprising the nucleotide sequence selected from the group consisting of SEQ ID NO: 26, SEQ ID NO: 27, and SEQ ID NO: 28.

Embodiment 14 provides the CAR of any one of embodiments 7, 12, or 13, wherein the antigen binding domain comprises a heavy chain variable region comprising an amino acid sequence at least 80%, 85%, 90%, 95%, 96%, 97%, 98%, 99%, or 100% identical to SEQ ID NO: 29.

Embodiment 15 provides the CAR of any one of embodiments 7, 12, 13, or 14, wherein the antigen binding domain comprises a light chain variable region comprising an amino acid sequence at least 80%, 85%, 90%, 95%, 96%, 97%, 98%, 99%, or 100% identical to SEQ ID NO: 30.

Embodiment 16 provides the CAR of any one of embodiments 7, 12, 13, 14, or 15, wherein the antigen binding domain is a single-chain variable fragment (scFv) comprising an amino acid sequence at least 80%, 85%, 90%, 95%, 96%, 97%, 98%, 99%, or 100% identical to SEQ ID NO: 31 or SEQ ID NO: 32.

Embodiment 17 provides the CAR of any of the preceding embodiments, wherein the antigen binding domain is selected from the group consisting of a full length antibody or antigen-binding fragment thereof, a Fab, a single-chain variable fragment (scFv), or a single-domain antibody.

Embodiment 18 provides the CAR of any of the preceding embodiments, wherein the CAR further comprises a CD8 alpha hinge sequence comprising the amino acid sequence set forth in SEQ ID NO: 34.

Embodiment 19 provides the CAR of any of the preceding embodiments, wherein the transmembrane domain comprises a transmembrane domain selected from the group consisting of an artificial hydrophobic sequence, and a transmembrane domain of a type I transmembrane protein, an alpha, beta, or zeta chain of a T cell receptor, CD28, CD3 epsilon, CD45, CD4, CD5, CD8, CD9, CD16, CD22, CD33, CD37, CD64, CD80, CD86, OX40 (CD134), 4-1BB (CD137), ICOS, and CD154, or a transmembrane domain derived from a killer immunoglobulin-like receptor (KIR).

Embodiment 20 provides the CAR of any of the preceding embodiments, wherein the transmembrane domain comprises a transmembrane domain of CD8 alpha comprising the amino acid sequence set forth in SEQ ID NO: 35.

Embodiment 21 provides the CAR of any of the preceding embodiments, wherein the intracellular domain comprises a costimulatory signaling domain and an intracellular signaling domain.

Embodiment 22 provides the CAR of any of the preceding embodiments, wherein the intracellular domain comprises a costimulatory domain of a protein selected from the group consisting of proteins in the TNFR superfamily, CD28, 4-1BB (CD137), OX40 (CD134), PD-1, CD7, LIGHT, CD83L, DAP10, DAP12, CD27, CD2, CD5, ICAM-1, LFA-1, Lck, TNFR-I, TNFR-II, Fas, CD30, CD40, ICOS, NKG2C, and B7-H3 (CD276), or a variant thereof, or an intracellular domain derived from a killer immunoglobulin-like receptor (KIR).

Embodiment 23 provides the CAR of any of the preceding embodiments, wherein the intracellular domain comprises a costimulatory domain of 4-1BB.

Embodiment 24 provides the CAR of embodiments 23, wherein the costimulatory domain of 4-1BB comprises the amino acid sequence set forth in SEQ ID NO: 36.

Embodiment 25 provides the CAR of any of the preceding embodiments, wherein the intracellular signaling domain comprises an intracellular domain selected from the group consisting of cytoplasmic signaling domains of a human CD3 zeta chain (CD3), FcγRIII, FcsRI, a cytoplasmic tail of an Fc receptor, an immunoreceptor tyrosine-based activation motif (ITAM) bearing cytoplasmic receptor, TCR zeta, FcR gamma, CD3 gamma, CD3 delta, CD3 epsilon, CD5, CD22, CD79a, CD79b, and CD66d, or a variant thereof.

Embodiment 26 provides the CAR of any of the preceding embodiments, wherein the intracellular signaling domain comprises an intracellular domain of CD3 or a variant thereof.

Embodiment 27 provides the CAR of embodiment 26, wherein the intracellular domain of CD3ζ comprises the amino acid sequence set forth in SEQ ID NO: 37.

Embodiment 28 provides the CAR of any of the preceding embodiments, wherein the CAR comprises an amino acid sequence at least 80%, 85%, 90%, 95%, 96%, 97%, 98%, 99%, or 100% identical to SEQ ID NO: 38, 39, 40, 41, 42, or 43.

Embodiment 29 provides the CAR of any of the preceding embodiments, wherein the CAR is encoded by a nucleotide sequence at least 80%, 85%, 90%, 95%, 96%, 97%, 98%, 99%, or 100% identical to SEQ ID NO: 48, 49, 54, 55, 60, or 61.

Embodiment 30 provides a nucleic acid comprising a polynucleotide sequence encoding a chimeric antigen receptor (CAR), wherein the CAR comprises an antigen binding domain capable of binding the IIICS domain of fibronectin, a transmembrane domain, and an intracellular domain.

Embodiment 31 provides the nucleic acid of embodiment 30, wherein the antigen binding domain comprises a heavy chain variable region encoded by a nucleotide sequence at least 80%, 85%, 90%, 95%, 96%, 97%, 98%, 99%, or 100% identical to SEQ ID NO: 44 and/or a light chain variable region encoded by a nucleotide sequence at least 80%, 85%, 90%, 95%, 96%, 97%, 98%, 99%, or 100% identical to SEQ ID NO: 45.

Embodiment 32 provides the nucleic acid of embodiment 30, wherein the antigen binding domain is a single-chain variable fragment (scFv) encoded by a nucleotide sequence at least 80%, 85%, 90%, 95%, 96%, 97%, 98%, 99%, or 100% identical to SEQ ID NO: 46 or SEQ ID NO: 47.

Embodiment 33 provides the nucleic acid of embodiment 30, wherein the CAR is encoded by a nucleotide sequence at least 80%, 85%, 90%, 95%, 96%, 97%, 98%, 99%, or 100% identical to SEQ ID NO: 48 or 49.

Embodiment 34 provides a nucleic acid comprising a polynucleotide sequence encoding a CAR, wherein the CAR comprises an antigen binding domain capable of binding the EDB domain of fibronectin, a transmembrane domain, and an intracellular domain.

Embodiment 35 provides the nucleic acid of embodiment 34, wherein the antigen binding domain comprises a heavy chain variable region encoded by a nucleotide sequence at least 80%, 85%, 90%, 95%, 96%, 97%, 98%, 99%, or 100% identical to SEQ ID NO: 50 and/or a light chain variable region encoded by a nucleotide sequence at least 80%, 85%, 90%, 95%, 96%, 97%, 98%, 99%, or 100% identical to SEQ ID NO: 51.

Embodiment 36 provides the nucleic acid of embodiment 34, wherein the antigen binding domain is a single-chain variable fragment (scFv) encoded by a nucleotide sequence at least 80%, 85%, 90%, 95%, 96%, 97%, 98%, 99%, or 100% identical to SEQ ID NO: 52 or SEQ ID NO: 53.

Embodiment 37 provides the nucleic acid of embodiment 34, wherein the CAR is encoded by a nucleotide sequence at least 80%, 85%, 90%, 95%, 96%, 97%, 98%, 99%, or 100% identical to SEQ ID NO: 54 or 55.

Embodiment 38 provides the nucleic acid of embodiment 34, wherein the antigen binding domain comprises a heavy chain variable region encoded by a nucleotide sequence at least 80%, 85%, 90%, 95%, 96%, 97%, 98%, 99%, or 100% identical to SEQ ID NO: 56 and/or a light chain variable region encoded by a nucleotide sequence at least 80%, 85%, 90%, 95%, 96%, 97%, 98%, 99%, or 100% identical to SEQ ID NO: 57.

Embodiment 39 provides the nucleic acid of embodiment 34, wherein the antigen binding domain is a single-chain variable fragment (scFv) encoded by a nucleotide sequence at least 80%, 85%, 90%, 95%, 96%, 97%, 98%, 99%, or 100% identical to SEQ ID NO: 58 or SEQ ID NO: 59.

Embodiment 40 provides the nucleic acid of embodiment 34, wherein the CAR is encoded by a nucleotide sequence at least 80%, 85%, 90%, 95%, 96%, 97%, 98%, 99%, or 100% identical to SEQ ID NO: 60 or 61.

Embodiment 41 provides a vector comprising the nucleic acid of any one of embodiments 30-40.

Embodiment 42 provides a modified immune cell or precursor cell thereof, comprising the CAR of any one of embodiments 1-29, or the nucleic acid of any one of claims 30-40.

Embodiment 43 provides the modified immune cell or precursor cell of embodiment 42, wherein the modified cell is an autologous cell.

Embodiment 44 provides the modified immune cell or precursor cell of embodiment 42, wherein the modified cell is a cell isolated from a human subject.

Embodiment 45 provides the modified immune cell or precursor cell of embodiment 42, wherein the modified cell is a modified T cell.

Embodiment 46 provides a method for generating a modified immune cell or precursor cell thereof, comprising: introducing into an immune or precursor cell the nucleic acid of any one of embodiments 30-40 or the vector of embodiment 41.

Embodiment 47 provides the method of embodiment 46, wherein the nucleic acid is introduced via viral transduction.

Embodiment 48 provides the method of embodiment 47, wherein the viral transduction comprises contacting the immune or precursor cell with a viral vector comprising the nucleic acid encoding a CAR.

Embodiment 49 provides the method of embodiment 48, wherein the viral vector is selected from the group consisting of a retroviral vector, a lentiviral vector, an adenoviral vector, and an adeno-associated viral vector.

Embodiment 50 provides the method of embodiment 49, wherein the viral vector is a lentiviral vector.

Embodiment 51 provides a method of treating cancer in a subject in need thereof, comprising administering to the subject the modified immune or precursor cell of any one of embodiments 42-45, or a modified immune or precursor cell generated by the method of embodiments 46-50.

Embodiment 52 provides a method of treating cancer in a subject in need thereof, comprising administering to the subject a modified T cell comprising a chimeric antigen receptor (CAR), wherein the CAR comprises an antigen binding domain capable of binding the IIICS domain of fibronectin, a transmembrane domain, and an intracellular domain.

Embodiment 53 provides the method of claim 52, wherein the antigen binding domain comprises at least one heavy chain variable region (HCDR) comprising the nucleotide sequence selected from the group consisting of SEQ ID NO: 1, SEQ ID NO: 2, and SEQ ID NO: 3.

Embodiment 54 provides the method of embodiment 52, wherein the antigen binding domain comprises at least one light chain variable region (LCDR) comprising the nucleotide sequence selected from the group consisting of SEQ ID NO: 4, SEQ ID NO: 5, and SEQ ID NO: 6.

Embodiment 55 provides the method of claim 52, wherein the antigen binding domain comprises a heavy chain variable region comprising an amino acid sequence at least 80%, 85%, 90%, 95%, 96%, 97%, 98%, 99%, or 100% identical to SEQ ID NO: 7 and/or a light chain variable region comprising an amino acid sequence at least 80%, 85%, 90%, 95%, 96%, 97%, 98%, 99%, or 100% identical to SEQ ID NO: 8.

Embodiment 56 provides the method of embodiment 52, wherein the antigen binding domain is a single-chain variable fragment (scFv) comprising an amino acid sequence at least 80%, 85%, 90%, 95%, 96%, 97%, 98%, 99%, or 100% identical to SEQ ID NO: 10 or SEQ ID NO: 11.

Embodiment 57 provides a method of treating cancer in a subject in need thereof, comprising administering to the subject a modified T cell comprising a chimeric antigen receptor (CAR), wherein the CAR comprises an antigen binding domain capable of binding the EDB domain of fibronectin, a transmembrane domain, and an intracellular domain.

Embodiment 58 provides the method of embodiment 57, wherein the antigen binding domain comprises at least one heavy chain variable region (HCDR) comprising the nucleotide sequence selected from the group consisting of SEQ ID NO: 12, SEQ ID NO: 13, and SEQ ID NO: 14.

Embodiment 59 provides the method of embodiment 57, wherein the antigen binding domain comprises at least one light chain variable region (LCDR) comprising the nucleotide sequence selected from the group consisting of SEQ ID NO: 15, SEQ ID NO: 16, and SEQ ID NO: 17.

Embodiment 60 provides the method of embodiment 57, wherein the antigen binding domain comprises a heavy chain variable region comprising an amino acid sequence at least 80%, 85%, 90%, 95%, 96%, 97%, 98%, 99%, or 100% identical to SEQ ID NO: 18 and/or a light chain variable region comprising an amino acid sequence at least 80%, 85%, 90%, 95%, 96%, 97%, 98%, 99%, or 100% identical to SEQ ID NO: 19.

Embodiment 61 provides the method of embodiment 57, wherein the antigen binding domain comprises at least one heavy chain variable region (HCDR) comprising the nucleotide sequence selected from the group consisting of SEQ ID NO: 23, SEQ ID NO: 24, and SEQ ID NO: 25.

Embodiment 62 provides the method of embodiment 57, wherein the antigen binding domain comprises at least one light chain variable region (LCDR) comprising the nucleotide sequence selected from the group consisting of SEQ ID NO: 26, SEQ ID NO: 27, and SEQ ID NO: 28.

Embodiment 63 provides the method of embodiment 57, wherein the antigen binding domain comprises a heavy chain variable region comprising an amino acid sequence at least 80%, 85%, 90%, 95%, 96%, 97%, 98%, 99%, or 100% identical to SEQ ID NO: 29 and/or a light chain variable region comprising an amino acid sequence at least 80%, 85%, 90%, 95%, 96%, 97%, 98%, 99%, or 100% identical to SEQ ID NO: 30.

Embodiment 64 provides the method of embodiment 57, wherein the antigen binding domain is a single-chain variable fragment (scFv) comprising an amino acid sequence at least 80%, 85%, 90%, 95%, 96%, 97%, 98%, 99%, or 100% identical to SEQ ID NO: 31 or SEQ ID NO: 32.

Embodiment 65 provides the method of any one of embodiments 52-64, wherein the antigen binding domain is selected from the group consisting of a full length antibody or antigen-binding fragment thereof, a Fab, a single-chain variable fragment (scFv), or a single-domain antibody.

Embodiment 66 provides the method of any one of embodiments 52-65, wherein the CAR further comprises a CD8 alpha hinge sequence comprising the amino acid sequence set forth in SEQ ID NO: 34.

Embodiment 67 provides the method of any one of embodiments 52-68, wherein the transmembrane domain comprises a transmembrane domain selected from the group consisting of an artificial hydrophobic sequence, and a transmembrane domain of a type I transmembrane protein, an alpha, beta, or zeta chain of a T cell receptor, CD28, CD3 epsilon, CD45, CD4, CD5, CD8, CD9, CD16, CD22, CD33, CD37, CD64, CD80, CD86, OX40 (CD134), 4-1BB (CD137), ICOS, and CD154, or a transmembrane domain derived from a killer immunoglobulin-like receptor (KIR).

Embodiment 68 provides the method of any one of embodiments 52-67, wherein the transmembrane domain comprises a transmembrane domain of CD8 alpha comprising the amino acid sequence set forth in SEQ ID NO: 35.

Embodiment 69 provides the method of any one of embodiments 52-68, wherein the intracellular domain comprises a costimulatory signaling domain and an intracellular signaling domain.

Embodiment 70 provides the method of any one of embodiments 52-69, wherein the intracellular domain comprises a costimulatory domain of a protein selected from the group consisting of proteins in the TNFR superfamily, CD28, 4-1BB (CD137), OX40 (CD134), PD-1, CD7, LIGHT, CD83L, DAP10, DAP12, CD27, CD2, CD5, ICAM-1, LFA-1, Lck, TNFR-I, TNFR-II, Fas, CD30, CD40, ICOS, NKG2C, and B7-H3 (CD276), or a variant thereof, or an intracellular domain derived from a killer immunoglobulin-like receptor (KIR).

Embodiment 71 provides the method of any one of embodiments 52-70, wherein the intracellular domain comprises a costimulatory domain of 4-1BB.

Embodiment 72 provides the method of embodiment 71, wherein the costimulatory domain of 4-1BB comprises the amino acid sequence set forth in SEQ ID NO: 36.

Embodiment 73 provides the method of any one of embodiments 52-72, wherein the intracellular signaling domain comprises an intracellular domain selected from the group consisting of cytoplasmic signaling domains of a human CD3 zeta chain (CD3), FcγRIII, FcsRI, a cytoplasmic tail of an Fc receptor, an immunoreceptor tyrosine-based activation motif (ITAM) bearing cytoplasmic receptor, TCR zeta, FcR gamma, CD3 gamma, CD3 delta, CD3 epsilon, CD5, CD22, CD79a, CD79b, and CD66d, or a variant thereof.

Embodiment 74 provides the method of any one of embodiments 52-73, wherein the intracellular signaling domain comprises an intracellular domain of CD3 or a variant thereof.

Embodiment 75 provides the method of embodiment 73, wherein the intracellular domain of CD3ζ comprises the amino acid sequence set forth in SEQ ID NO: 37.

Embodiment 76 provides the method of any one of claims 52-75, wherein the CAR comprises an amino acid sequence at least 80%, 85%, 90%, 95%, 96%, 97%, 98%, 99%, or 100% identical to SEQ ID NO: 38, 39, 40, 41, 42, or 43.

Embodiment 77 provides the method of any one of embodiments 52-76, wherein the CAR is encoded by a nucleotide sequence at least 80%, 85%, 90%, 95%, 96%, 97%, 98%, 99%, or 100% identical to SEQ ID NO: 48, 49, 54, 55, 60, or 61.

Embodiment 78 provides the method of any one of embodiments 52-77, wherein the modified T cell is human.

Embodiment 79 provides the method of any one of embodiments 52-78, wherein the modified T cell is autologous.

Embodiment 80 provides the method of any one of embodiments 52-79, wherein the subject is human.

OTHER EMBODIMENTS

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A chimeric antigen receptor (CAR) comprising an antigen binding domain capable of binding the IIICS domain of fibronectin, a transmembrane domain, and an intracellular domain, wherein the antigen binding domain comprises:

i. at least one heavy chain variable region (HCDR) comprising the nucleotide sequence selected from the group consisting of SEQ ID NO: 1, SEQ ID NO: 2, and SEQ ID NO: 3; and ii. at least one light chain variable region (LCDR) comprising the nucleotide sequence selected from the group consisting of SEQ ID NO: 4, SEQ ID NO: 5, and SEQ ID NO: 6.

2. The CAR of claim 1, wherein the antigen binding domain comprises a heavy chain variable region comprising the amino acid sequence of SEQ ID NO: 7.

3. The CAR of claim 1, wherein the antigen binding domain comprises a light chain variable region comprising the amino acid sequence of SEQ ID NO: 8.

4. The CAR of claim 1, wherein the antigen binding domain is a single-chain variable fragment (scFv) comprising the amino acid sequence of SEQ ID NO: 10 or SEQ ID NO: 11.

5. A nucleic acid comprising a polynucleotide sequence encoding the chimeric antigen receptor (CAR) of claim 1.

6. The nucleic acid of claim 5, wherein the antigen binding domain comprises a heavy chain variable region encoded by a nucleotide sequence comprising the nucleotide sequence of SEQ ID NO: 44 and/or a light chain variable region encoded by a nucleotide sequence comprising the nucleotide sequence of SEQ ID NO: 45.

7. The nucleic acid of claim 5, wherein the antigen binding domain is a single-chain variable fragment (scFv) encoded by a nucleotide sequence comprising the nucleotide sequence of SEQ ID NO: 46 or SEQ ID NO: 47.

8. The nucleic acid of claim 5, wherein the CAR is encoded by a nucleotide sequence comprising the nucleotide sequence of SEQ ID NO: 48 or 49.

9. A vector comprising the nucleic acid of claim 5.

10. A modified immune cell or precursor cell thereof, comprising the CAR of claim 1.

11. The modified immune cell or precursor cell thereof of claim 10, wherein the modified cell is a modified T cell.

12. A method for generating a modified immune cell or precursor cell thereof, comprising introducing into an immune or precursor cell the nucleic acid of claim 5.

13. The method of claim 12, wherein the nucleic acid is introduced via viral transduction.

14. The method of claim 13, wherein the viral transduction comprises contacting the immune or precursor cell with a viral vector comprising the nucleic acid encoding a CAR.

15. The method of claim 14, wherein the viral vector is selected from the group consisting of a retroviral vector, a lentiviral vector, an adenoviral vector, and an adeno-associated viral vector.

16. The method of claim 15, wherein the viral vector is a lentiviral vector.

* * * * *